US012668784B2

(12) United States Patent
Redding et al.

(10) Patent No.: US 12,668,784 B2
(45) Date of Patent: Jun. 30, 2026

(54) PHOTOSYSTEM I-HYDROGENASE CHIMERAS FOR HYDROGEN PRODUCTION

(71) Applicants: Kevin Redding, Tempe, AZ (US);
Andrey Kanygin, Phoenix, AZ (US)

(72) Inventors: Kevin Redding, Tempe, AZ (US);
Andrey Kanygin, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 18/744,124

(22) Filed: Jun. 14, 2024

(65) Prior Publication Data

US 2024/0327805 A1     Oct. 3, 2024

Related U.S. Application Data

(62) Division of application No. 17/565,684, filed on Dec. 30, 2021, now Pat. No. 12,065,676.

(60) Provisional application No. 63/132,219, filed on Dec. 30, 2020.

(51) Int. Cl.
| | |
|---|---|
| *C12N 9/02* | (2006.01) |
| *C12N 1/12* | (2006.01) |
| *C12N 15/62* | (2006.01) |
| *C12P 3/00* | (2006.01) |
| *C07K 14/405* | (2006.01) |

(52) U.S. Cl.
CPC .............. *C12N 9/0077* (2013.01); *C12N 1/12* (2013.01); *C12N 15/62* (2013.01); *C12P 3/00* (2013.01); *C07K 14/405* (2013.01); *C07K 2319/00* (2013.01)

(58) Field of Classification Search
CPC .................................................... C12N 9/0077
See application file for complete search history.

(56) References Cited

U.S. PATENT DOCUMENTS

2012/0021479 A1     1/2012   Silver

OTHER PUBLICATIONS

Melis et al., "Sustained Photobiological Hyrdrogen Gas Production upon Reversible Inactivation of Oxygen Evolution in the Green Alga Chlamydomonas reinhardtii[1]", Plant Physiology, Jan. 2000, vol. 122, pp. 127-135.
Milrad et al., "Green Algal Hydrogenase Activity is Outcompeted by Carbon Fixation before Inactivation by Oxygen Takes Place[1]," Plant Physiology, Jul. 2018, vol. 177, pp. 918-926.
Milrad et al., "Bi-directional electron transfer between $H_2$ and NADPH mitigates light fluctuation responses in green algae," Plant Physiology (2021) 186: 168-179.

(Continued)

*Primary Examiner* — Yong D Pak
(74) *Attorney, Agent, or Firm* — Quarles & Brady LLP

(57) ABSTRACT

Provided herein, in some embodiments, are engineered cells and use of the same for increased hydrogen production. In particular, provided herein are genetically engineered cells comprising a polynucleotide encoding a fusion protein comprising a photosystem I (PSI) protein and an algal hydrogenase, as well as methods for producing such genetically engineered cells. Also provided herein are methods for increasing hydrogen ($H_2$) production in cells.

4 Claims, 39 Drawing Sheets
(34 of 39 Drawing Sheet(s) Filed in Color)
Specification includes a Sequence Listing.

(56)         References Cited

OTHER PUBLICATIONS

Meuser et al., "Genetic disruption of both Chlamydomonas reinhardtii [FeFe]-hydrogenases: Insight into the role of HDA2 in $H_2$ production," Biochemical and Biophysical Research Communications 417 (2012) 704-709.

Mulder et al., "Stepwise [FeFe]-hydrogenase H-cluster assembly revealed in the structure of HydA." Nature, vol. 465, May 13, 2010, 5 pages.

Nawrocki et al., "The mechanism of cyclic electron flow," BBA—Bioenergeteics 1860 (2019) 433-438.

Nelson et al., "The Complex Architecture of Oxygenic Photosynthesis," Nature Reviews, Molecular Cell Biology, vol. 5, Dec. 2004, 13 pages.

Nikolova et al., "Absolute quantification of selected photosynthetic electron transfer proteins in Chlamydomonas reinhardtii in the presence and absence of oxygen," Photosynthesis Research (2018) 137:281-293.

Noth et al., "Pyruvate: Ferredoxin Oxidoreductase is Coupled to Light-independent Hydrogen Production in Chlamydomonas reinhardtii," The Journal of Biological Chemistry, vol. 288, No. 6, pp. 4368-4377, Feb. 8, 2013.

Ostersetzer et al., "Light-Stimulated Degradation of an Unassembled Rieske FeS Protein by a Thylakoid-Bond Protease: The Possible Role of the FtsH Protease," The Plant Cell, vol. 9, 957-965, Jun. 1997.

Pinto et al., "Rubisco mutants of Chlamydomonas reinhardtii enhance photosynthetic hyrdrogen production," Appl Microbiol Biotehnol (2013) 97:5635-5643.

Polle et al., "Photosynthetic apparatus organization and function in the wild type and a chlorophyll b-less mutant of Chlamydomonas reinhardtii, Dependence on carbon source," Planta (2000) 211: 335-344.

Polukhina et al., "Carbon Supply and Photoacclimation Cross Talk in the Green Alga Chlamydomonas reinhardtii," Plant Physiology, Nov. 2016, vol. 172, pp. 1494-1505.

Porra et al., "Determination of accurate extinction coefficients and simultaneous equations for assaying chlorophylls a and b extracted with four different solvents: verification of the concentration of chlorophyll standards by atomic absorption spectroscopy," Biochimica et Biophysica Acta, 975 (1989) 384-394.

Posewitz et al., "Discovery of Two Novel Radical S-Adenosylmethionine Proteins Required for the Assembly of an Active [Fe] Hydrogenase," The Journal of Biological Chemistry, vol. 249, No. 24, pp. 25711-25720 (2004).

Reifschneider-Wegner et al., "Expression of the [FeFe] hydrogenase in the chloroplast of Chlamydomonas reinhardtii," International Journal of Hydrogen Energy 39 (2014) 3657-3665.

Rumpel et al., "Structural Insight into the Complex of Ferredoxin and [FeFe] Hydrogenase from Chlamydomonas reinhardtii," ChemBioChem (2015) 16, 1663-1669.

Santabarbara et al., "Temperature Dependence of the Reduction of $P_{700}$ by Tightly Bound Plastocyanin in Vivo," Biochemistry, (2009) 48, 10457-10466.

Sawyer et al., "Compartmentalisation of [FeFe]-hydrogenase maturation in Chlamydomonas reinhardtii," The Plant Journal (2017) 90, 1134-1143.

Setif, "Ferredoxin and flavodoxin reduction by photosystem I," Biochimica et Biophysica Acta 1507 (2001) 161-179.

Setif et al., "The ferredoxin docking site of photosystem I," Biochimica et Biophysica Acta 1555 (2002) 204-209.

Shepard et al., "[FeFe]-Hydrogenase Maturation," Biochemistry (2014) 53, 4090-4104.

Song et al., "High-Resolution Comparative Modeling with RosettaCM," Structure 21, 1735-1742, Oct. 8, 2013.

Stirbet et al., "Photosynthesis: basics, history and modeling," Annals of Botany 126: 511-537, (2020).

Stripp et al., "How oxygen attacks [FeFe] hydrogenases from photosynthetic organisms," PNAS, Oct. 13, 2013, vol. 106, No. 41, 17331-17336.

Su et al., "Antenna arrangement and energy transfer pathways of a green algal photosystem-I-LHCI supercomplex," Nature Plants, vol. 5, Mar. 2019, pp. 273-281.

Swanson et al., "[FeFe]-Hydrogenase Oxygen Inactivation is Initiated at the H Cluster 2Fe Subcluster," J. Am. Chem. Soc. (2015) 137, 1809-1816.

Swartz, "Opportunities toward hydrogen production biotechnologies," Current Opinion in Biotechnology (2020) 62:248-255.

Takahashi et al., "Directed chloroplast transformation in Chlamydomonas reinhardtii: insertional inactivation of the psaC gene encoding the iron sulfur protein destabilizes photosystem I," The EMBO Journal, vol. 10, No. 8, pp. 2033-2040 (1991).

Takahashi et al., "Cyclic electron flow is redox-controlled but independent of state transition," Nature Communications, 4:1954 (2013).

Tirumani et al., "Coordination between photorespiration and carbon concentrating mechanism in Chlamydomonas reinhardtii: transcript and protein changes during light-dark diurnal cycles and mixotrophy conditions," Protoplasma (2019) 256:117-130.

Torzillo et al., "Advances in the biotechnology of hydrogen production with the microalga Chlamydomonas reinhardtii," Crit Rev Biotechnol (2014), 13 pages.

Urbig et al., "Inactivation and Reactivation of they Hydrogenases of the Green Algae Scenedesmus obliquus and Chlamydomonas reinhardtii," Z. Naturforsch. 48c, 41-45 (1993).

Von Abendroth et al., "Optimized over-expression of [FeFe] hydrogenases with high specific activity in Clostridium acetobutylicum," International Journal of Hydrogen Energy 33 (2008) 6076-6081.

Wang et al., "Analysis of photosynthetically active radiation under various sky conditions in Wuhan, Central China," Int J. Biometeorol (2014) 58:1711-1720.

Weis et al., "Computed tomography of cryogenic biological specimens based on X-ray microscopic images," Ultramicroscopy 84 (2000) 185-197.

Winkler et al., "Characterization of the Key Step for Light-driven Hydrogen Evolution in Green Algae," The Journal of Biological Chemistry, vol. 284, No. 52, pp. 36620-36627, Dec. 25, 2009.

Winkler et al., "Multiple ferredoxin isoforms in Chlamydomonas reinhardtii—Their role under stress conditions and biotechnological implications," European Journal of Cell Biology 89 (2010) 998-1004.

Witt et al., "Species-specific Differences of the Spectroscopic Properties of P700, Analysis of the Influence of Non-Conserved Amino Acid Residues By Site-Directed Mutagenesis of Photosystem I from Chlamydomonas Reinhardtii," The Journal of Biological Chemistry, vol. 278, No. 47, pp. 46760-46771, (2003).

Xie et al., "Photorespiration participates in the assimilation of acetate in Chlorella sorokiniana under high light," New Phytologist (2016) 209: 987-998.

Yacoby et al., "Photosynthetic electron partitioning between [FeFe]-hydrogenase and ferredoxin: NADP-oxidoreductase (FNR) enzymes in vitro," PNAS, vol. 108, No. 23, 9396-9401 (2011).

Zhao et al., "Measurement of Photosystem I Activity with Photoreduction of Recombinant Flavodoxin," Analytical Biochemistry, 264, 263-270 (1998).

Fiser et al. "Modeling of loops in protein structures," Protein Science, 9:1753-1773 (2000).

Kanygin. Rewiring photosynthesis: a photosystem I-hydrogenase chimera that makes H2 in vivo. Energy and Environmental Science 13 (2020): 2903-2914 and Supplementary Material.

AOA 1 B1FK82_9CH LO. UniProtKB/TrEM BL Database. Nov. 2, 2016.

Alric et al., "Redox and ATP control of photosynthetic cyclic electron flow in Chlamydomonas reinhardtii (I) aerobic conditions," Biochimica et Biophysica Acta 1797 (2010) 44-51.

Bai et al., "Iron-sulphur cluster biogenesis via the SUF pathway," Metallomics, (2018) 10, 1038-1052.

Ben-Zvi et al., "Re-routing photosynthetic energy for continuous hydrogen production in vivo," Biotechnol Biofuels (2019) 12:266.

(56)　　　　　References Cited

OTHER PUBLICATIONS

Berggren et al., "Biomimetic assembly and activation of [FeFe]-hydrogenases," Nature, vol. 499, 5 pages, (2013).

Bohme, "Quantitative Determination of Ferredoxin, Ferredoxin-NADP Reductase and Plastocyanin in Spinach Chloroplasts," Eur. J. Biochem. 83, 137-141 (1978).

Brettel, "Electron transfer and arrangement of the redox cofactors in photosystem I," Biochimica et Biophysica Acta 1318 (1997) 322-373.

Brettel et al., "Electron transfer in photosystem I," Biochimica et Biophysica Acta 1507 (2001) 100-114.

Britt et al., "Proposed Mechanism for the Biosynthesis of the [FeFe] Hydrogenase H-Cluster: Central Roles for the Radical SAM Enzymes HydG and HydE," ACS Bio Med Chem Au (2022) 11-21.

Burlacot et al., "Flavodiiron-Mediated $O_2$ Photoreduction Links $H_2$ Production with $CO_2$ Fixation during the Anaerobic Induction of Photosynthesis," Plant Physiology, Aug. 2018, vol. 177, pp. 1639-1649.

Burlacot et al., "Membrane Inlet Mass Spectrometry: A Powerful Tool for Algal Research," Front. Plant Sci., Sep. 2020, vol. 11, Article 1302.

Byrdin et al., "Assignment of a kinetic component to electron transfer between iron-sulfur clusters $F_x$ and FA/B of Photosystem I," Biochemica et Biophysica Acta 1757 (2006) 1529-1538.

Cashman et al., "Molecular interactions between photosystem I and ferredoxin: an integrated energy frustration and experimental model," J. Moi. Recognit. 2014; 27: 597-608.

Chang et al., "Atomic Resolution Modeling of the Ferredoxin: [FeFe] Hydrogenase Complex from Chlamydomonas reinhardtii," Biophysical Journal, vol. 93, Nov. 2007, 3034-3045.

Chapman et al., "Flux balance analysis reveals acetate metabolism modulates cyclic electron flow and alternative glycolytic pathways in Chlamydomonas reinhardtii," Front. Plant Sci., Jun. 2015, vol. 6, Article 474, 14 pages.

Clowez et al., "The Involvement of Hydrogen-producing and ATP-dependent NADPH-consuming Pathways in Setting the Redox Poise in the Chloroplast of Chlamydomonas reinhardtii in Anoxia," The Journal of Biological Chemistry, vol. 290, No. 13, pp. 8666-8676, Mar. 27, 2015.

Cournac et al., "Limiting steps of hydrogen production in Chlamydomonas reinhardtii and Synechocystis PCC 6803 as analysed by light-induced gas exchange transients," International Journal of Hydrogen Energy 27, (2002) 1229-1237.

Decottignies et al., "Primary Structure and Post-translation Modification of Ferredoxin-NADP Reductase from Chlamydomonas reinhardtii," Archives of Biochemisty and Biophysics, vol. 316, No. 1, pp. 249-259, (1995).

Decottignies et al., "Role of positively charged residues in Chlamydomonas reinhardtii ferredoxin-NADP+—reductase," Plant Physiology and Biochemistry 41 (2003) 637-642.

Eilenberg et al., "The dual effect of a ferredoxin-hydrogenase fusion protein in vivo: successful divergence of the photosynthetic electron flux towards hyrdrogen production and elevated oxygen tolerance," Biotechnol Biofuels (2016) 9:182.

Erbes et al., "Inactivtion of Hydrogenase in Cell-free Extracts and Whole Cells of Chlamydomonas reinhardi by Oxygen[1]," Plant Physiol. (1979) 63, 1138-1142.

Fischer et al., "Targeted Mutations in the psaC Gene of Chlamydomonas reinhardtii: Preferential Reduction of FB at Low Temperature is not Accompanied by Altered Electron Flow from Photosystem I to Ferredoxin," Biochemistry (1997) 36, 93-102.

Fischer et al., "The PsaC subunit of photosystem I provides an essential lysine residue for fast electron transfer to ferredoxin," The EMBO Journal vol. 17, No. 4, pp. 849-858, (1998).

Fischer et al., "Site-directed Mutagenesis of the PsaC Subunit of Photosystem I $F_B$ is the Cluster Interacting With Soluble Ferredoxin," The Journal of Biological Chemistry vol. 274, No. 33, pp. 23333-23340, (1999).

Forestier et al., "Expression of two [Fe]-hydrogenases in Chlamydomonas reinhardtii under anaerobic conditions," Eur. J. Biochem. 270, 2750-2758 (2003).

Genty et al., "The relationship between the quantum yield of photosynthetic electron transport and quenching of cholorophyll fluorescence," Biohimica et Biophysica Acta, 990 (1989) 87-92.

Ghysels et al., "Function of the Chloroplast Hydrogenase in the Microalga Chlamydomonas: The Role of Hydrogenase and State Transitions during Photosynthetic Activation in Anaerobiosis," PLoS ONE 8(5): e64161. doi:10.1371/journal.pone.0064161 (2013).

Godaux et al., "Induction of Photosynthetic Carbon Fixation in Anoxia Relies on Hydrogenase Activity and Proton-Gradient Regulation-Like1-Mediated Cyclic Electron Flow in Chlamydomonas reinhardtii[1]," Plant Physiology, Jun. 2015, vol. 168, pp. 648-658.

Gulis et al., "Purification of His6-tagged Photosystem I from Chlamydomonas reinhardtii," Phtosynth Res (2008) 96:51-60.

Happe et al., "Isolation, characterization and N-terminal amino acid sequence of hydrogenase from the green alga Chlamydomonas reinhardtii," Eur. J. Biochem. 214, 475-481 (1993).

Happe et al., "Differential regulation of the Fe-hydrogenase during anaerobic adaption in the green alga Chlamydomonas reinhardtii," Eur. J. Biochem. 269, 1022-1032 (2002).

Hoober et al., "Characterization of the Chloroplastic and Cytoplasmic Ribosomes of Chlamydomonas reinhardi," J. Mol. Biol. (1969) 41, 121-138.

Hydrogen Council, "Hydrogen Insights: A perspective on hydrogen investment, market development and cost competitiveness," Hydrogen Insights Report 2021.

Johnson et al., "Interaction between Starch Breakdown, Acetate Assimilation, and Photosynthetic Cyclic Electron Flow in Chlamydomonas reinhardtii," The Journal of Biological Chemistry, vol. 287, No. 31, pp. 26445-26452, Jul. 27, 2012.

Jordan et al., "Three-dimensional structure of cyanobacterial photosystem I at 2.5 A resolution," Nature, vol. 411, Jun. 21, 2001, 9 pages.

Kaiser, "Reversible Inhibition of the Calvin Cycle and Activation of Oxidative Pentose Phosphate Cycle in Isolated Intact Chloroplasts by Hydrogen Peroxide," Planta, vol. 145, No. 4 (1979), pp. 377-382.

Kanygin et al., "Rewiring photosynthesis: a photosystem I-hydrogenase chimera that makes $H_2$ in vivo," Energy Environ. Sci., (2020), 13, 2903-2914.

Kelley et al., "The Phyre2 web portal for protein modeling, prediction and analysis," Nature Protocols, vol. 10, No. 6, (2015) 845.

Kosourov et al., "A new approach for sustained and efficient $H_2$ photoproduction by Chlamydomonas reinhardtii," Energy Environ. Sci., (2018) 11, 1431.

Kosourov et al., "Water oxidation by photosytem II is the primary source of electrons for sustained $H_2$ photoproduction in nutrient-replete green algae," PNAS, Nov. 24, 2020, vol. 117, No. 47, 29629-29636.

Kozakov et al., "The ClusPro web server for protein-protein docking," Nat Protoc. Feb. 2017; 12(2): 255-278.

Kropat et al., "A revised mineral nutrient supplement increases biomass and growth rate in Chlamydomonas reinhardtii," The Plant Journal (2011) 66, 770-780.

Kubas et al., "Mechanism of $O_2$ diffusion and reduction in FeFe hydrogenases," Nature Chemistry, vol. 9, 8 pages, Jan. 2017.

Kuhlgert et al., "Residues PsaB Asp612 and PsaB Glu613 of Photosystem I Confer pH-Dependent Binding of Plastocyanin and Cytochrome c6," Biochemistry, (2012) 51, 7297-7303.

Li et al., "Mutation of the Putative Hydrogen-Bond Donor to P700 of Photosystem I," Biochemistry (2004) 43, 12634-12647.

Liran et al., "Microoxic Niches within the Thylakoid Stroma of Air-Grown Chlamydomonas reinhardtii Protect [FeFe]—Hydrogenase and Support Hydrogen Production under Fully Aerobic Environment[1]," Plant Physiology, Sep. 2016, vol. 172, pp. 264-271.

Lubitz et al., "Hydrogenases," Chem. Rev. (2014) 114, 4081-4148.

Lubner et al., "Solar hydrogen-producing bionanodevice outperforms natural photosynthesis," PNAS, Dec. 27, 2011, vol. 108, No. 52, 20988-20991.

(56)     References Cited

OTHER PUBLICATIONS

Marco et al., "Binding of ferredoxin to algal photosytem I involves a single binding site and is composed of two thermodynamically distinct events," BBA—Bioenergetics 1859 (2018) 234-243.

Meimberg et al., "Lys35 of PsaC is required for the efficient photoreduction of flavodoxin by photosystem I from Chlamydomonas reinhardtii," Eur. J. Biochem. 263, 137-144 (1999).

Meimberg et al., "Laser-flash absorption spectroscopy study of the competition between ferredoxin and flavodoxin photoreduction by Photosystem I in *Synechococcus* sp. PCC 7002: Evidence for a strong preference for ferredoxin," Photosynthesis Research 61, 253-267, (1999).

FIGS. 1A-1C, CONTINUED
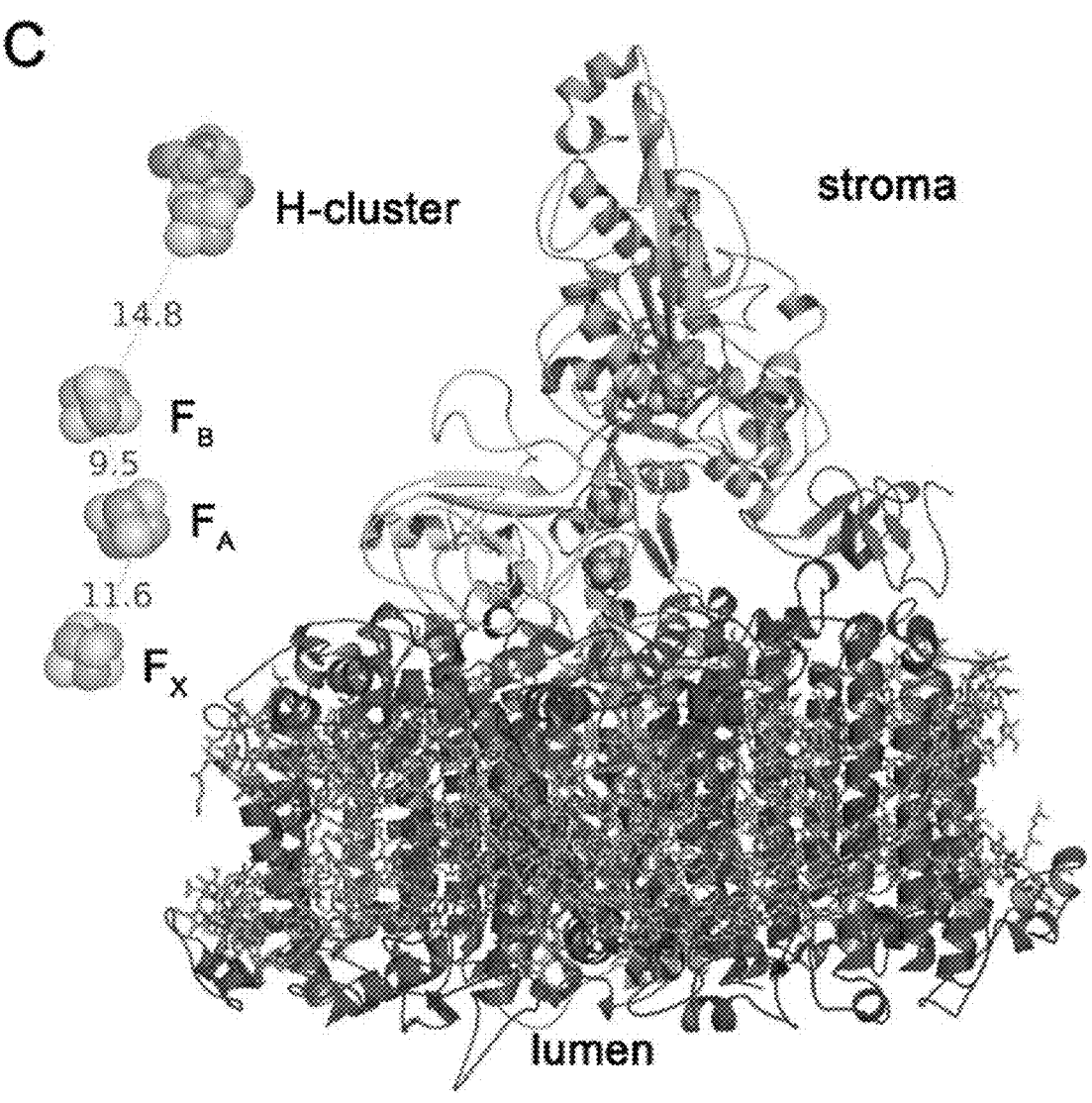

FIG. 6

SEQ ID NO: 1

MAHVKIYDTCIGCTQCVRACPLDVLEMVPWGGATATDAVPHWKLALEELDKP
KDGGRKVLIAQVAPAVRVAIAESFGLAPGAVSPGKLATGLRALGFDQVFDTLFA
ADLTIMEEGTELLHRLKEHLEAHPHSDEPLPMFTSCCPGWVAMMEKSYPELIPFV
SSCKSPQMMMGAMVKTYLSEKQGIPAKDIVMVSVMPCVRKQGEADREWFCVSE
PGVRDVDHVITTAELGNIFKERGINLPELPDSDWDQPLGLGSGAGVLFGTTGGVM
EAALRTAYEIVTKEPLPRLNLSEVRGLDGIKEASVTLVPAPGSKFAELVAERLAHK
VEEAAAAEAAAAVEGAVKPPIAYDGGQGFSTDDGKGGLKLRVAVANGLGNAK
KLIGKMVSGEAKYDFVEIMACPAGCVGGGQPRSTDKQITQKRQAALYDLDERN
TLRRSHENEAVNQLYKEFLGEPLSHRAHELLHTHYVPGGKSQMASAPRTEDCVG
CKRCETACPTDFLSVRVYLGSESTRSMGLSY

A

B

| Assignment of phase | Time constant ± SE, ms (relative amplitude, %) | |
|---|---|---|
| | PSI$^{H6}$ | PSI$^{H6}$-HydA2 |
| CR of P$_{700}$$^+$F$_X$$^-$ | N/A | 0.56 ± 0.10 (7.3)<br>3.0 ± 0.6 (4.6) |
| CR of P$_{700}$$^+$(F$_A$F$_B$)$^-$ | 63 ± 4 (28.1)<br>204 ± 7 (44.5) | 45 ± 3 (17.5)<br>192 ± 15 (35.8) |
| CR of P$_{700}$$^+$F$_H$$^-$ | N/A | 570 ± 81 (9.1) |
| ascorbate | 30,000 ± 2750 (24.1) | 25,500 ± 1060 (23.9) |
| Non-decaying | − (3.3) | − (1.8) |
| R$^2$ | 0.9999 | 0.9999 |

SEQ ID NO: 2

MAHIVKIYDTCIGCTQCVRACPLDVLEMVPWGGATATDAVPHVQQALAELAKPKDDPTRKHVCVQVAPAV
RVAIAETLGLAPGATTPKQLAEGLRRLGFDEVFDTLFGADLTIMEEGSELLHRLTEHLEAHPHSDEPLPMFTSC
CPGWIAMLEKSYPDLIPYVSSCKSPQMMLAAMVKSYLAEKKGIAPKDMVMVSIMPCTRKQSEADRDWFCV
DADPTLRQLDHVITTVELGNIFKERGINLAELPEGEWDNPMGVGSGAGVLFGTTGGVMEAALRTAYELFTGT
PLPRLSLSEVRGMDGIKETNITMVPAPGSKFEELLKHRAAARAEAAAHGTPGPLAWDGGAGFTSEDGRGGIT
LRVAVANGLGNAKKLITKMQAGEAKYDFVEIMACPAGCVGGGGQPRSTDKAITQKRQAALYNLDEKSTLRR
SHENPSIRELYDTYLGEPLGHKAHELLHTHYVAGGASQMASAPRTEDCVGCKRCETACPTDFLSVRVYLGSES
TRSMGLSY

```
                              β-hairpin

|        |

MAHIVKIYDTCIGCTQCVRACPLDVLEMVPWDGCKASQMASAPRTEDCVGCKRCETACPT   60 #1

MSHTVKIYDTCIGCTQCVRACPTDVLEMVPWDGCKASQIASAPRTEDCVGCKRCESACPT   60 #2

MSHTVKIYDTCIGCTQCVRACPTDVLEMVPWNGCKANQIASAPRTEDCVGCKRCESACPT   60 #3

MAHTVKIYDNCIGCTQCVRACPLDVLEMVPWDGCKAGQMASAPRTEDCVGCKRCETACPT   60 #4

*.*:*****:*************.********:****.*:*****************.****

DFLSVRVYLGSESTRSMGLSY   81 #1

DFLSVRVYLGSETTRSMGLAY   81 #2

DFLSVRVYLGAETTRSMGLAY   81 #3

DFLSIRVYLGGETTRSMGLAY   81 #4

```
HydA1_C.r.        --------------------------------AAPAAEAPLSHVQQALAELAKPKDDPTRKHV    31
HydA2_C.r.        ------------------------------AATATDAVPHWKLALEELDKPKDG-GRKVL    29
HydA_Chlorella_DT MCCPVVASRHAGRARHVAVRAAGPTSECDCPPTPQAKLPHWQQALDELAKPKE--SRRLM    58
                              |          ..:.  .  :.*.:...***:  .*:  .

HydA1_C.r.        CVQVAPAVRVAIAETLGLAPGATTPKQLAEGLRRLGFDEVFDTLFGADLTIMEEGSELLH    91
HydA2_C.r.        IAQVAPAVRVAIAESFGLAPGAVSPGKLATGLRALGFDQVFDTLFAADLTIMEEGTELLH    89
HydA_Chlorella_DT IAQIAPAVRVAIAETIGLAPGDVTIGQLVTGLRMLGFDYVFDTLFGADLTIMEEGTELLH   118
                  ..*:**********,,*****,,,,,,:*,,***.****.******,*********.****

HydA1_C.r.        RLTEHLEAHPHSDEPLPMFTSCCPGWIAMLEKSYPDLIPYVSSCKSPQMMLAAMVKSYLA   151
HydA2_C.r.        RLKEHLEAHPHSDEPLPMFTSCCPGWVAMMEKSYPELIPFVSSCKSPQMMMGAMVKTYLS   149
HydA_Chlorella_DT RLQDHLEQHPNKEEPLPMFTSCCPGWVAMVEKSNPELIPYLSSCKSPQMMLGAVIKNYYA   178
                  ** :***.**.,:*************:**.***.*:***::*********:.*::*.*..

HydA1_C.r.        EKKGIAPKDMVMVSIMPCTRKQSEADRDWFCVDADPTLRQLDHVITTVELGNIFKERGIN   211
HydA2_C.r.        EKQGIPAKDIVMVSVMPCVRKQGEADREWFCV-SEPGVRDVDHVITTAELGNIFKERGIN   208
HydA_Chlorella_DT QQVGVQPSDICNVSVMPCVRKQGEADREWFN--TTGLARDVDHVVTTAEVGKIFLERGIK   236
                  :: *: .,*:.,**:***.***.****:**,   . . *.:***.**.*:*.**.****.

HydA1_C.r.        LAELPEGEWDNPMGVGSGAGVLFGTTGGVMEAALRTAYELFTGTPLPRLSLSEVRGMDGI   271
HydA2_C.r.        LPELPDSDWDQPLGLGSGAGVLFGTTGGVMEAALRTAYEIVTKEPLPRLNLSEVRGLDGI   268
HydA_Chlorella_DT LNELPESNFDNPIGEGTGGALLFGTTGGVMEAALRTVYEVVTQKPMGRVDFEEVRGLEGI   296
                  * ***:.,,.*,*.* *.*.,:*************.**,,.*  *:.*:.:.,****::**

HydA1_C.r.        KETNITMVPAPGSKFEELLKHRAAARAEAAAHGTPG---------PLAWDGGAGFTSEDG   322
HydA2_C.r.        KEASVTLVPAPGSKFAELVAERLAHKVEEAAAAEAAAAVEGAVKPPIAYDGGQGFSTDDG   328
HydA_Chlorella_DT KEAEITLKPGDDSPF-----------------------------------KAFAGADG   319
                  **: :*:.*...*,*                                    .*.. **

HydA1_C.r.        RGGITLRVAVANGLGNAKKLITKMQAGEAKYDFVEIMACPAGCVGGGGQPRSTDKAITQK   382
HydA2_C.r.        KGGLKLRVAVANGLGNAKKLIGKMVSGEAKYDFVEIMACPAGCVGGGGQPRSTDKQITQK   388
HydA_Chlorella_DT Q-GITLKIAVANGLGNAKKLIKSLSEGKAKYDFIEVMACPGGCIGGGGQPRSTDKQILQK   378
                  , *:.*:*:***********  .:  *,*****:*:.****,**.***********.*,**

HydA1_C.r.        RQAALYNLDEKSTLRRSHENPSIRELYDTYLGEPLGHKAHELLHTHYVAGGVEEKDEKK   441
HydA2_C.r.        RQAALYDLDERNTLRRSHENEAVNQLYKEFLGEPLSHRAHELLHTHYVPGGAEADA---   444
HydA_Chlorella_DT RQQAMYNLDERSAIRRSHENPFIQALYDKFLGAPNSHKAHDLLHTHYVAGGIPEEK---   434
                  **,*:*:***::.::******. :. **. :**.*,,*:**:*******.**,,,,
```

PHOTOSYSTEM I-HYDROGENASE CHIMERAS FOR HYDROGEN PRODUCTION

CROSS-REFERENCE TO RELATED APPLICATIONS

This patent application is a divisional of U.S. application Ser. No. 17/565,684, filed Dec. 30, 2021, which claims the benefit of and priority to U.S. Patent Application No. 63/132,219, filed Dec. 30, 2020, each of which is incorporated herein by reference in its entirety.

STATEMENT REGARDING FEDERALLY SPONSORED RESEARCH OR DEVELOPMENT

This invention was made with government support under 1706960 and 2016666 awarded by the National Science Foundation. The government has certain rights in the invention.

SEQUENCE LISTING

This application is being filed electronically via Patent Center and includes an electronically submitted Sequence Listing in .xml format. The file contains a sequence listing entitled "112624.01452.xml" created on Jun. 12, 2024 and is 23,290 bytes in size. The Sequence Listing contained in this .xml file is part of the specification and is hereby incorporated by reference herein in its entirety.

BACKGROUND

Conversion of algal cells into solar-powered biofactories generating high-energy product molecules is a promising avenue for addressing the ever-increasing global energy demand, due to its environmental friendliness and cheap replication. Hydrogen ($H_2$) is an attractive target product for several reasons. It is an important commodity with over 60 million tons produced globally, but about 95% of it is produced from steam reformation of fossil fuels, thus contributing to the rise of atmospheric $CO_2$. The [FeFe] hydrogenase enzyme catalyzes the rapid and reversible reduction of protons. The active site of ($2H^+ + 2e^- \leftrightarrows H_2$) the enzyme is a metallic cofactor that is $O_2$-sensitive and must be inserted by maturation factors. These characteristics are shared with many important redox enzymes, making hydrogenase an ideal test case for synthetic biology manipulations.

In the thylakoid membranes of the chloroplast, the photosynthetic electron transport chain (PETC) performs light-driven electron transport from water to ferredoxin (Fd) and pumps protons across the membrane, ultimately providing metabolic energy (ATP) and low-potential reductant (NADPH) to drive $CO_2$ fixation by the Calvin-Benson-Bassham (CBB) cycle. Algal hydrogenases are particularly attractive as producers of a solar fuel due to their structural simplicity (e.g., a single catalytic domain) and ability to couple sunlight to hydrogen production by using reducing equivalents from the PETC. The active site of the enzyme consists of a [4Fe-4S] cluster coupled to a di-iron subsite containing CO and $CN^-$ ligands; insertion of the latter requires three maturase proteins. Algal hydrogenases normally function to dispose of excess reductant under anoxic conditions, to facilitate fermentative processes in the dark or the initiation of photosynthetic linear electron flow during dark-to-light transitions. Despite various attempts to improve hydrogen production in green algae, it has not yet become economically feasible. Accordingly, there remains a need in the art for efficient, scalable, and economically feasible methods of producing hydrogen in algae.

SUMMARY OF THE DISCLOSURE

Fusion proteins, genetically engineered cells and expression cassettes comprising polynucleotides encoding the fusion proteins are provided herein as well as methods of using the same. In one aspect, genetically engineered cells comprising a polynucleotide encoding a fusion protein comprising a photosystem I (PSI) protein and an algal hydrogenase are provided. The PSI protein may be a PsaC protein and the hydrogenase is an algal FeFe hydrogenase. The fusion protein has the hydrogenase inserted in the hinge region or β-hairpin of the PsaC protein.

In another aspect, expression cassettes comprising a polynucleotide encoding a fusion protein comprising a PSI protein and an algal hydrogenase are provided. The polynucleotide is optionally operably linked to a promoter that drives expression of the fusion protein.

In another aspect, a fusion protein comprising an algal FeFe hydrogenase inserted into the hinge region of PsaC of PSI is provided.

In another aspect, methods of producing the engineered cells, an algal biomass or the fusion protein are provided. The methods include expressing in an algal cell a polynucleotide encoding a fusion protein comprising a PSI protein and an algal hydrogenase as described herein.

In a still further aspect, methods of increasing hydrogen ($H_2$) production in a cell are provided. These methods include introducing into the cell the expression cassette or polynucleotide encoding the fusion protein described herein to produce a genetically engineered cell and then culturing the genetically engineered cells under saturating light conditions. The genetically engineered cells exhibit at least a 5-fold increase in $H_2$ production under such conditions relative to a control cell of the same species under the same conditions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

3

Figures 2A, 2B:
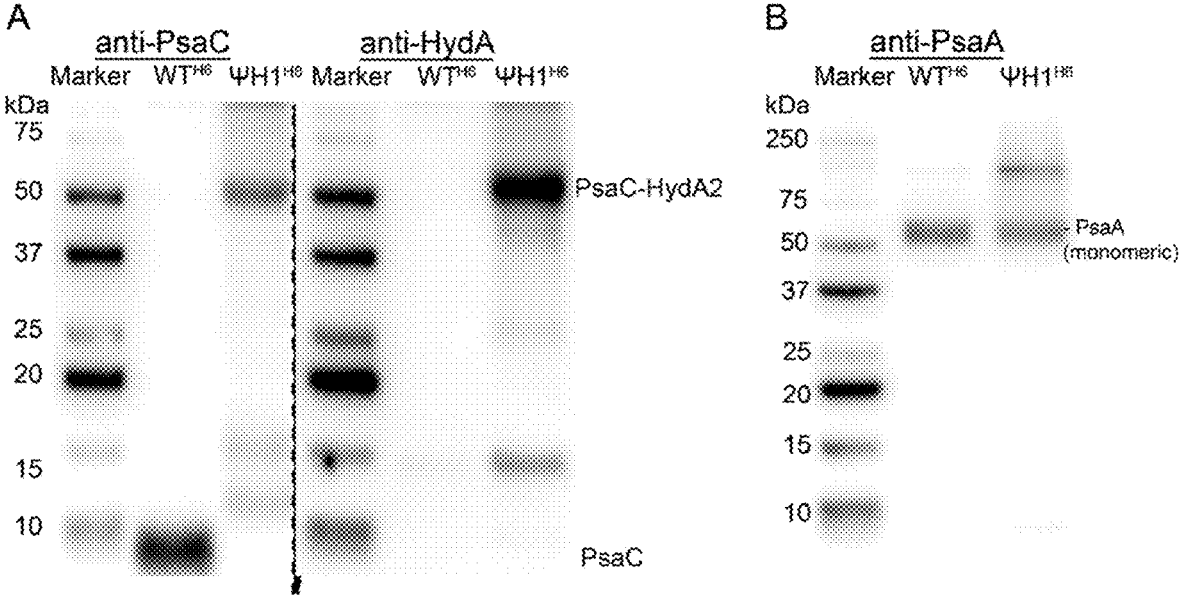

FIGS. 2A-2B present immunoblots of isolated PSI and PSI-HydA from WT$^{H6}$ or ψH1$^{H6}$, demonstrating assembly of PsaC-HydA2 into PSI-HydA. Equimolar amounts of PSI and PSI-HydA were probed with α-PsaC (A, left), α-HydA (A, right), or α-PsaA (B) antibodies. Sizes of marker polypeptides are indicated to the left. Integration of α-PsaA cross-reactive bands gave a ratio of 1.00:1.09 (WT:chimera).

Figures 3A, 3B:
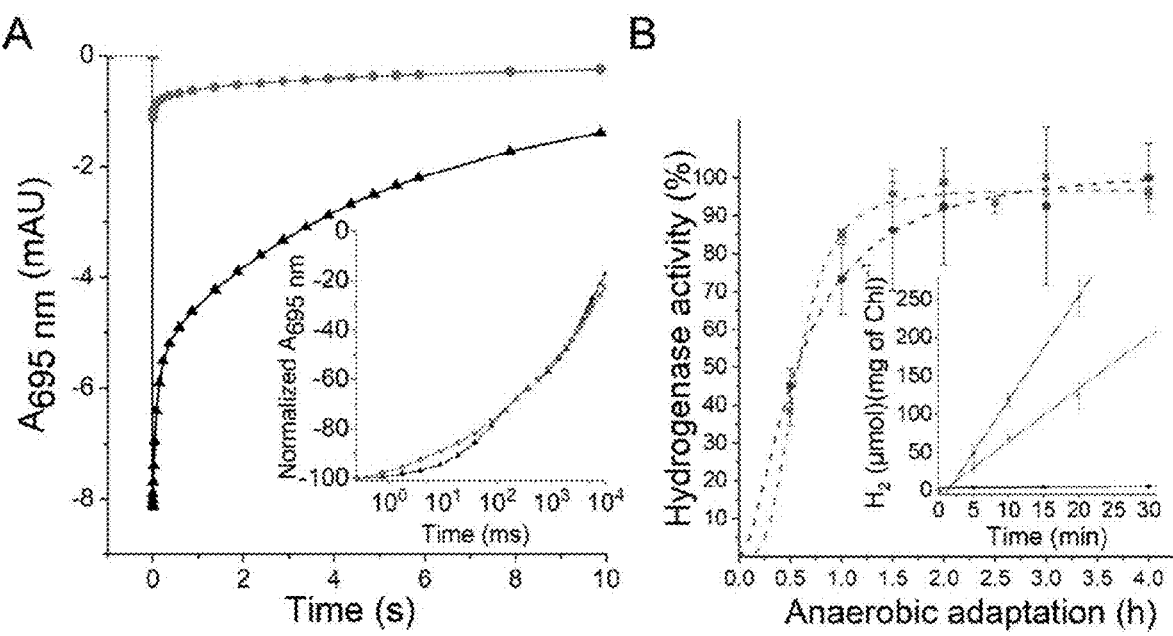

FIGS. 3A-3B present in vitro characterization of the PSI-hydrogenase chimera. (A) Transients of flash-induced P$_{700}$ photobleaching and recovery in thylakoid membranes (60 mg Chl) isolated from hydA (black triangles) and ψH1 (red circles) cells that had been grown aerobically. The inset displays transients normalized to the maximal bleaching and using a log time scale. (B) Hydrogenase activity (expressed as % of maximal activity attained) assayed with reduced MV on whole cells, as a function of the anaerobic adaptation period. Inset: In vitro H$_2$ production with dithionite/MV in detergent-permeabilized hydA (black), WT (blue), and ψH1 (red) cells after 1.5 h anaerobic induction. Error bars represent standard error (n=3).

Figures 4A, 4B:
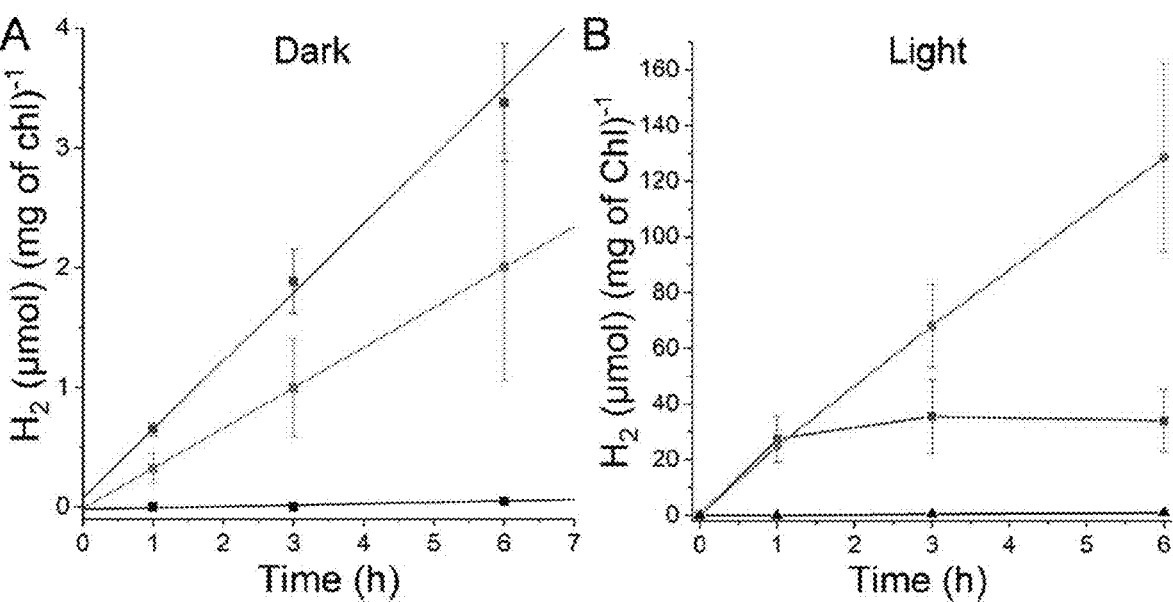

FIGS. 4A-4B present accumulated H$_2$ in the headspace of sealed bottles produced by WT (blue squares), hydA (black triangles), or ψH1 (red circles) cultures in dark (A) or light (B, 200 mmol photons m$^{-2}$ s$^{-1}$), as measured by GC-TCD (n=3). Values are normalized to the initial Chl content of the cultures. Please note the different scales.

FIGS. 5A-5D present membrane inlet mass spectrometry (MIMS) data. Rates of H$_2$ (A) or O$_2$ (B) production in cultures of WT (blue squares), hydA (black triangles), and ψH1 (red circles) under indicated light intensities in media containing acetate (solid symbols/lines) or lacking acetate (hollow symbols/dashed lines). Rates were determined as the slope of concentration change over 1 min of time. (C) Effect of enforced anoxia using glucose oxidase/catalase on H$_2$ evolution rate in an anaerobically adapted CH1 culture with acetate. Light-saturation data were fitted to a hyperbolic curve with V$_{max}$ (dotted line) ~120 mmol of H$_2$ h$^{-1}$ (mg of Chl)$^{-1}$. Error bars in (A)-(C) represent standard error of the mean (biological replicates, n=3). (D) Instantaneous H$_2$ production normalized to Chl under enforced anoxia of ψH1 (red) or WT (blue) cultures with (dashed lines) or without (solid lines) 60 mM glycolaldehyde under continuous 200 mmol m$^{-2}$ s$^{-1}$ red light (average of 3 biological replicates).

FIG. 6 is the coding sequence of the PsaC-HydA2 fusion polypeptide (SEQ ID NO: 1). Highlighted residues indicate the PsaC fragments (green), N-terminal junction (cyan), and C-terminal junction (red). The red highlighted Ala residue is shared between the HydA2 and PsaC sequences.

Figures 7A, 7B:
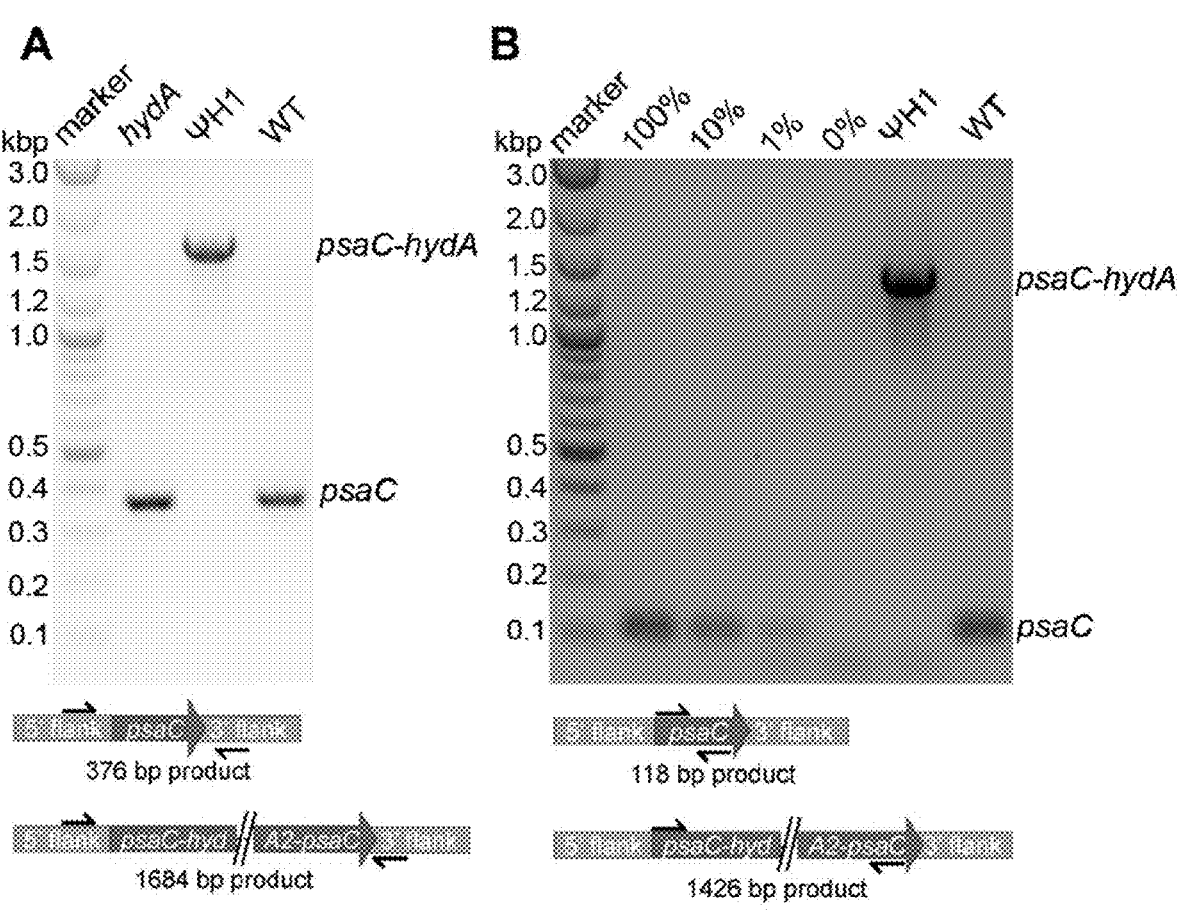

FIGS. 7A-7B show the agarose gel of PCR amplification of C. reinhardtii genomic DNA from parental (hydA), chimera-expressing (ΨH1) and WT strains with locus-specific (A) and gene-specific primers (B). A: psaC detection PCR with primers annealing to flanking sequences and corresponding cartoon showing primer locations and amplicon sizes using psaC or psaC-hydA2 as the template. B: Homoplasmy detection PCR with gene-specific primers and corresponding cartoon with primer locations and amplicon sizes. Percentages indicate the abundance of the wild type genomic DNA (containing psaC gene) that had been diluted into the genomic DNA of the psaCΔ strain at the same DNA concentration (i.e., total genomic DNA was kept at 100 ng/reaction). PCR amplicons were resolved on 1% agarose gel and stained with ethidium bromide. A 2-log DNA marker (NEB) was used for size approximation; sizes in kbp are indicated to the left of the gel images.

Figure 8:
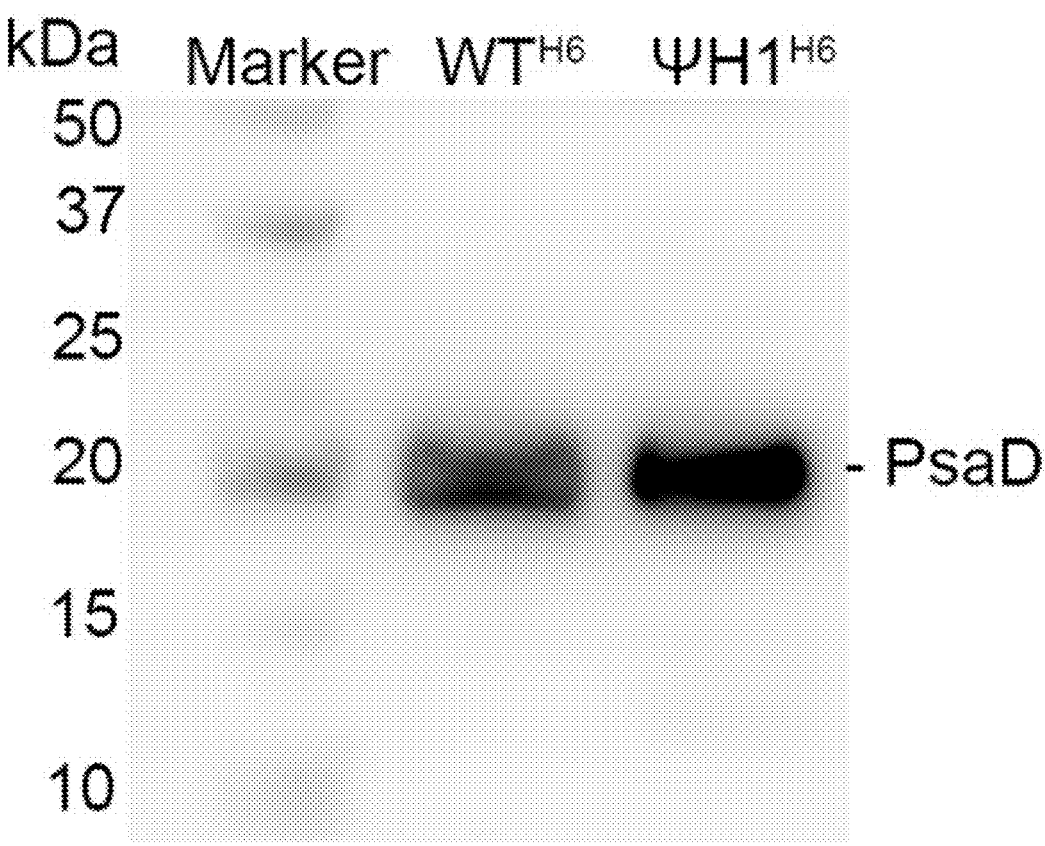

FIG. 8 shows an immunoblot of isolated PSI particles using anti-PsaD antibodies. Samples were loaded on equal

4

P$_{700}$, as in FIG. 2. Integration of the anti-PsaD cross-reactive bands gave a ratio of 1.00:1.02 (PSI:PSI-HydA).

Figures 9A, 9B:
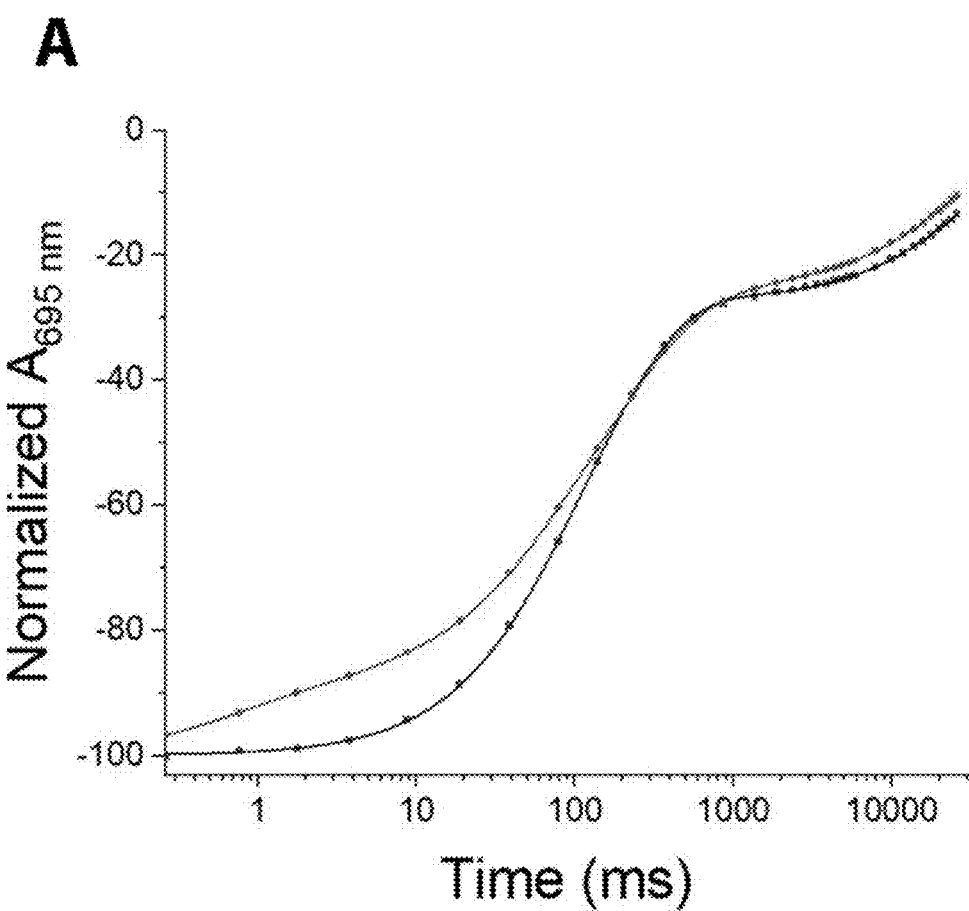

FIGS. 9A-9B present spectroscopic characterization of anoxically prepared PSI$^{H6}$ and PSI$^{H6}$-HydA2 particles that were loaded into a sealed cuvet in an anaerobic glovebox to eliminate O$_2$ from the environment. (A) Normalized transients (n=3, technical replicates) of P$_{700}^+$ recovery upon laser flash-induced bleaching in anoxically prepared PSI particles: WT$^{H6}$ (black, 74 fmol of P$_{700}^+$) and PSI$^{H6}$-HydA2 (red, 71 fmol of P$_{700}^+$). Solid lines represent fit to a multi-exponential decay, using the time constants and relative amplitudes reported in panel (B) CR=charge recombination, F$_H$=[4Fe-4S] cluster of HydA2 domain.

Figures 10A, 10B, 10C:
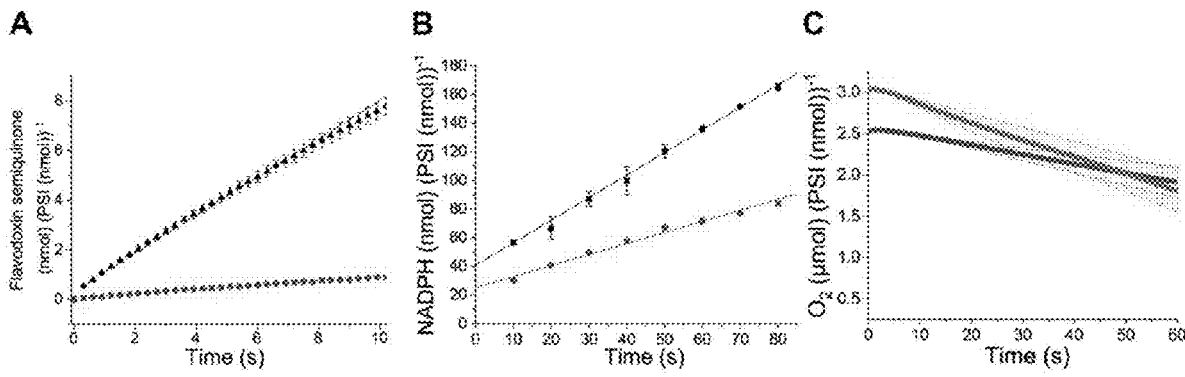

FIGS. 10A-10C present in vitro PSI activity measured by photoreduction of flavodoxin (A), NADP$^+$ (B) and O$_2$ (C). (A) Flavodoxin photoreduction with purified PSI [black=hydA (triangles), red=ΨH1 (circles)] (normalized to 1 nmol of PSI) under saturating light conditions. Turnover rates are 0.77 s$^{-1}$ (hydA) and 0.088 s$^{-1}$ (ΨH1). (B) Assays contained equal amounts of PSI (54 nM) [black=WT$^{H6}$ (squares), red=ΨH1$^{H6}$ (circles)] with an excess of ferredoxin (3 μM), FNR (0.2 μM), and NADP$^+$ (2.5 mM). Illumination (300 μmol of red photons m$^{-2}$ s$^{-1}$) of cuvette commenced at t=0. Lines represent a linear fit of the data. Rates thus obtained are 1.57±0.01 and 0.77±0.04 NADPH s$^{-1}$ per PSI for WT and PSI-HydA, respectively. (C) O$_2$ reduction rates measured with a Clark-type electrode. The O$_2$ uptake rates were normalized to the amount of P$_{700}$. Maximal light-dependent rates were 12.7±1.6 and 26.4±4.8 O$_2$ s$^{-1}$ per PSI for WT and PSI-HydA, respectively. Error bars represent SE (n=3).

Figure 11:
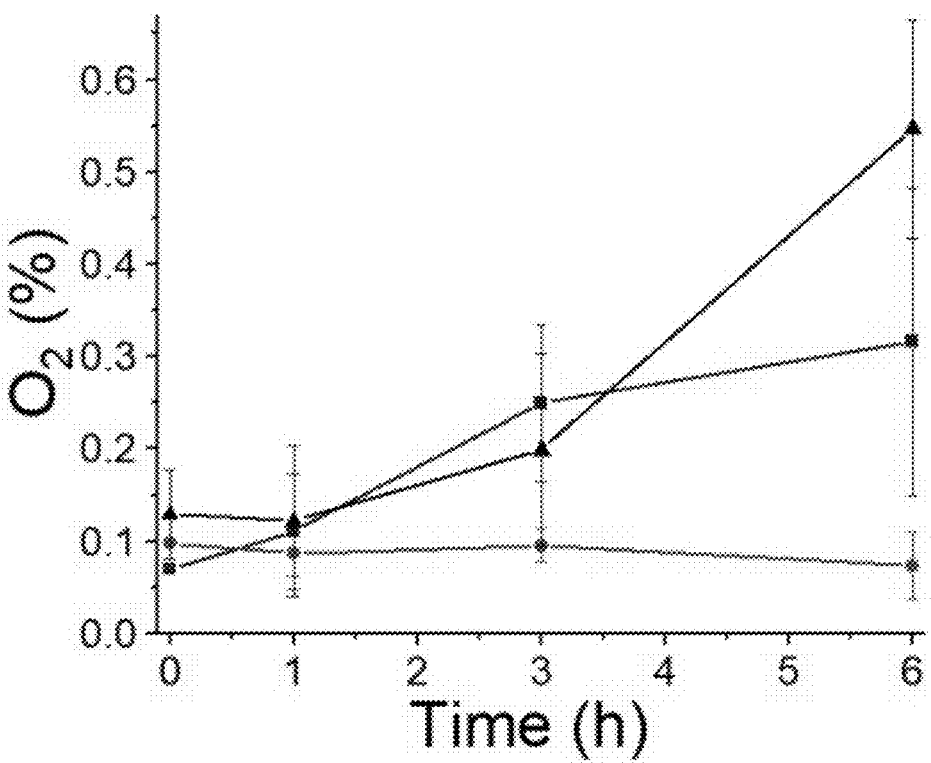

FIG. 11 presents accumulation of O$_2$, as measured by GC-TCD, in the headspace of sealed bottles containing cultures of WT (blue squares), hydA (black triangles), and ΨH1 (red circles). Illumination intensity was 200 μmol photons m$-2$ s$-1$. Experiment is the same one as shown in FIG. 4B.

Figures 12A, 12B, 12C:
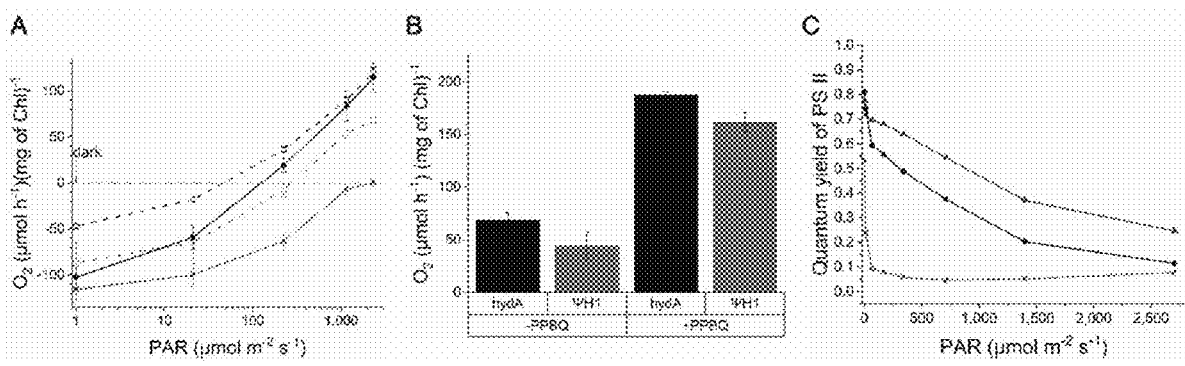

FIGS. 12A-12C present rates of dissolved O$_2$ consumption/production and quantum yield of PSII. (A) Net O$_2$ production rates under red LED illumination in aerobic cultures of hydA (black, circles) or ΨH1 (red, squares) in media with (solid lines and symbols) or without (dashed lines, hollow symbols) acetate. Data at 1 PAR correspond to the dark sample for graphing purpose. (B) Light-dependent O$_2$ evolution rates under ~2300 μmol m$^{-2}$ s$^{-1}$ of red light in cultures containing bicarbonate, with or without addition of 0.2 mM PPBQ. In all instances, cells were grown in medium containing acetate and then resuspended in fresh medium containing bicarbonate instead of acetate as a carbon source before being placed into the measuring cuvette. Cells were stirred and occasionally bubbled with air to maintain them in an aerobic state before dissolved O$_2$ was measured with an optical sensor. Error bars represent standard error (n=3). (C) Quantum yield of PSII in WT (blue triangle), hydA (black circle) and ΨH1 (red square) strains under various illumination intensities. Cells were aerobically resuspended in 20% Ficoll buffer (Tris-phosphate, pH 7.0) and kept aerobic throughout the experiment.

Figures 13A, 13B:
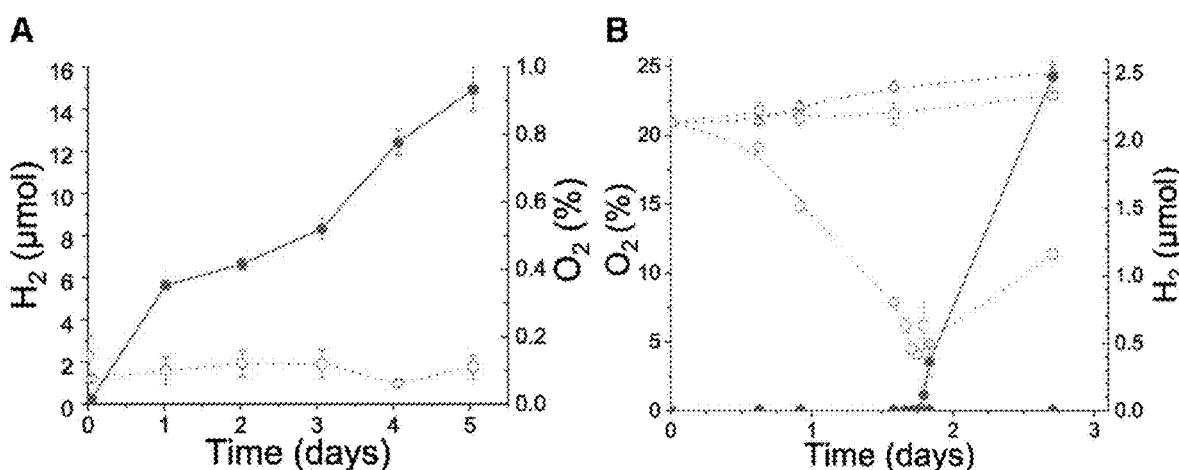

FIGS. 13A-13B present long-term measurements of H$_2$ (solid symbols and lines) and O$_2$ (hollow symbols, dotted lines) produced by 10-mL cultures in sealed 25-mL bottles with (A) or without (B) prior imposition of anoxia via argon-sparging. ΨH1 (red circles), hydA (black triangles) or WT (blue squares) cultures resuspended at ~1 μg/mL of Chl in fresh TAP were exposed to white light (~200 μmol m$^{-2}$ s$^{-1}$ PAR) and the headspace (15 mL) was sampled at the indicated times, followed by analysis via GC-TCD. Error bars represent SE (n=3).

Figure 14:
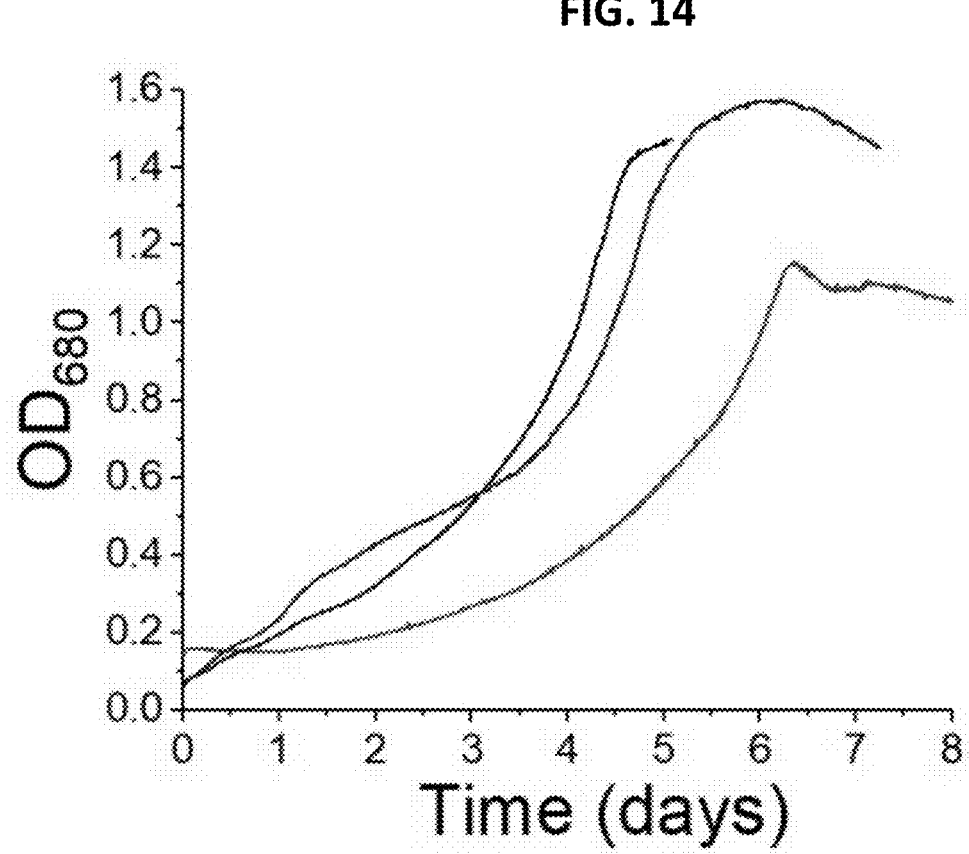

FIG. 14 presents photoautotrophic growth of hydA (black), WT (blue), and ΨH1 (red) cultures in a closed photobioreactor in TBP medium containing bicarbonate as the sole carbon source. Growth was monitored at 680 nm. The cultures were sparged in the dark with N$_2$ for 1 h prior to growth under illumination (340 μmol photons m$^{-2}$ s$^{-1}$).

Figure 15:
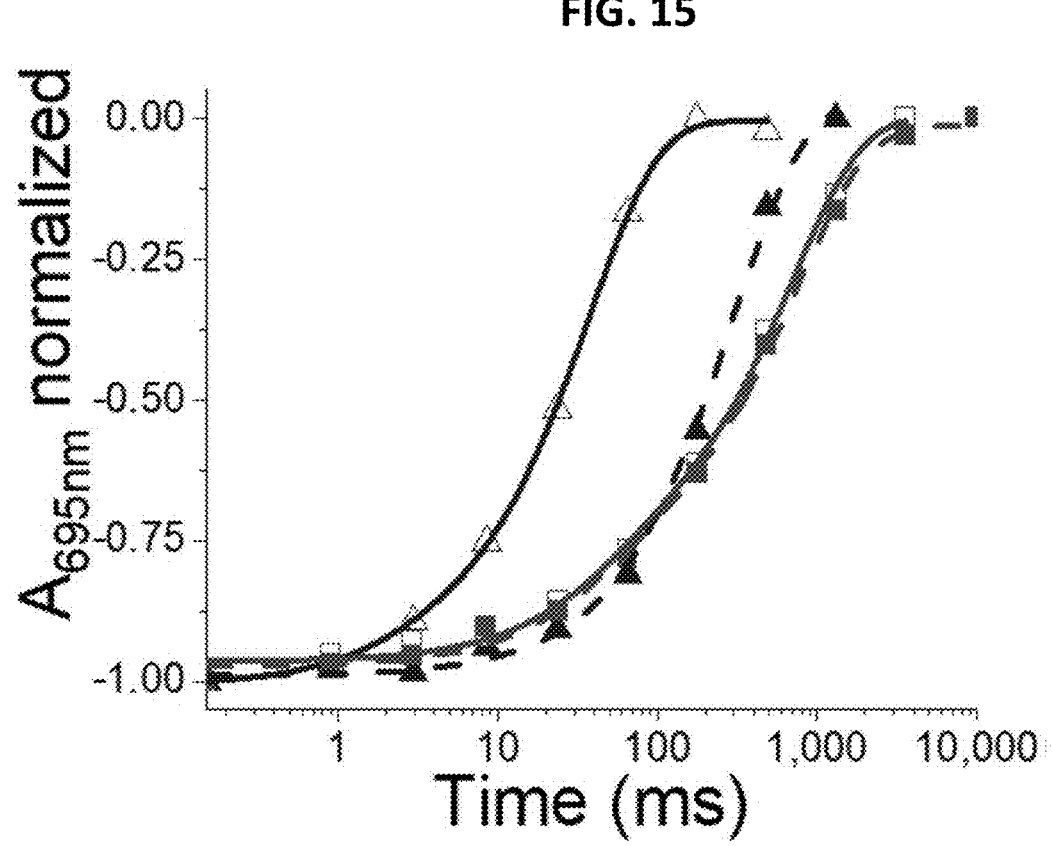

FIG. 15 presents cyclic electron flow measured in WT and ΨH1 cells. Normalized P$_{700}^+$ decay transients after 10 s of strong illumination (940 μmol photons m$^{-2}$ s$^{-1}$) in fully aerobic cultures of WT (blue triangles) and ΨH1 (red squares), to which had been added 20 μM DCMU (empty symbol/solid line), or 20 μM DCMU+20 μM 2,5-dibromo-3-methyl-6-isopropylbenzoquinone (DBMIB; filled symbol/dashed line). The level of P$_{700}$ photobleaching is normalized to the maximal level and is plotted on a log time scale. Note that the rate of P$_{700}^+$ reduction in the absence of PSII (with DCMU) is much slower in ΨH1 than in the WT cells and is unaffected by inhibition of cytochrome b$_6$f (with DBMIB), unlike the WT cells. Taken together, this indicates that cyclic electron flow is negligible in ΨH1 cells.

Figure 16:
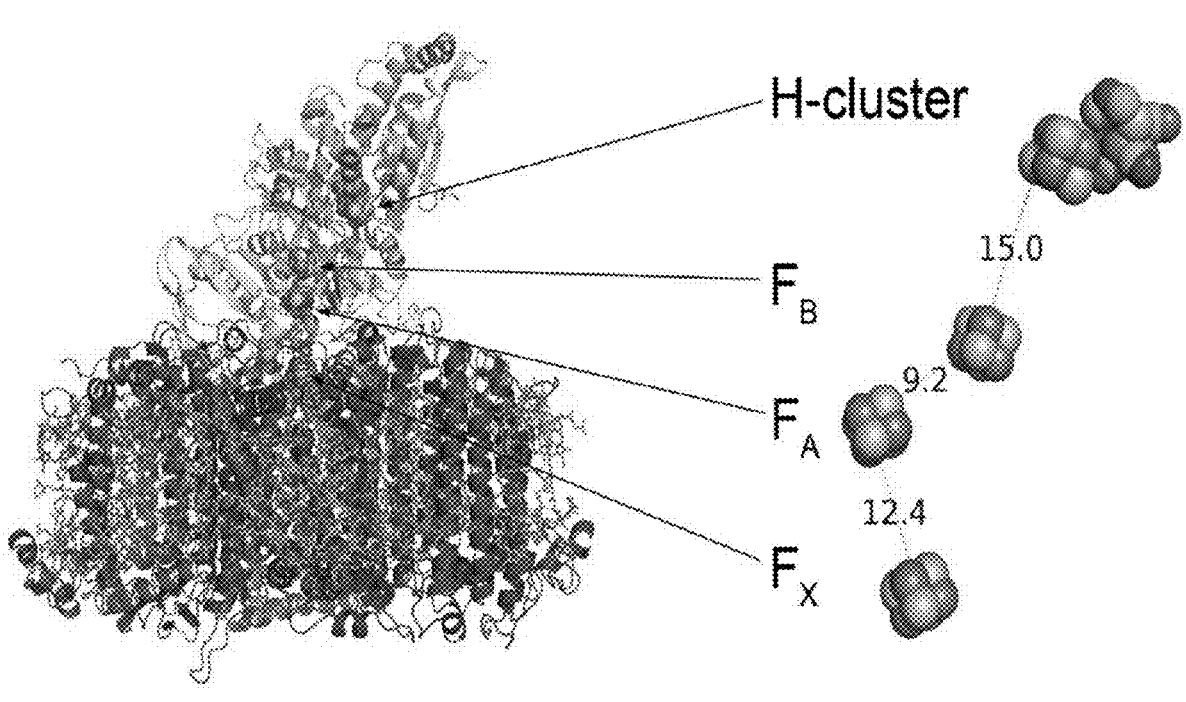

FIG. 16 presents a model of PSI-HydA1. PsaA (red), PsaB (blue), PsaC-HydA1 (cyan), PsaD (yellow), PsaF (orange)—are shown as cartoon representation, pigments—as green sticks, iron-sulfur clusters and H-cluster—as space-filling models. On the right iron sulfur clusters and H-cluster are magnified showing edge-to-edge distances in Å.

Figures 17A, 17B:
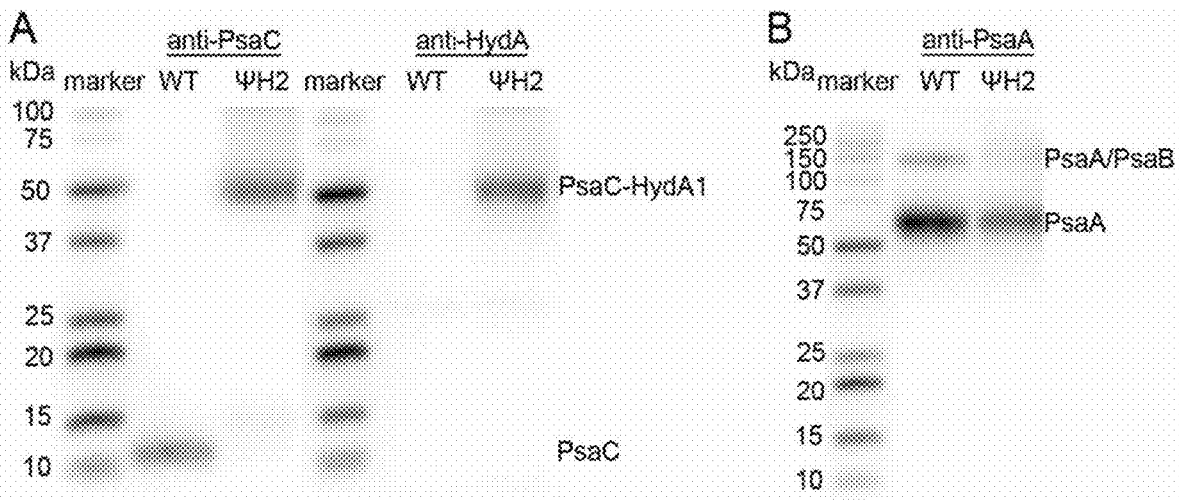

FIGS. 17A-17B shows immunoblots of solubilized thylakoid membranes, loaded based on equal amounts of P$_{700}$ (1.41 pmol) (A) or chlorophyll (2 μg) (B). Blots were probed with antibodies against PsaC (A, left), HydA (A, right), or PsaA (B).

Figures 18A, 18B:
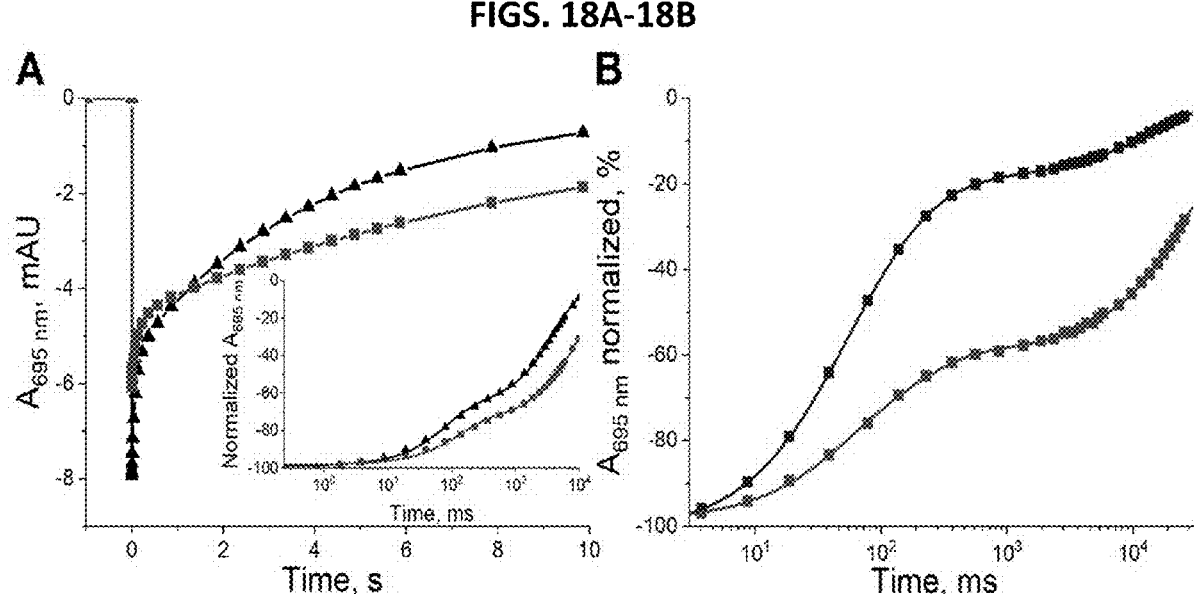

FIGS. 18A-18B present in vitro spectroscopic characterization of PSI-HydA1 chimera. (A) Transients of flash-induced P$_{700}$ photobleaching and recovery in thylakoids (normalized to 60 μg/mL of total Chl) isolated from hydA (black triangles) and ΨH2 (red squares) cells grown aerobically. The inset shows the same transients normalized to the maximal bleaching on a log time scale. (B) Transients of flash-induced P$_{700}$ photobleaching and recovery in purified PSI-HydA1 particles prepared oxically (red squares) or anoxically (blue squares) on anaerobically adapted cells.

Figure 19:
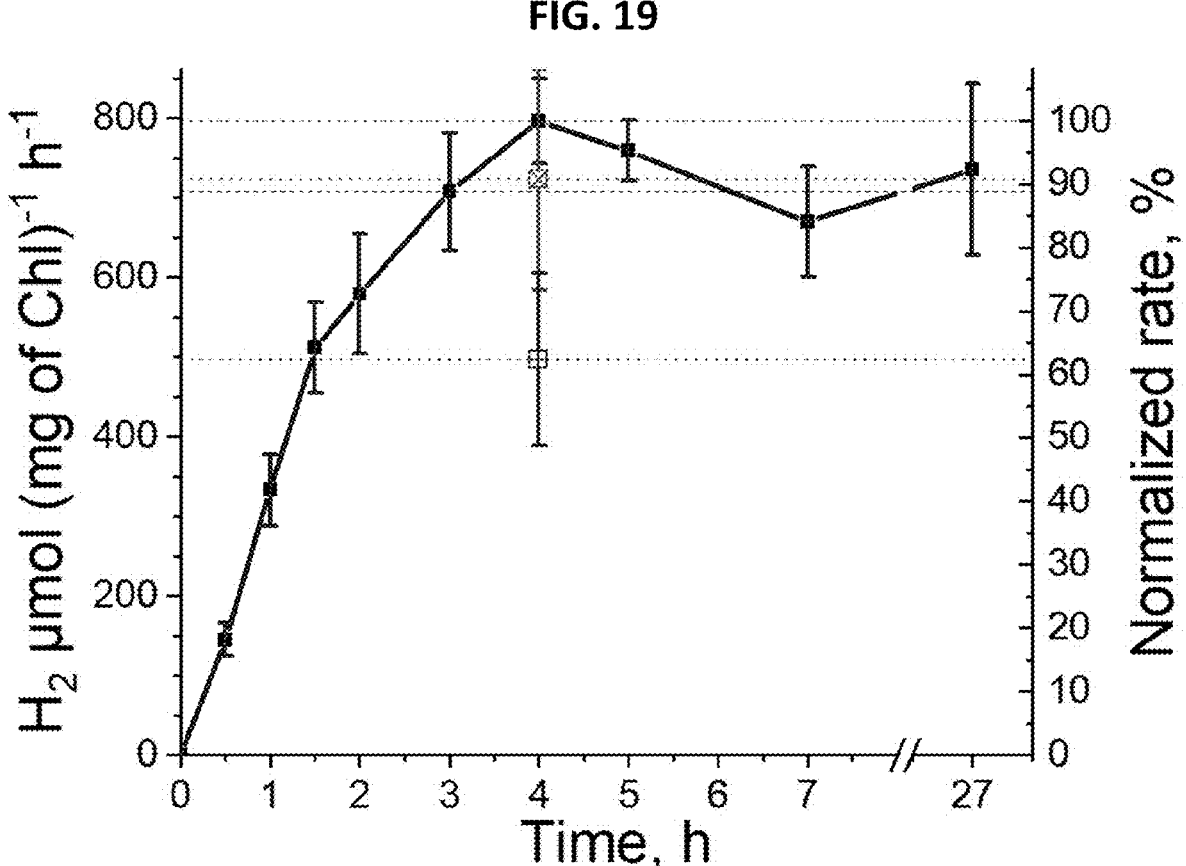

FIG. 19 presents absolute and normalized rates of H$_2$ production in reduced methyl viologen assay on whole cells (ΨH2 in TAP) as a function of anaerobic adaptation period. Black squares (solid) show untreated cells, red square (x)—with 200 μg/mL CAM added at the onset of anaerobic induction, blue square (+) represent a subset of untreated cells that went through 4 h of anaerobic adaptation followed by addition of 200 μg/mL CAM, 5 min air sparging, and another 4 h of anaerobic adaptation. Horizontal dashed/dotted lines help visualize relevant rates on absolute and relative scales. Error bars represent standard error (n≥3).

FIGS. 20A-20B present net headspace hydrogen (A) and oxygen (B) produced by ΨH2 in sealed bottles. The light and media conditions are indicated as follows: black (TAP+200 μmol m$^{-2}$ s$^{-1}$), blue (TAP+dark), red (TP+200 μmol m$^{-2}$ s$^{-1}$), green (TP+200 μmol m$^{-2}$ s$^{-1}$+10 μM DCMU). All values are normalized to Chl. Error bars indicate standard error (n=3 for all except the dark sample for which n=6).

Figures 21A, 21B, 21C:
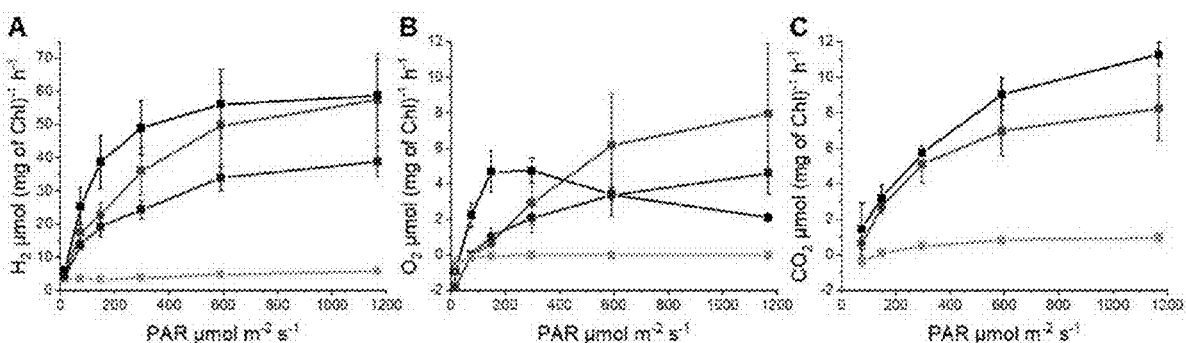

FIGS. 21A-21C present light-induced net maximal production rates of H$_2$ (A), O$_2$ (B) and CO$_2$ (C) in ΨH2 cell culture as measured by membrane inlet mass spectrometry (MIMS) during 2-min illumination periods at the indicated flux. The conditions are indicated as follows: black (TAP), red (TP), green (TP+10 μM DCMU), blue (TP+2 mM bicarbonate). Error bars represent standard error (n=3), except for the TP sample (n=5).

FIGS. 22A-22D present H$_2$ (black), O$_2$ (red), and CO$_2$ (blue) rate averages (n=3) during prolonged illumination (30 min) followed by 2 minutes of darkness on ΨH2 cells resuspended in TP (A), D66 WT in TP (B), ΨH2 in TP+2 mM bicarbonate (C), ΨH2 in TP+2 mM bicarbonate+40 mM glycol aldehyde (GA, D). Error bars are not shown for clarity.

Figures 23A, 23B:
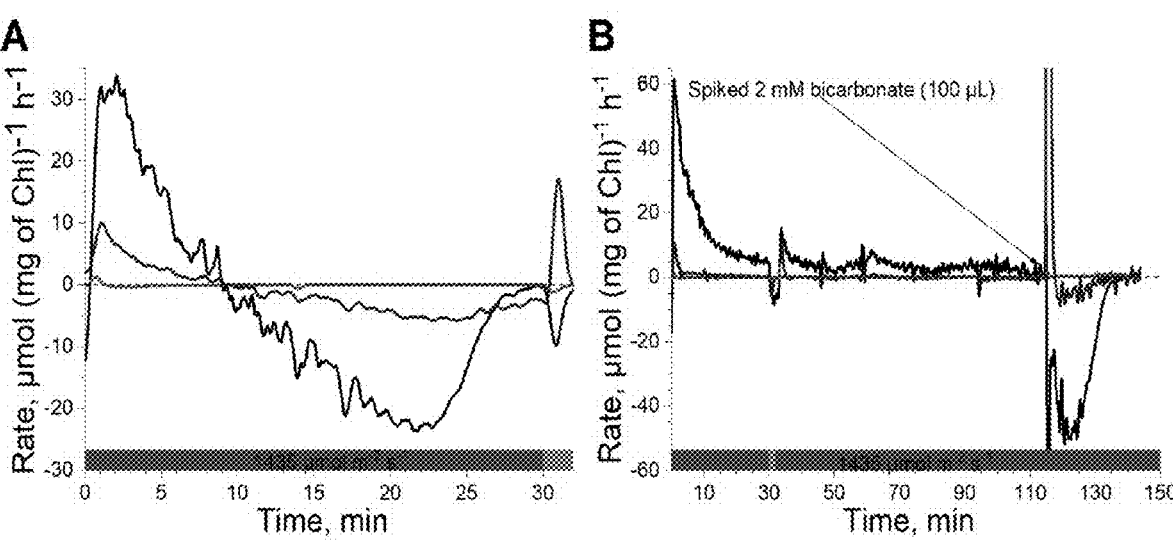

FIGS. 23A-23B present variability in the metabolic switch onset for rates of H$_2$ (black), O$_2$ (red), and CO$_2$ (blue) generated by ΨH2 cells resuspended in TAP (acetate). In panel A, a typical light regimen resulted in H$_2$ uptake after 10 min while in panel (B) an extended illumination and addition of bicarbonate were required for onset of H$_2$ uptake.

FIG. 24 presents coding sequence of the PsaC-HydA1 polypeptide (SEQ ID NO: 2). Highlighted residues indicate the PsaC fragments (green), N-terminal junction (cyan), borrowed linker sequence from PsaC-HydA2 chimera (magenta), and C-terminal junction (red).

FIG. 25 presents pairwise sequence alignment (EMBOSS needle) of mature HydA1 (SEQ ID NO: 3) and HydA2 (SEQ ID NO: 4) polypeptides. (I) shows identical, colon (:)—similar, and dot (•)—non-similar aligned residues. Non-conserved N-(blue) and C-(red) terminal sequences are highlighted. Red frame with 1 on top indicates the first and the last conserved residue among algal: *Chlamydomonas reinhardtii* (HydA1, HydA2), *Scenedesmus obliquus* (HydA1, HydA2) as well as the bacterial *Clostridium pasteurianum* (Cp.H1) hydrogenases, while 2 marks the last conserved residue among the algal hydrogenases as shown by Forestier et al. 2003.

FIG. 26 presents Clustal alignment of PsaC-HydA2 (SEQ ID NO: 1) chimera vs PsaCHydA1 (SEQ ID NO: 2). Star (*) represents identical residues, dot (•) similar residues and space ( )—not similar residues. Green highlights original PsaC sequence. Blue and red boxes show N- and C-terminal linking sequences with respect to hydrogenase domain orientation.

Figure 27:
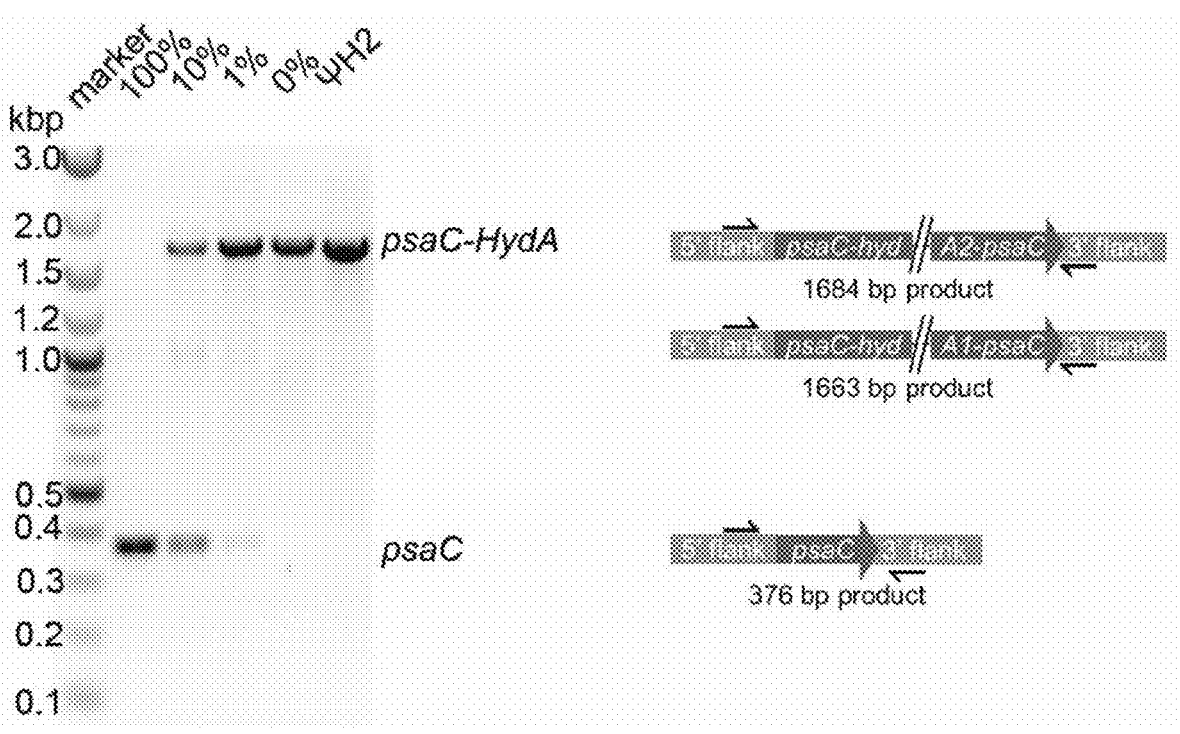

FIG. 27 is an agarose gel image of homoplasmicity detection PCR. Wild type genomic DNA (parental strain) indicated as a percentage of total DNA (diluted in ΨH1 genomic DNA containing psaC-HydA2). Total DNA was kept at 100 ng per reaction.

Figure 28:
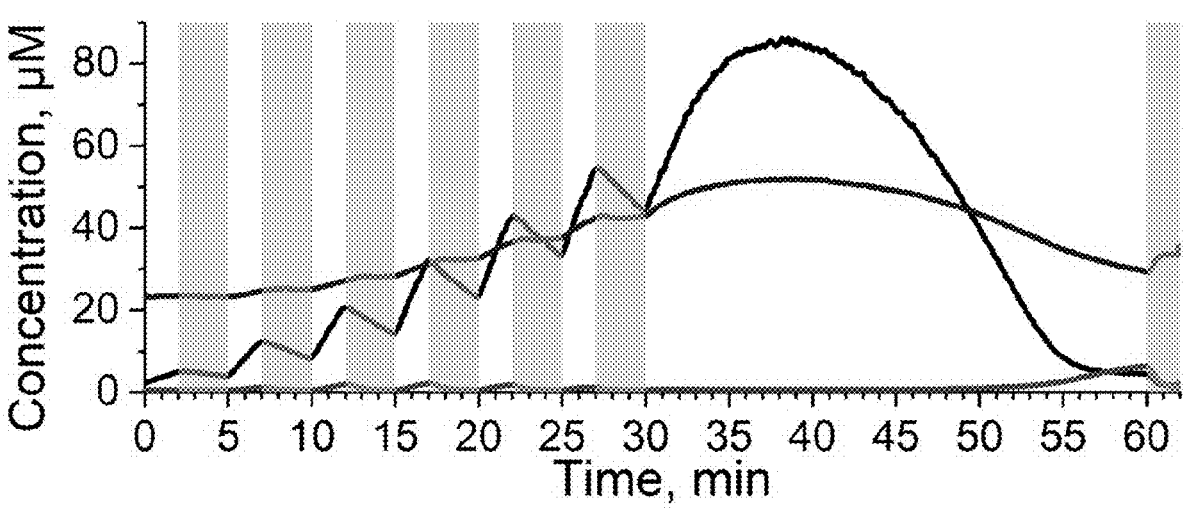

FIG. 28 presents concentration of dissolved gases—H$_2$ (black), O$_2$ (red), and CO$_2$ (blue) in a prototypical light sequence used for MIMS experiments on ΨH2 cells (suspended in TAP). A sample experiment is shown with greyed areas indicating periods of darkness. For clarity, light saturation portion of the experiment (first 30 min) will be presented separately from the prolonged illumination (30-60 min).

Figure 29:
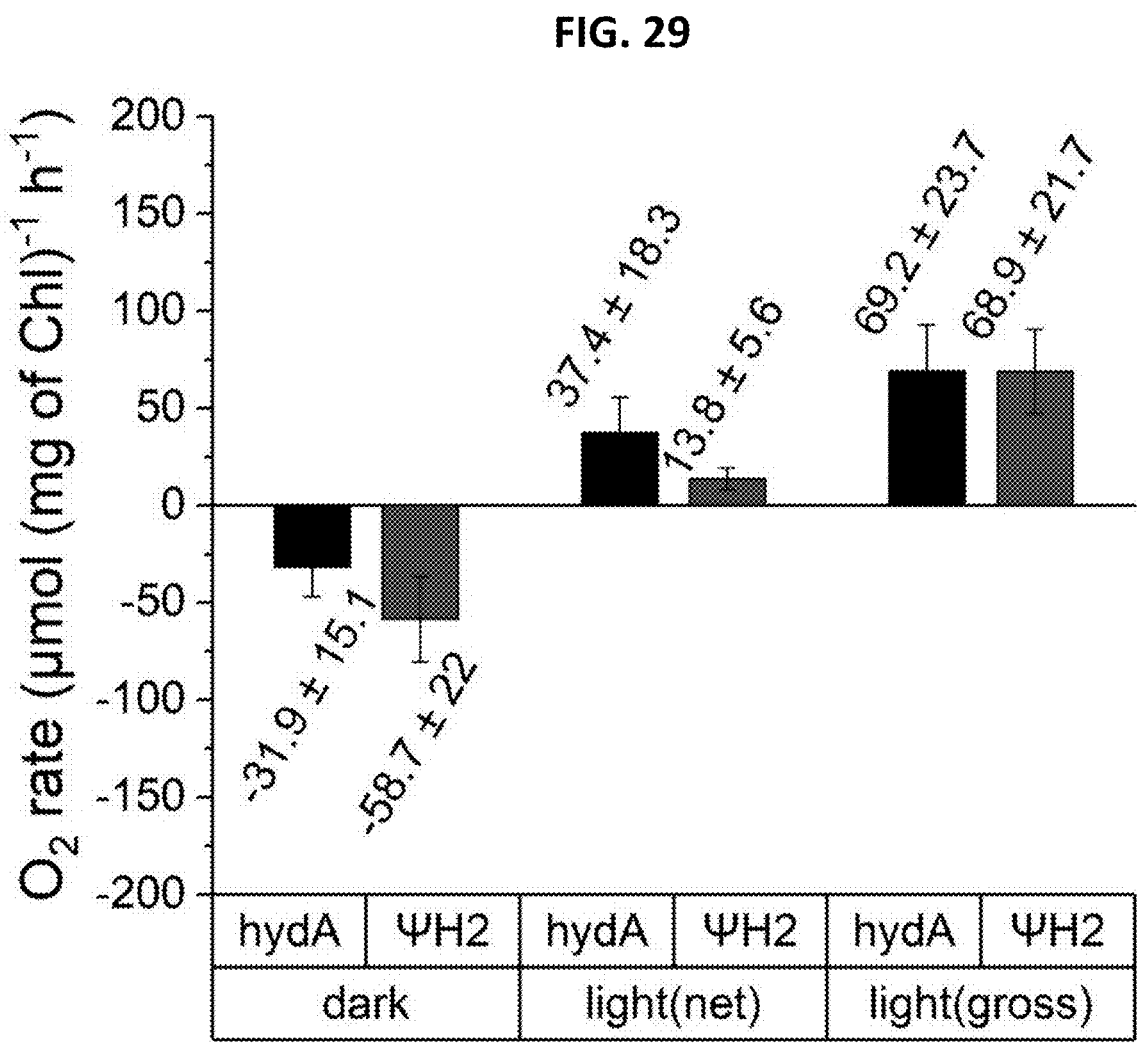

FIG. 29 is a graph showing the oxygen rate in cultures resuspended in TAP+25 mM bicarbonate as measured by FireSting-O$_2$ optical meter. Light condition corresponds to 1435 μmol m$^{-2}$ s$^{-1}$ PAR (red). Error bars represent standard error (n=3 for hydA and n=6 for ΨH2).

FIGS. 30A-30D are a set of graphs showing the concentration of dissolved gases—H$_2$ (black), O$_2$ (red), and CO$_2$ (blue), that were used to derive rates in FIG. 22. Cells of ΨH2 in TP (A), D66 in TP (B), ΨH2 in TP+2 mM bicarbonate (C) or ΨH2 in TP+2 mM bicarbonate+40 mM GA (D) were exposed to continuous illumination of red light (1435 μmol m$^{-2}$ s$^{-1}$) followed up by 2 min of darkness (shown as greyed rectangle). Dashed lines indicate the boundaries of standard error (n=3 for all, but panel A where n=5).

Figures 31A, 31B:
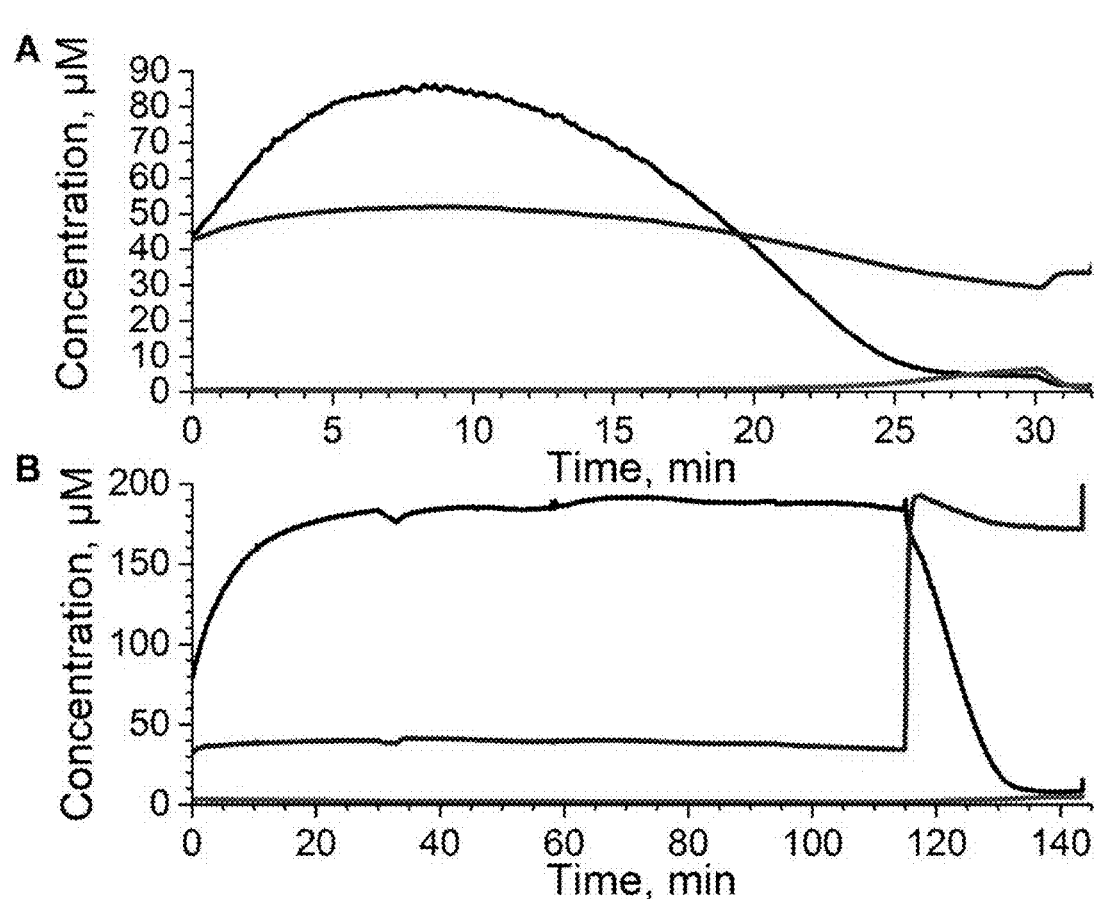

FIGS. 31A-31B present concentration of dissolved gases that were used to derive rates in FIG. 23: $H_2$ (black), $O_2$ (red) and $CO_2$ (blue). Individual runs are shown. (A) regular regimen or (B) extended illumination with the spike of bicarbonate in the end.

Figure 32:
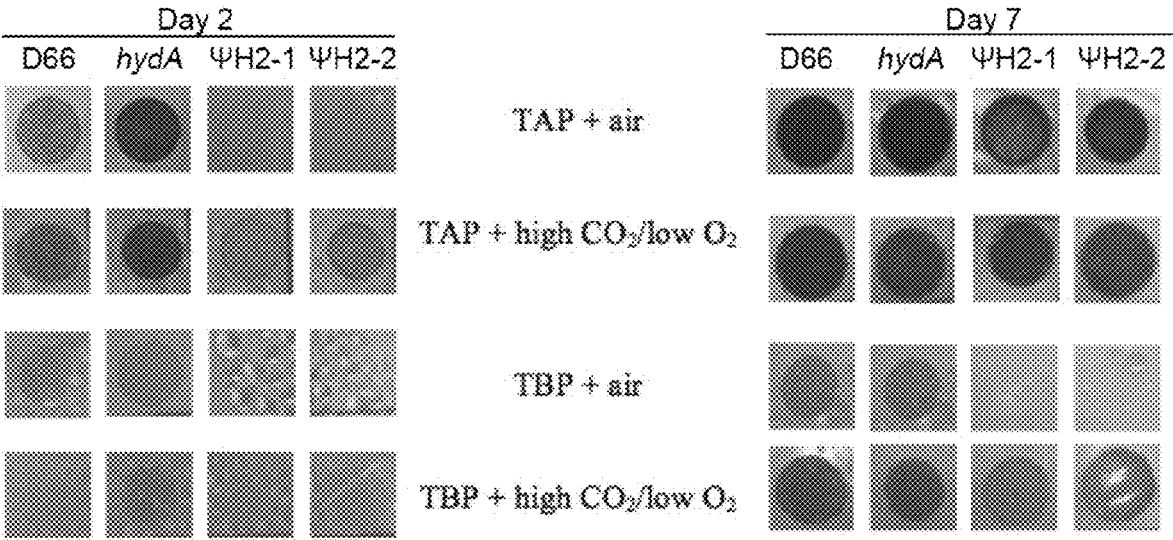

FIG. 32 presents growth assay on plates under 70 μmol $m^{-2}s^{-1}$ of white fluorescent light. Columns are marked on top with the corresponding algal strain. Rows differentiate between different media conditions.

Figure 33:
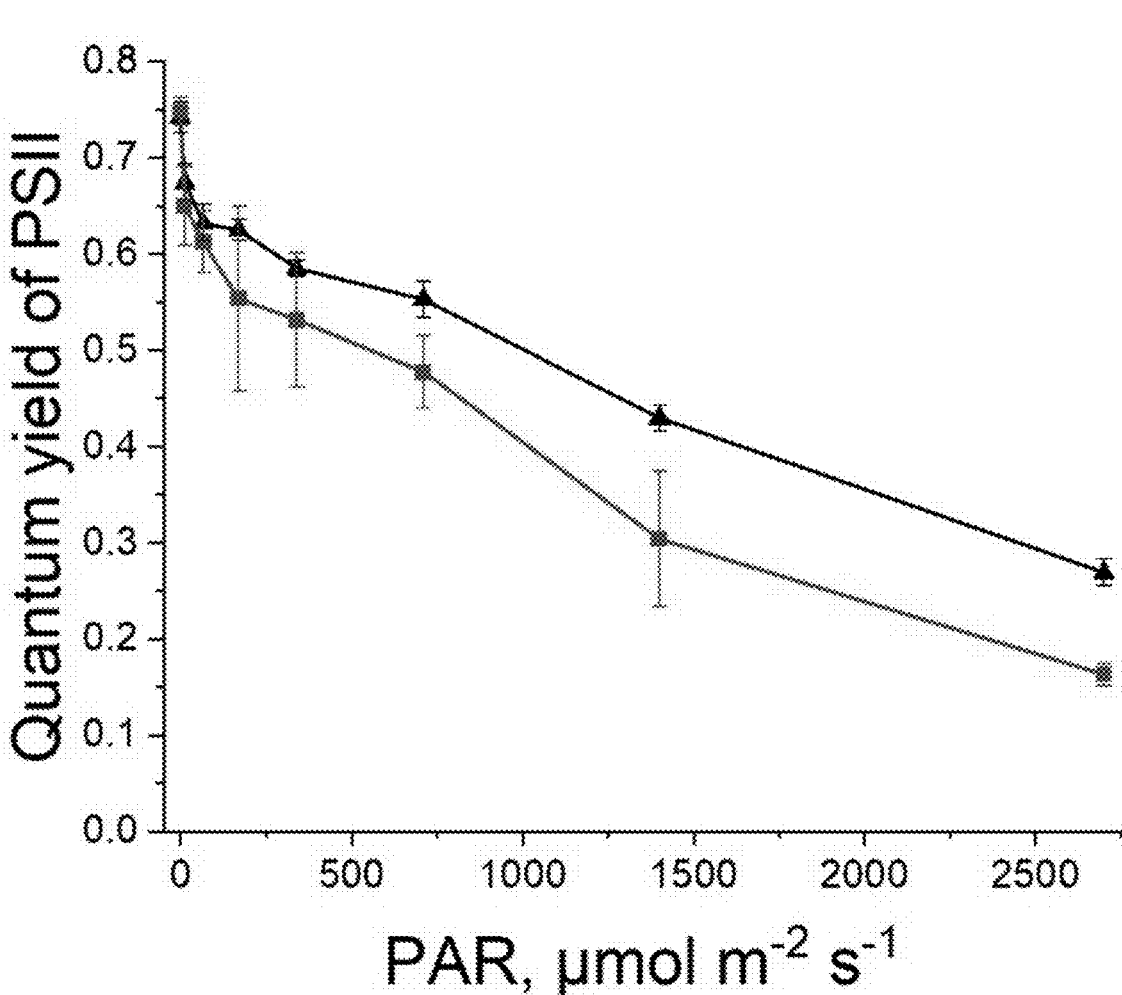

FIG. 33 presents quantum yield of PSII for hydA (black/triangle) and ΨH2 (red/square). Aerobically maintained cells were dark adapted for 5 min in sodium phosphate buffer (pH 7.0) with 20% Ficoll and 2 mM sodium bicarbonate. Error bars represent standard error (n=3).

Figure 34:
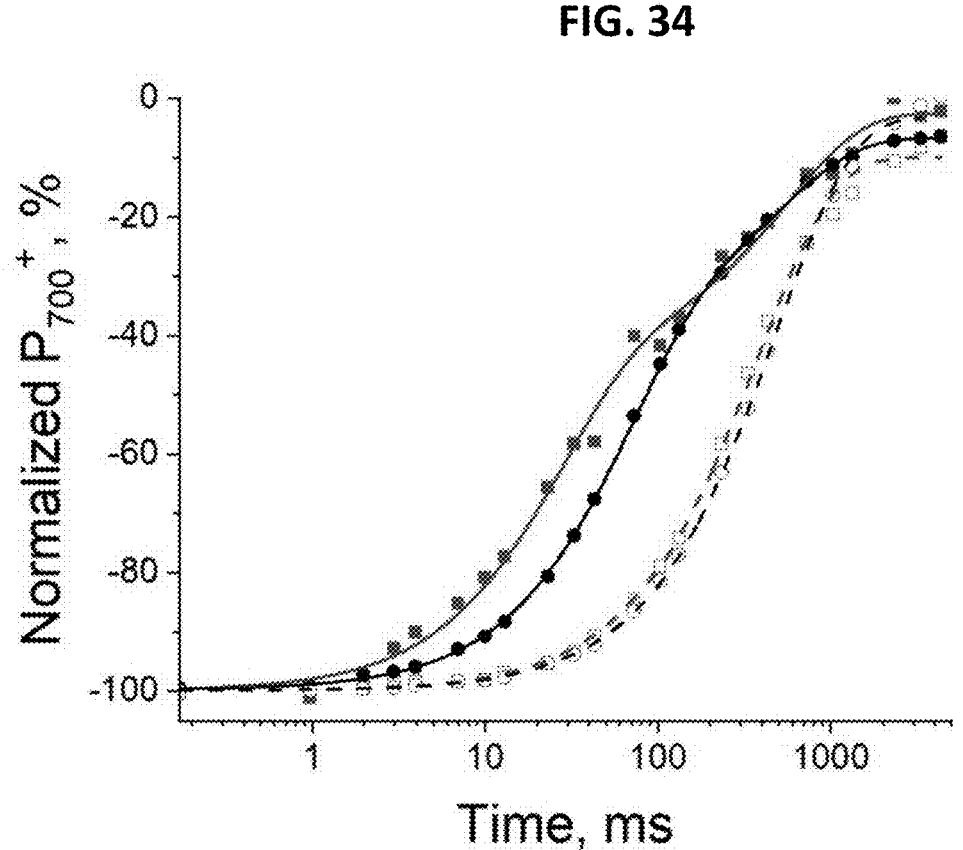

FIG. 34 presents $P_{700}^+$ dark recovery kinetics in whole cells after 10 s of illumination with red light (630 nm) at approximate flux of 500 photons $PSI^{-1}$ $s^{-1}$. ΨH2 with 10 μM DCMU (red squares) and D66 with 10 μM DCMU (black circles) transient averages (n=5) were fitted to biexponential decay (line). Addition of 20 μM DBMIB to the same cells is indicated by hollow symbols and the transients are fitted to a mono-exponential decay (dashed line).

Figure 35:
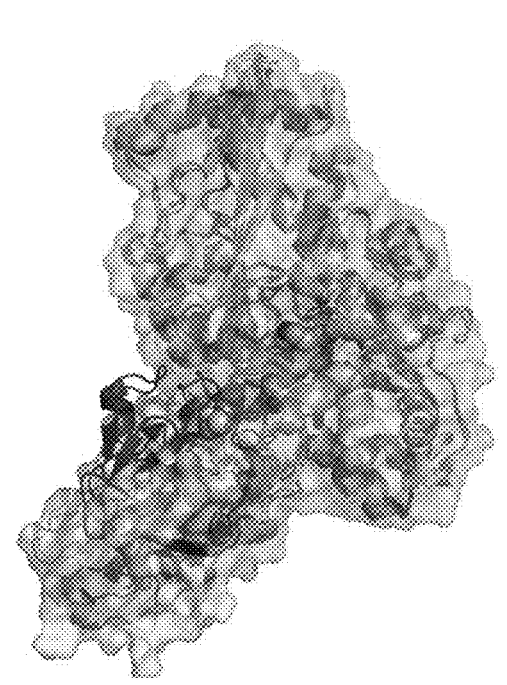

FIG. 35 presents superposition of ferredoxin 1 (purple cartoon) binding to HydA1 as shown in 2n0s and PsaC-HydA1 chimera (cyan cartoon and surface area) with PsaD (yellow cartoon and surface area). Hydrogenase domains were aligned in Pymol. HydA1 of 2n0s is hidden from the view.

Figure 36:
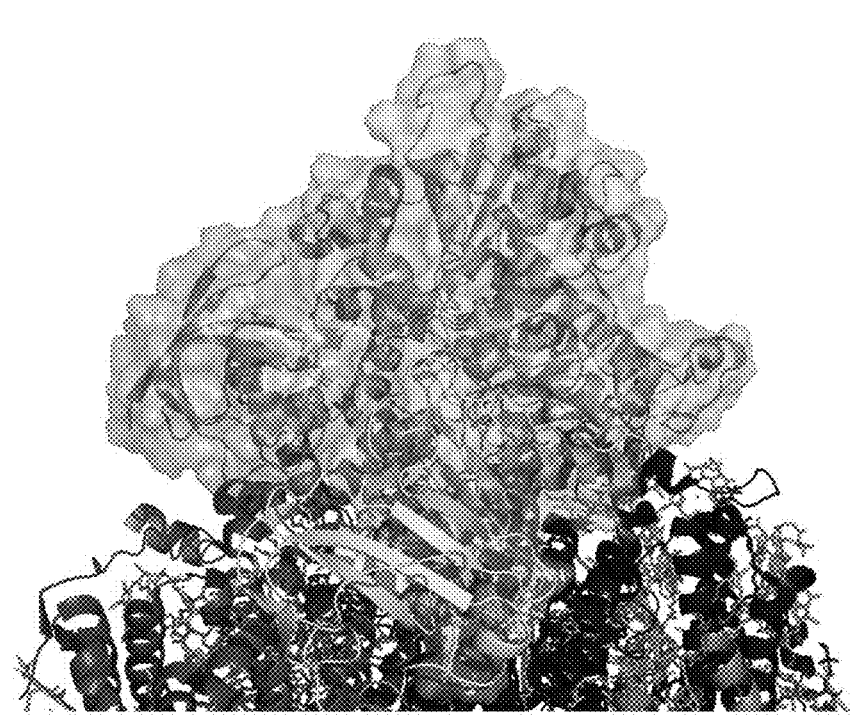

FIG. 36 presents superposition of ferredoxin 1 (rose cartoon and surface area) binding to PsaC/PsaD (yellow cartoon)/PsaE as shown in Cashman et al. and PsaC-HydA1 chimera (cyan cartoon and surface area), PsaA (red), and PsaB (blue). PsaC domains were aligned in Pymol. PsaD and PsaE are hidden from the view.

FIG. 37 presents alignment of algal PsaC polypeptide sequences. Alignment order is #1 (SEQ ID NO: 5) PsaC_*Chlamydomonas reinhardtii*, #2 (SEQ ID NO: 6) PsaC_*Chlorella vulgaris*, #3 (SEQ ID NO: 7) PsaC_*Picochlorum soloecismus*, #4 (SEQ ID NO: 8) PsaC_*Cyanidioschyzon merolae*. Star (*) represents identical residues, colon (:) similar residues and dot (•) not similar residues. β-hairpin is donated by | | and represent the site of insertion of the hydrogenase.

FIG. 38 shows the alignment of the hydrogenases of *Chlamydomonas reinhardtii* HydA1 (SEQ ID NO: 3), *Chlamydomonas reinhardtii* HydA2 (SEQ ID NO: 4) and *Chlorella* HydA (SEQ ID NO: 9).

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

The compositions and methods described herein are based, at least in part, on the inventor's development of a fusion of photosystem I (PSI) and an iron-iron hydrogenase, created by insertion of an algal HydA sequence into a PsaC subunit and in vivo co-assembly of PSI and hydrogenase portions. As demonstrated herein, algal cells modified to express only the PSI-hydrogenase chimera make hydrogen at high rates in a light-dependent fashion for several days. In these engineered algal cells, photosynthetic electron flow is directed away from $CO_2$ fixation and towards proton reduction, thus demonstrating the possibility of driving novel redox chemistries using electrons from water splitting and the photosynthetic electron transport chain (PETC). Without being bound to any particular theory or mode of action, it is believed that expression of fusion proteins of this disclosure positions redox enzymes to directly capture electrons from photosystem I (PSI) before they enter the general cellular pool. Consequently, the genetic modification constrains $O_2$ evolution from PSII, preserves hydrogenase activity for sustained $H_2$ production for several days, and removes the need for use of nutrient deprivation, PSII inhibitors or mutations. Accordingly, the embodiments of this disclosure provide a cheap and renewable platform for creating biofactories capable of driving difficult redox transformations, powered only by the sun and using water as the electron source.

Accordingly, this disclosure provides genetically engineered cells that generate hydrogen and offer an ecologically-friendly, inexpensive renewable energy source. The cells may be algal cells or any cell capable of photosynthesis having PSI and an algal iron-iron hydrogenase. The hydrogenase is inserted in frame into the hinge region (β-hairpin region of FIG. 37) of PsaC of PSI such that the hydrogenase is positioned directly above the PsaC protein and captures the electrons produced by PSI. See FIG. 1. While the Examples provide two versions of this fusion protein those of skill in the art will appreciate that other algal Fe—Fe hydrogenases could be inserted into other PsaC hinge regions and that the linking regions between the two protein portions could have altered amino acids or the linkers could be of differing lengths. For Example, 4 PsaC proteins from various algal species are provided in FIG. 37 and three hydrogenases are provided in FIG. 38. Any of these can be used in any combination to make the fusion proteins described herein. In a first aspect, provided herein are genetically engineered algal cells that exhibit increased hydrogen ($H_2$) production under certain light conditions relative to control algae under the same conditions.

Figures 1A, 1B, 1C:
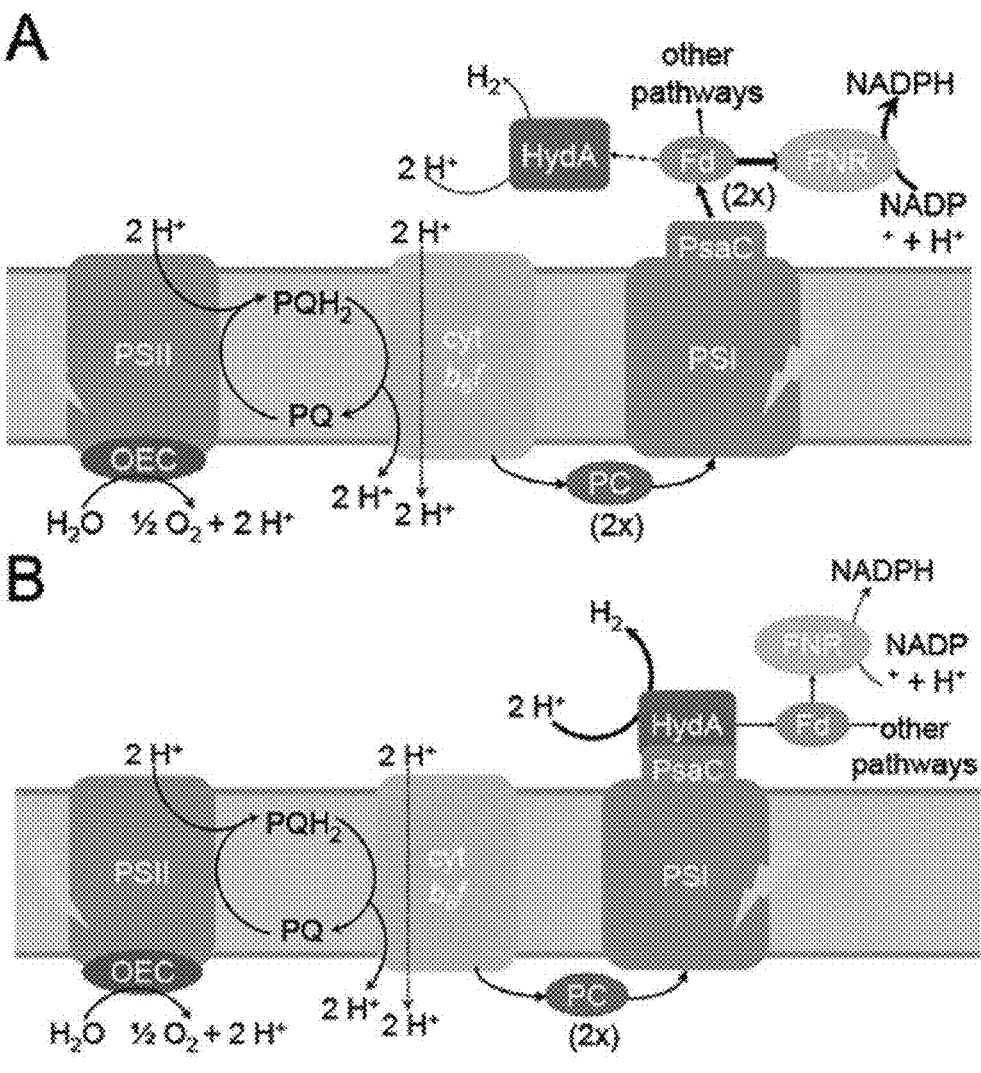
FIGS. 1A-1C present the photosynthetic electron transport chain (PETC) in WT cells (A), the proposed system (B), and a model of PSI-HydA (C). (A) The PETC in the thylakoid membrane drives linear electron flow, with water being oxidized by the oxygen evolving complex (OEC) of PSII and Fd being reduced by PSI, accompanied by formation of proton motive force. Two electrons will exit the PETC for each $H_2O$ oxidized. Under most conditions, NADPH is the major product, made by FNR. $H_2$ is a minor and/or transient product under anoxic conditions. (B) In the system described here, hydrogenase (HydA) is directly attached to PSI, which should direct most electrons to $H_2$ production at the expense of Fd reduction. (C) A model of PSI core subunits (PsaA—red, PsaB—blue) as ribbon diagrams, with PsaC-HydA2 (cyan), PsaD (yellow) and PsaE (magenta). Antenna pigments (chlorophyll (Chl) a and b-carotenes) are shown as green stick models, while FeS clusters and the H-cluster are shown as space-filling models. The predicted edge-to-edge distances between the inorganic substituents of the FeS clusters and the H-cluster (in Å) are shown to the left of the model.

In some embodiments, the genetically engineered cell comprises a nucleic acid sequence that encodes a fusion protein comprising a photosystem I (PSI) protein and an algal hydrogenase. In some embodiments, the engineered cells comprise a fusion protein comprising a photosystem I (PSI) protein, or a portion thereof, and an algal hydrogenase protein or a portion thereof. In some embodiments, the fusion protein comprises one or more subunits of PSI, and the hydrogenase is hydrogenase A (HydA), where the one or more PSI subunits are attached to HydA. As shown in FIG. 1C, PSI comprises multiple subunits (e.g., PsaA, PsaB, PsaC, PsaD, PsaE). In a preferred embodiment, the fusion protein is generated by inserting the sequence encoding HydA in place of one or more of the PSI subunits. For example, in some cases, the fusion protein is generated by inserting the nucleotide sequence encoding HydA (or a portion thereof) into the nucleotide sequence encoding a PSI subunit, thereby producing a recombinant nucleic acid molecule encoding a PSI-HydA fusion protein. In some embodiments, a nucleotide sequence encoding HydA is inserted into a sequence encoding the PsaC subunit. In some embodiment, the hydrogenase is inserted into the hinge region (shown as the β-hairpin in FIG. 37) of the PsaC subunit. The hydrogenase is inserted into the PsaC in frame such that the protein encoded by the polynucleotide contains the N-terminal portion of PsaC followed by the hydrogenase insertion and finally the C-terminal end of PsaC. The insertion of the hydrogenase into the PsaC protein can remove one or more amino acid from the hinge region of the PsaC protein. In the Examples, the insertion of the hydrogenase resulted in removal of at least a few amino acids and/or insertion of a few linking amino acids as described more fully below. The removal, addition or substitution of one, two, three, four, five, six or up to 10 amino acids is contemplated. The additional amino acids may be flexible such as alanine, glycine or serine to allow for proper folding of the multi domain resulting fusion protein.

A "deletion" in a fusion polypeptide refers to a change in the amino acid sequence resulting in the absence of one or more amino acid residues. A deletion may remove at least 1, 2, 3, 4, 5, 10, 20, or more amino acids residues. A deletion may include an internal deletion and/or a terminal deletion (e.g., an N-terminal truncation, a C-terminal truncation or both of a reference polypeptide).

"Insertions" and "additions" in a fusion polypeptide refers to changes in an amino acid sequence resulting in the addition of one or more amino acid residues. An insertion or addition may refer to 1, 2, 3, 4, 5, 10, 20, 30, 40, or more amino acid residues. A variant of a polypeptide may have N-terminal insertions, C-terminal insertions, internal insertions, or any combination of N-terminal insertions, C-terminal insertions, and internal insertions.

An engineered cell may be obtained by introducing a recombinant nucleic acid molecule that encodes a PSI-HydA fusion protein of this disclosure. As used herein, the term "recombinant nucleic acid" refers to a polynucleotide that is manipulated by human intervention. A recombinant nucleic acid molecule can contain two or more nucleotide sequences that are linked in a manner such that the product is not found in a cell in nature. In particular, the two or more nucleotide sequences can be operatively linked and, for example, can encode a fusion polypeptide. A recombinant nucleic acid molecule also can be based on, but manipulated so as to be different, from a naturally occurring polynucleotide, for example, a polynucleotide having one or more nucleotide changes such that a first codon, which normally is found in the polynucleotide, is biased for chloroplast codon usage, or such that a sequence of interest is introduced into the polynucleotide, for example, a restriction endonuclease recognition site or a splice site, a promoter, a DNA origin of replication, or the like.

In some embodiments, the amino acid sequence of the PsaC-HydA2 fusion polypeptide is:

```
                                     (SEQ ID NO: 1)
MAHIVKIYDTCIGCTQCVRACPLDVLEMVPWGGATATDAVPHWKLALEEL

DKPKDGGRKVLIAQVAPAVRVAIAESFGLAPGAVSPGKLATGLRALGFDQ

VFDTLFAADLTIMEEGTELLHRLKEHLEAHPHSDEPLPMFTSCCPGWVAM

MEKSYPELIPFVSSCKSPQMMMGAMVKTYLSEKQGIPAKDIVMVSVMPCV

RKQGEADREWFCVSEPGVRDVDHVITTAELGNIFKERGINLPELPDSDWD

QPLGLGSGAGVLFGTTGGVMEAALRTAYEIVTKEPLPRLNLSEVRGLDGI

KEASVTLVPAPGSKFAELVAERLAHKVEEAAAAEAAAAVEGAVKPPIAYD

GGQGFSTDDGKGGLKLRVAVANGLGNAKKLIGKMVSGEAKYDFVEIMACP
```

```
                        -continued
AGCVGGGGQPRSTDKQITQKRQAALYDLDERNTLRRSHENEAVNQLYKEF

LGEPLSHRAHELLHTHYVPGGASQMASAPRTEDCVGCKRCETACPTDFLS

VRVYLGSESTRSMGLSY.
```

The singly underlined residues indicate the PsaC fragments; the doubly underlined residues are the N-terminal junction; and the bold Ala residue is shared between the HydA2 and PsaC sequences. In another embodiment the amino acid sequence of the PsaC-HydA1 fusion polypeptide is:

```
                                     (SEQ ID NO: 2)
MAHIVKIYDTCIGCTQCVRACPLDVLEMVPWGGATATDAVPHVQQALAEL

AKPKDDPTRKHVCVQVAPAVRVAIAETLGLAPGATTPKQLAEGLRRLGFD

EVFDTLFGADLTIMEEGSELLHRLTEHLEAHPHSDEPLPMFTSCCPGWIA

MLEKSYPDLIPYVSSCKSPQMMLAAMVKSYLAEKKGIAPKDMVMVSIMPC

TRKQSEADRDWFCVDADPTLRQLDHVITTVELGNIFKERGINLAELPEGE

WDNPMGVGSGAGVLFGTTGGVMEAALRTAYELFTGTPLPRLSLSEVRGMD

GIKETNITMVPAPGSKFEELLKHRAAARAEAAAHGTPGPLAWDGGAGFTS

EDGRGGITLRVAVANGLGNAKKLITKMQAGEAKYDFVEIMACPAGCVGGG

GQPRSTDKAITQKRQAALYNLDEKSTLRRSHENPSIRELYDTYLGEPLGH

KAHELLHTHYVAGGASQMASAPRTEDCVGCKRCETACPTDFLSVRVYLGS

ESTRSMGLSY.
```

The singly underlined residues indicate the PsaC fragments; the doubly underlined residues are the N-terminal junction; the bold Ala residue is shared between the HydA2 and PsaC sequences and the italicized residues are a borrowed linker sequence from the PsaC-HydA2 fusion protein. Sequences having 90, 92, 94, 95, 96, 97, 98, 99 percent identity to the fusion protein of SEQ ID NO: 1 and SEQ ID NO: 2 are also contemplated. In particular the amino acids in bold, italics or double underlined in SEQ ID NO: 1 or 2 may be altered to provide additional linking regions between the portions of the fusion protein.

Regarding the fusion polypeptides disclosed herein, the phrases "% sequence identity," "percent identity," or "% identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, may be used to describe a length over which percentage identity may be measured.

Any appropriate technique for introducing recombinant nucleic acid molecules into algal cells may be used. Techniques for nuclear and chloroplast transformation are known and include, without limitation, electroporation, biolistic transformation (also referred to as micro-projectile/particle bombardment), agitation in the presence of glass beads, and Agrobacterium-based transformation. Accordingly, a recombinant nucleic acid molecule encoding a PsaC-HydA2 fusion protein may introduced into an algal cell by, for example, electroporation, by particle bombardment, by agitation in the presence of glass beads, or by Agrobacterium-based transformation. With chloroplast transformation, transgenes can be easily directed to integrate via homologous recombination. Nuclear transformation usually results in random integration events. In some embodiments the native psaC and hydA genes are mutated and/or replaced with the fusion protein in the cells such that all copies of PSI in the cell contain the fusion protein.

By way of example, described herein is introduction of a nucleic acid encoding a psaC-hydA fusion protein into an algal cell's chloroplast genome by particle-mediated gene transfer. In this example, flanking sequences were used to direct homologous recombination such that the recombinant nucleic acid replaces the endogenous psaC gene.

Any appropriate method can be performed to confirm introduction and expression of recombinant nucleic acids in the modified cell. For instance, polymerase chain reaction (PCR) or PCR-based methods can be used to verify replacement of psaC by psaC-hydA2 or psaC-hydA1. In some embodiments, amplified PCR products may be sequenced to ensure that no mutations are found in the recombinant nucleic acid as a result of the cloning process. The Example section demonstrates introduction of psaC-hydA2 and psaC-hydA1 into two strains: a hydA1-1 hydA2-1 mutant lacking endogenous hydrogenases, as well as a strain expressing a hexahistidine-tagged (H6) version of PsaA, a core subunit of PSI. In the hydA1-1 hydA2-1 mutant strain lacking endogenous hydrogenases, PSI-HydA serves as the only significant contributor to hydrogen production. In each of these strains, WT PSI would be replaced by PSI-HydA.

In some embodiments, it will be advantageous to measure hydrogenase activity. Any appropriate means of measuring hydrogenase activity may be used. In some embodiments, samples are collected for analysis of hydrogenase activity by gas chromatography (GC). Those of skill in the art are aware of methods to measure hydrogenase activity and such methods are provided in the Examples.

Any type of cell comprising a chloroplast or using photosystem I for photosynthesis may be used. For example, plant cells, algal cells, or cyanobacteria may be used. The cell must also have or be engineered to have the maturase proteins, hydEFG. The Fe—Fe hydrogenases for use in the methods suitably have a structure similar to algal hydrogenase A, in which the N-terminal and C-terminal ends of the protein are in proximity to each other or the hydrogenase protein is modified via truncation such that the N-terminal and C-terminal ends of the protein are in proximity to each other. Those of skill in the art can use protein modeling programs or crystal structures of hydrogenases to determine appropriate hydrogenases for use in the methods, cells and constructs provided herein. Several of these are provided in FIG. 38.

The terms "algal cell" or "algae" as used herein refer to plants or cells belonging to the subphylum Algae of the phylum Thallophyta. The algae are unicellular, photosynthetic, oxygenic algae and are non-parasitic plants without roots, stems or leaves; they contain chlorophyll and have a great variety in size, from microscopic to large seaweeds. Green algae, belonging to Eukaryota-Viridiplantae-Chlorophyta-Chlorophyceae, can be used. Blue-green, red, or brown algae may also be used. Exemplary algae for which the compositions and methods described herein includes those of the genus Chlamydomonas. In some embodiments, the engineered algal cells are unicellular green alga of the species Chlamydomonas reinhardtii, for which the sequence of all three genomes (nuclear, chloroplast and mitochondria) has been determined. Algal cells of the genus Chlorella may be used in other embodiments. For example, the PsaC of Chlorella vulgaris, or Picochlorum soloecismus may be used. The sequences and an alignment are provided in FIG. 37. Iron-Iron hydrogenases from any of these algal species may be inserted into the hinge region of the PsaC in the same or similar manner as shown in the Examples for Chlamydomonas.

In some embodiments, genetically engineered cells comprising the fusion proteins described herein exhibit at least a 5-fold increase in $H_2$ production with respect to a control cells of the same species under the same conditions. Advantageously, proton pumping and ATP production carried out by PETC is preserved in the genetically engineered cells. When cultures are maintained at high density (~30 mg Chl $L^{-1}$) under continuous illumination (approximately 600 mmol photons $m^{-2}s^{-1}$), production rate from the genetically engineered cells was 86.6±2.4 mL $H_2$ $d^{-1}$ per liter of culture. In some embodiments, the genetically engineered cells produce $H_2$ continuously for at least 5 days at an average rate of 14.0±1.7 mmol $H_2$ $h^{-1}$ (mg Chl)$^{-1}$. The results of the experiments completed in the Examples below showing the increase in hydrogen production can be summarized as follows:

TABLE 1

Maximum measured $H_2$ production rates in μmoles $H_2$ $h^{-1}$ (g dry weight cells)$^{-1}$ N/A (not measured)

| Condition | Time frame | | |
|---|---|---|---|
| (±light, ±acetate) | Short (s-min) | Intermediate (min-h) | Long (h-d) |
| Dark + acetate | N/A | 7.50 ± 0.002 | N/A |
| Light + acetate | 1727 ± 250 | 568 ± 136 | 267 ± 8 |
| Light + bicarbonate | 1114 ± 136 | N/A | N/A |

Any appropriate growth conditions can be used to maintain cultures of genetically engineered cells of this disclosure. In some embodiments, engineered algae are cultured in a liquid medium (e.g., Trisacetate-phosphate (TAP) that comprises mineral nutrients. In some embodiments, cultures are maintained in cell culture flasks under low ambient light conditions (B5 mmol photons m2 s1 PAR) with agitation (150 rpm). Larger cultures (1 L and greater) may be grown with continuous stirring and sparging with sterile filtered air. In some embodiments, cultures are maintained under autotrophic growth conditions. In such cases, a liquid Tris-bicarbonate phosphate (TBP) medium comprising 25 mM sodium bicarbonate (pH 7.0) in place of acetate can be used. In some embodiments, a photobioreactor vessel is used for growth of engineered algae.

In the Examples, the polynucleotide encoding the fusion protein was integrated into the native PsaC gene within the chloroplast genome via homologous recombination. A similar fusion protein can be recombined into the chloroplast genome of any cell containing a chloroplast, such as algal cell or plant cells. A similar fusion protein and polynucleotide encoding the same may be used in the cyanobacteria to engineer cyanobacteria cells capable of generating increased hydrogen. In another aspect, provided herein is a cell, suitably an algal cell, that has been modified to contain an expression cassette that drives expression of a fusion protein comprising a PSI protein and an Fe—Fe hydrogenase. For instance, provided herein are algae that have been modified relative to a naturally occurring algal cell, where the modified algal cell comprises an expression cassette that comprises a promoter operably linked to a nucleic acid sequence that encodes a fusion protein comprising a PSI protein and an algal hydrogenase. In preferred embodiments, the nucleic acid is a recombinant nucleic acid that encodes a PSI-HydA fusion protein, suitably the fusion protein includes the sequence of SEQ ID NO: 1 or SEQ ID NO: 2. In one embodiment, the fusion protein is expressed from an expression cassette including a promoter operably connected to the polynucleotide encoding the fusion proteins described herein. While PSI is encoded in the chloroplast, the gene and thus the fusion protein may be encoded in the nucleus, added as an additional copy in the chloroplast or even encoded on an extra chromosomal expression cassette such as a plasmid or artificial chromosome. In these alternative expression cassettes, the promoters may be selected based on the expression system being contemplated by those of skill in the art. For example as demonstrated in Reifschneider-Wegner et al. (Hydrogen Energy 39: 3657-3665 2014) the hydrogenase can be expressed in chloroplasts using the psbD promoter/5'UTR to drive expression of the chloroplast-optimized hydA gene. A similar system could be used for expression of the fusion protein described herein.

In another aspect, provided herein is algal biomass comprising genetically engineered algal cells of the disclosure. In particular, provided herein is algal biomass that contains genetically engineered algal cells that exhibit increased hydrogen production on particular growth (e.g., light) conditions relative to genetically unmodified algal cells or other controls when cultured under the same conditions. As used herein, the term "algal biomass" refers to the amount or density of algae in a given area or volume (e.g., of water or other liquid) at a given time. Algal biomass encompasses algae grown in various cultivation systems such as photoreactors and open ponds, but also algal material obtained from different types of waste from industry and sewage plants.

Expression cassettes and constructs comprising a polynucleotide encoding the fusion proteins comprising a PSI protein and an algal hydrogenase as described above are also provided here. The polynucleotide is optionally operably linked to a promoter that drives expression of the fusion protein in the cell. As used herein, the terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of natural or synthetic origin (which may be single-stranded or double-stranded and may represent the sense or the antisense strand). The polynucleotides may be cDNA or genomic DNA.

Polynucleotides homologous to the polynucleotides described herein are also provided. Those of skill in the art understand the degeneracy of the genetic code and that a variety of polynucleotides can encode the same polypeptide. In some embodiments, the polynucleotides (i.e., polynucleotides encoding the fusion polypeptides) may be codon-optimized for expression in a particular cell including, without limitation, a plant cell, bacterial cell, or algal cell. While particular polynucleotide sequences which are found in particular algae are disclosed herein any polynucleotide sequences may be used which encode a desired form of the polypeptides described herein. The particular polynucleotide sequences of the fusion polypeptides are provided as SEQ ID NOs: 1 and 2. These represent non-naturally occurring sequences. Computer programs for generating degenerate coding sequences are available and can be used for this purpose. Pencil, paper, the genetic code, and a human hand can also be used to generate degenerate coding sequences.

In another aspect of the present invention, constructs are provided. As used herein, the term "construct" refers to recombinant polynucleotides including, without limitation, DNA and RNA, which may be single-stranded or double-stranded and may represent the sense or the antisense strand. Recombinant polynucleotides are polynucleotides formed by laboratory methods that include polynucleotide sequences derived from at least two different natural sources or they may be synthetic. Constructs thus may include new modifications to endogenous genes introduced by, for example, genome editing technologies. Constructs may also include recombinant polynucleotides created using, for example, recombinant DNA methodologies.

The constructs provided herein may be prepared by methods available to those of skill in the art. Notably each of the constructs or expression cassettes claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

The constructs and expression cassettes provided herein may include a promoter operably linked to any one of the polynucleotides described herein but need not have a promoter and may be used for homologous recombination into the native site of psaC in the algae. Alternatively, the constructs may include a promoter and the promoter may be a heterologous promoter or an endogenous promoter associated with the PsaC polypeptide.

As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the disclosed polynucleotides are operably connected to the promoter. As used herein, a polynucleotide is "operably connected" or "operably linked" when it is placed into a functional relationship with a second polynucleotide sequence. For instance, a promoter is operably linked to a polynucleotide if the promoter is connected to the polynucleotide such that it may affect transcription of the polynucleotides. In various embodiments, the polynucleotides may be operably linked to at least 1, at least 2, at least 3, at least 4, at least 5, or at least 10 promoters.

Heterologous promoters useful in the practice of the present invention include, but are not limited to, constitutive, inducible, temporally-regulated, developmentally regulated, chemically regulated, tissue-preferred and tissue-specific promoters. The heterologous promoter may be a plant, animal, bacterial, fungal, or synthetic promoter.

In another aspect, provided herein are methods for producing hydrogen. To produce hydrogen, the genetically engineered cells described herein can be cultured in a bioreactor growth system and the gas released during growth can be collected, removed from the bioreactor, and the hydrogen can be separated and collected from the remaining air in the bioreactor after growth of the cells. In one embodiment, the cells are algal cells. As noted in the Examples, the cells expressing the fusion protein described herein may be cultured under conditions and in media to increase $H_2$ production. For example, the cells may be cultured under saturating light conditions to induce increased $H_2$ production.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

As used herein, the terms "optional" or "optionally" mean that the subsequently described event or circumstance may or may not occur, and that the description includes instances where said event or circumstance occurs and instances where it does not.

The present invention has been described in terms of one or more preferred embodiments, and it should be appreciated that many equivalents, alternatives, variations, and modifications, aside from those expressly stated, are possible and within the scope of the invention.

EXAMPLES

Example 1—In Vivo Fusion of Photosystem I (PSI) and Algal Hydrogenase

Using a unicellular green alga (*Chlamydomonas reinhardtii*) as an experimental system, an in vivo fusion of PSI and the [FeFe] hydrogenase expressed by the organism was created (see FIGS. 1B and 1C). While the structural gene for this hydrogenase is in the nuclear genome and the core photosystem subunits are chloroplast encoded, it has been shown that active hydrogenase can be made from a gene transplanted into the chloroplast chromosome. The data presented in this section demonstrate that photosynthetic flow in the re-engineered chloroplast is diverted from $CO_2$ fixation to proton reduction and results in sustained biohydrogen production (see FIG. 1B).

Experimental Design

Chimeric protein design and homology modeling: The site of insertion of the hydrogenase domain corresponds to residues 32-36 (DGCKA; SEQ ID NO: 14) of *C. reinhardtii* PsaC. Residue Asp32 was replaced with Gly for additional flexibility, and residues Cys34 and Lys35 were replaced with "trimmed" HydA2 sequence, such that PsaC-Gly33 was connected directly to the N-terminus of mature HydA2 (Ala63) and the C-terminus of HydA2 (Gly500) was connected to PsaC-Ala36 (see FIG. 6). Trimming of the HYDA2 sequence consisted of removal of the transit peptide from the N-terminus (first 62 residues) and the last 5 residues (which are not conserved) from the C-terminus.

To model the structure of PSI-HydA, the protein structure prediction webtool Phyre[22] (intensive algorithm) was used to model individual subunits of *C. reinhardtii* PSI (PsaA, PsaB, PsaC, PsaD, PsaE and PsaF) and HydA2, based on the sequences of the polypeptides from protein data bank. Following removal of residues D32-K35 of PsaC in Pymol, the docking of HydA2 was performed using the ClusPro[23] server with distance restraints of 10 Å, corresponding to the amino acid residues involved in the junctions in the chimeric protein (Trp31 of PsaC to the N-terminal Gly of the modified HydA2 and the C-terminal Gly of the modified HydA2 to Ala36 of PsaC). The most plausible model based on ClusPro2's energy minimization algorithm was chosen and, after formation of two peptide bonds between PsaC and HydA2, the connecting loops were allowed to relax, using the ModLoop server[24]. PsaD and then PsaE were then docked to the PsaC-HydA2 chimera with ClusPro2 as well.

Generation of cells expressing PSI-hydrogenase: The psaC hydA2 fusion sequence (see FIG. 6) was synthesized by Genscript (Piscataway, NJ USA) and inserted via flanking NdeI and BglII sites into the pBS-EP5.8 aadA vector[25] digested with NdeI and BglII. The resulting pAK10G plasmid neatly replaces the psaC gene with the designed psaC-hydA2 fusion gene. This plasmid was introduced into the hydA[26] and PBC4-2 strains of *C. reinhardtii* by particle-mediated transformation. The latter strain combines two mutations in the chloroplast genome: deletion of psaC[27] and the hexahistidine-tagged psaA exon 1.[28] The transformants were initially selected on TAP plates with 100 mg L$^{-1}$ spectinomycin in the dark. Individual colonies were passaged alternately on plates containing 100 mg L$^{-1}$ streptomycin or 300 mg L$^{-1}$ spectinomycin in the dark and colony purified until they became homoplasmic, as determined by PCR (see method below). The amplified PCR products were verified by Sanger sequencing to ensure that no mutations in the introduced psaC-hydA2 gene had arisen during the process. The same transformation and verification steps were performed on the strain expressing a hexahistidine-tagged (H$_6$) version of PSI.[29]

PCR analysis of algal transformants: PsaC-HydA2 detection PCR was performed with flanking primers (PsaC5': TAATATGGAGATGACATATTTAG (SEQ ID NO: 10) and PsaC3': GATCTCACCAAGATACTCCC (SEQ ID NO: 11)) as well as with gene-specific primers (PsaC5'int: TCAATGTGTACGTGCTTGTCC (SEQ ID NO: 12) and PsaC3'int: ACAACGTTTGCAACCTACACA (SEQ ID NO: 13)) on 100 ng of genomic DNA using MeanGreen 2×Taq DNA polymerase master mix (Syzygy Biotech). Reactions (50 μL) were cycled 35 times (95° C. for 15 seconds (s), 51° C. for 15 s, 72° C. for 90 s) using initial primer concentrations of 0.5 μM. To determine the limits of detection of the PCR for the psaC gene, test PCR templates were generated by diluting genomic DNA from the hydA strain (containing psaC) into genomic DNA from the psaCΔ mutant (lacking psaC)[27] at the same concentration, in order to emulate conditions of heteroplasmy (10%, 1% psaC) and homoplasmy (100%, 0% psaC).

Growth conditions: Unless otherwise specified, algae were grown in liquid Trisacetate-phosphate (TAP) medium with revised mineral nutrient supplement[30] in Erlenmeyer baffled cell-culture flasks under low ambient light conditions (approximately 5 μmol photons m$^{-2}$ s$^{-1}$ PAR) with agitation (150 rpm). Larger cultures (1 L and greater) were grown with continuous stirring and sparging with sterile filtered air. For autotrophic growth, Tris-bicarbonate phosphate (TBP) medium was prepared by substituting 25 mM sodium bicarbonate (pH 7.0) for acetate (~16.6 mM) in the medium.

An FMT-150 (Photon Systems International, Brno, Czech Republic) photobioreactor (PBR) system equipped with pH and Clark-type O$_2$ electrodes was used to obtain growth curves at constant temperature (24° C.). Starter cultures were pre-grown in TAP and washed twice with TBP. Cells were resuspended in TBP to a final OD$_{680}$ of 0.1. At the beginning of each run, the photobioreactor vessel was sparged with N$_2$ for ~1 hour. Afterwards, the cultures were sealed and stirred for the duration of the experiment.

Chlorophyll (Chl) measurement: Concentrations of Chl a and b were determined as described in Porra et al.[31]

Thylakoid and PSI preparation: Thylakoid membranes were prepared as previously described[25], with minor modifications outlined below. Cells were grown in 4 L flasks and centrifuged at 3500×g at 4° C. for 10 min. The pellet was washed with H1 buffer (25 mM HEPES-KOH, 5 mM MgCl$_2$, 0.3 M sucrose, pH 7.5), flash-frozen in liquid nitrogen, and stored at −80° C. Subsequent steps were performed in the dark and samples were kept at 4° C. Cells were resuspended at 2-4×10$^8$ cells mL$^{-1}$ in H1 containing 1 mM phenylmethane sulfonyl fluoride to inhibit proteolysis. Cell breakage was accomplished with a French Press (Aminco) at ~1.7 tons pressure. Unbroken cells were pelleted by centrifugation at 2000×g for 1 min, and the supernatant was centrifuged at 20,000×g for 10 min. The pelleted membranes were washed in 50 mL of H2 buffer (5 mM HEPES-KOH, 10 mM EDTA, 0.3 M sucrose pH 7.5) and resuspended in H3 buffer (5 mM HEPES-KOH, 10 mM EDTA, 1.8 M sucrose, pH 7.5). A discontinuous sucrose gradient was prepared using H3 buffer containing suspended thylakoid membranes, which was in turn overlaid with 1.3 M sucrose and 0.5 M sucrose solutions. After 1 hour of centrifugation in an SW-28 rotor at 25 000 rpm, the upper green band (0.5/1.3 M interface) was collected and washed with 3× volume of H6 buffer (5 mM HEPES-KOH, 10 mM EDTA pH 7.5). Purified thylakoids were concentrated by centrifugation (90 000×g for 30 min) and resuspended in H6+20% glycerol and were either stored at 200 K after flash-freezing in liquid N$_2$ or solubilized for PSI purification.

PSI particles were purified from thylakoid membranes on sucrose gradients after solubilization with β-dodecyl maltoside (β-DDM), as described in Li et al.[29] Purification of hexahistidine-tagged PSI was performed as described previously,[28] except that a Ni$_{(II)}$-iminodiacetic acid (IDA) resin (G-biosciences, St. Louis, MO U.S.A.) was used.

Anoxic PSI-HydA2 isolation: Twelve liters of cells grown aerobically in TAP to mid-log phase were harvested and resuspended in fresh TAP to ~200-300 μg mL$^{-1}$ of total Chl and sparged with Ar for ~4 h. After this point, all preparation steps were done in an anaerobic glovebox (Coy) filled with a 5% H$_2$/95% N$_2$ gas mixture. Sodium dithionite was added to 2 mM final concentration and 5 mL aliquots were pelleted and stored in liquid nitrogen. Once thawed, each pellet was resuspended in breaking buffer (0.1 M Tris-HCl, pH 8.0), (10 mM EDTA-KOH, 1 mM PMSF and 2 mM Na$_2$S$_2$O$_4$) in a total volume of 30 mL. Cell lysis was accomplished using a Branson sonifier S-450 operated at amplitude 3, 50% duty cycle for a total of 6 min (2 minutes sonication followed by 2 min waiting) on chilled beads (−20 to −10° C.) to achieve complete cell lysis. Crude thylakoids were pelleted (208 000×g, 15 min, 4° C.), and resuspended in solubilization buffer (25 mM Tricine-KOH, pH 8.0, 300 mM KCl, 10% glycerol) containing 2 mM sodium dithionite. Solubilization and IMAC purification steps were done as described above with the exception of using Ni-Pentat™ resin (Marvelgent Biosciences), Tricine-KOH buffer (pH 8.1) and 200 mM imidazole for elution. Purified PSI was stored in 25 mM Tricine-KOH (pH 8.1), 300 mM KCl, 10% glycerol, 0.03% β-DM. Aliquots were flash frozen and stored in liquid nitrogen.

Laser-flash spectroscopy: Samples of thylakoid membranes (60 μg Chl mL$^{-1}$ in 5 mM HEPES-KOH, pH 7.5) or PSI particles (6 μg Chl mL$^{-1}$ in 5 mM Tricine-KOH PH 8.0, 0.03% β-DDM) were diluted with the same buffer containing 10 mM sodium ascorbate in the dark. A JTS-10 (Bio-Logic) kinetic spectrophotometer was used to monitor absorbance changes at 696 nm. Excitation was provided by a frequency-doubled Nd/YAG laser (532 nm) generating ~6 ns pulses (~25 mJ per pulse).

A saturating laser flash was used to create the $P_{700}{}^+(F_A/F_B)^-$ charge-separated state, which occurs in <1 μs.[32] Absorbance changes at 696 nm were monitored with dim 10 μs flashes before and after the laser flash (starting 250 μs after the flash) to monitor creation and decay of $P_{700}{}^+$. To eliminate actinic effects of the probing light and electronic artifact due to changing data collection rates, a background transient (with the laser shutter closed) was subtracted. The decay of $P_{700}{}^+$ was fit to a sum of 2-6 exponential decay components using the Levenberg-Marquardt iteration algorithm.

Anaerobic adaptation: To allow activation of the hydrogenase enzyme, cells were harvested in early/mid-logarithmic phase (2-6 μg Chl mL$^{-1}$) by centrifugation (3500×g for 5 min) and resuspended in fresh TAP medium at ~1-2 μg Chl mL$^{-1}$ (for in vivo H$_2$ measurements). Ten mL of the cell suspension was placed in a 25 mL clear glass bottle sealed with stoppers, wrapped in aluminum foil and bubbled with argon (flow rate 10-15 mL min$^{-1}$) for 90 min in the dark, unless otherwise indicated, prior to the start of the H$_2$ production period. Once sparging was terminated, cells were agitated on a shaker at 160 rpm.

In vitro hydrogenase activity: Cells were centrifuged and resuspended at ~30 μg Chl mL$^{-1}$ in anaerobic adaptation buffer (50 mM potassium phosphate pH 7.2, 3 mM MgCl$_2$) and sparged with water-saturated argon for variable times in the dark in the initial experiments; the standard time was 90 min thereafter. For each reaction, 1 mL of reaction buffer (100 mM Tris-HCl, pH 7.3, 1 M NaCl, 10 mM methyl viologen, 0.2% Triton X-100) was mixed with 0.2 mL of 100 mM Na$_2$S$_2$O$_4$ (dissolved in 30 mM NaOH) in an anoxic glovebox (Coy) and sealed; the headspace of the vial was sparged with argon for 20 min to remove any residual H$_2$ from the glovebox gas and warmed to 37° C. prior to injection of 100 μL of cell suspension into the reaction mixture. The vial was mixed well, temperature was maintained at 37° C. with mild shaking, and aliquots of the headspace gas were removed at intervals and analyzed by gas chromatography (see below).

Gas chromatography (GC) measurements: A model SRI 310 GC equipped with a thermal conductivity detector (TCD) and molecular sieve (13X or 5A) was used for all gas measurements. A sample (80 μL) of the headspace gas was removed with a 1710RN airtight Hamilton 100 μL syringe (that had been flushed with argon) and injected into the GC. A 1% H$_2$/99% N$_2$ gas mixture (Supelco) was used to create a standard curve for H$_2$, and air was used as a standard for O$_2$ and N$_2$. The O$_2$:N$_2$ ratio was used to monitor for air contamination during sampling, as the headspace of all samples was primarily Ar.

Immunoblotting: Polypeptide separation and immunoblotting was performed as described previously.[20] Isolated PSI$^{H6}$ or PSI-HydA$^{H6}$ were loaded on the basis of $P_{700}$ photobleaching activity (see below): 1.6 pmol of $P_{700}$ for detection of small polypeptides (PsaC, PsaD, PsaC-HydA2) or 0.4 pmol of $P_{700}$ for detection of larger polypeptides (PsaA).

Membrane inlet mass spectrometry (MIMS) measurements: Cells grown to early log phase were spun down and resuspended to 15 μg Chl mL$^{-1}$ in a total volume of 5 mL in TAP or TP medium (with or without acetate, respectively); 50 mM HEPES (pH 7.2) and 2 mM NaHCO$_3$ were included to maintain pH and CO$_2$ levels. Cell were loaded into a closed temperature-controlled (24.5° C.) and stirred MIMS cuvette. Anaerobiosis was achieved in approximately 1 hour due to respiration in the dark; relevant gas masses were monitored continuously. After approximately 1 h, cells were exposed to various intensities of red light (635 nm via the actinic module of the DUAL-PAM 100 from Heinz Walz GmbH) for 2 min interspersed with 2 min darkness. Rates were calculated from the slope of the best linear fit over a 1 min period. H$_2$ and O$_2$ analysis was done by MIMS.[33] Enforced anaerobiosis with glucose oxidase and glycolaldehyde treatment were performed as described previously.[16]

Light-to-hydrogen conversion efficiency: PAR was determined with Li-COR photon counter equipped with quantum sensor (LI-190R). Efficiency calculations were performed as previously described[34] with slight modifications.

$$\eta(\%) = \frac{\left(\Delta G^\circ - RT\ln\frac{P^\circ}{P}\right)v_{H_2}}{E_i At} \times 100,$$

where $\Delta G^\circ$ is the standard Gibbs free energy for water oxidation (237.2 kJ mol$^{-1}$ at 25° C. and 1 atm), R is the universal gas constant, T is absolute temperature (K), P$^\circ$ and P are the hydrogen partial pressures (standard and observed, respectively), $v_{H_2}$=amount of H$_2$ produced (mol), E$_i$=energy flux of the incident light (J m$^{-2}$ s$^{-1}$), A=illuminated surface area (m$^2$), t=duration of illumination (s). Energy for the incident light was either calculated using the Planck-Einstein relation for red light at 630 nm or measured using a LI-200R pyranometer (LI-COR Biosciences, Lincoln, NE, USA) for white light.

Dissolved O$_2$ measurements in vivo: Dissolved O$_2$ was monitored with a Firesting O$_2$ optical oxygen meter (Pyro-Science). Cells were washed with either fresh TAP or TBP twice, then resuspended at approximately 5 μg Chl ml$^{-1}$. They were dark adapted and sparged with filtered water-saturated air for 10 min before the run. Each run made use of 2 ml of cell suspension stirred continuously in a 5-ml cuvette. For light-dependent O$_2$ evolution rates, the dark O$_2$ consumption rate (the average of rates in the dark just before and after illumination) was subtracted from the net evolution rate in the light. For maximal O$_2$ evolution rates, the cell suspensions (in TBP) were subjected to a 5-min dark period in the presence of 0.2 mM Phenyl-p-benzoquinone (PPBQ; Acros Organics), followed by 5 min of high red light (~2300 μmol photons m$^{-2}$ s$^{-1}$) and 5 min of darkness.

NADP$^+$ photoreduction assay: The reaction mixture (2 mL) consisted of 10 mM sodium ascorbate (Sigma), 17 μM plastocyanin (Pc: prepared in-house from a recombinant source as described in Kuhlgert 2012), 3 μM ferredoxin (Fd: prepared in-house from a recombinant source as previously described in Marco 2018), 0.2 μM FNR (prepared in-house from a recombinant source as previously described in Marco 2018), 2.5 mM NADP$^+$ disodium salt (Roche), and 27 nM PSI in reaction buffer (50 mM Tris-HCl, pH 7.4, 3.35 mg $mL^{-1}$ BSA, 10 mM $MgCl_2$, 200 mg $mL^{-1}$ sucrose, 0.03% β-DDM). The concentrations of Pc, Fd, and FNR were optimized for maximal reaction rates with WT PSI. Each sample was mixed in a 3-mL quartz cuvette with a stir bar for 3 minutes. All preparatory steps were done in the dark. The reference cuvette contained all components except PSI. Absorbance at 340 nm was measured with a Perkin Elmer Lambda35 double-beam spectrophotometer. Band pass filters (340 nm, 27 nm FWHM, Omega Optical) were placed before the detectors to block actinic light. A red LED light source (630 nm, 300 μmol photons $m^{-2}$ $s^{-1}$) was assembled on top of the cuvette and controlled manually. A technical replicate consisted of a "dark" run of 3 minutes using a data collection frequency of 6 Hz, followed by 3 min of data collected with the actinic light on. The data were analyzed for each run separately; each "dark" slope was subtracted from the following "light" slope to obtain a light-dependent rate before averaging. The dark rates never exceeded 11% of the light rates. An initial rate was determined from the slope of the line (linear fit with the instrumental weighting of error) to the first 9 points of each averaged data set using Beer's law and the extinction coefficient for NADPH at 340 nm (6.22 $mM^{-1}$ $cm^{-1}$) with a path length of 1 cm.

Flavodoxin photoreduction assay: Recombinant Synechococcus sp. PCC7002 flavodoxin was prepared as previously described in Zhao 1998. The reaction mixture consisted of ~100 nM PSI particles in 25 mM Tricine-KOH (pH 8), 50 mM $MgCl_2$, 20 mM KCl, 0.03% β-DDM, 5 mM sodium ascorbate, 5 μM Pc, and 5 μM flavodoxin. All preparation steps were performed in the dark. Accumulation of flavodoxin semiquinone was monitored with a JTS-10 kinetic spectrometer (Bio-Logic) using 10-μs flashes centered at 573 nm (6 nm full width at half maximum). Actinic light consisted of 250-ms LED pulses at 630 nm (3000 μmol $m^{-2}$ $s^{-1}$), with the probe flash occurring 50 ms after the actinic pulse ceased, allowing time for any rapid decay processes to be complete. (This 250-ms/50-ms duty cycle was factored in the rate calculations.) An extinction coefficient of 5100 $M^{-1}$ $cm^{-1}$ for the flavosemiquinone-minus-flavin difference at 573 nm was used, based on the published difference spectrum of Synechococcus sp. PCC7002 flavodoxin (see Meimberg 1999). The slow baseline drift in the dark was subtracted from the rate in the light to yield light-dependent rate.

$O_2$ uptake assay: Reaction mixtures were prepared as in the flavodoxin photoreduction experiment, except that 2,6-dichlorophenol indophenol (0.2 mM) was used as mediator instead of Pc, and flavodoxin was not added. Dissolved $O_2$ was measured with a Clark-type electrode. Each sample was mixed in the dark to saturate with air. Data was collected with 1 Hz frequency for 1 minute in the dark, followed by 2 minutes under saturating illumination from a white LED (1200 μmol $m^{-2}$ $s^{-1}$ of PAR). Rates of $O_2$ consumption/production in the light were calculated for each replicate (n=3) via linear regression of 10-s intervals. The dark rate for each replicate was calculated from the last 2 minutes of the 3-min dark run of the sample before illumination commenced. This dark rate was subtracted from the light rate to determine the light-dependent rate, which was normalized to the amount of photobleachable $P_{700}$. The dark rate never exceeded 18% of the corresponding light rate. After data collection, the Chl content of each sample was measured to ensure consistency between replicates.

In vivo $P_{700}$ photobleaching and fluorescence measurements: Cells were collected during early log phase, centrifuged (3500×g for 5 min) and resuspended to a Chl concentration of 33 μg $mL^{-1}$ ($P_{700}$) or ~9 μg $mL^{-1}$ (fluorescence) in 20% Ficoll™ PM400 (GE Healthcare), 10 mM sodium phosphate (pH 7.2). $P_{700}$ bleaching and recovery was performed essentially as previously described in Alric 2010. Absorbance changes at 695 nm were measured with the JTS-10 spectrometer. For $P_{700}$ photobleaching, actinic light (630 nm) was briefly (200 μs) switched off for each 10-μs detection measurement during the 10-s illumination period, followed by the dark decay. For fluorescence, cells were dark adapted for 5 min before taking each measurement. (During dark periods, samples were sparged with air to prevent development of anoxia.) Fluorescence emission from Chl was measured with the JTS-10 Fluo59 accessory. A saturating pulse (80 ms, 8 mmol photons $m^{-2}$ $s^{-1}$, 520 nm) was used to obtain $F_{max}$, measured 170 μs after the pulse. The steady-state fluorescence parameter ($F_s$) was measured after 2 minutes of illumination (520 nm) with actinic light of variable intensities. Quantum yields of PS II (Φ(II)) were calculated as described in Genty 1989.

Long term $H_2$ production in a photobioreactor (PBR): Cells were grown in 4 L TAP under ambient room light (~5 μmol $m^{-2}$ $s^{-1}$ photosynthetically active radiation (PAR)) with constant air-sparging and stirring. They were harvested in the mid log-phase, resuspended in ~500 mL fresh TAP to $OD_{735}$≈0.7 (corresponding to ~30 μg/mL of Chl) and transferred to the 400-mL PBR vessel. Once in the FMT150 PBR (see above), the culture was continuously sparged with Ar at 80 mL $min^{-1}$, controlled at the influx and monitored at the efflux by mass flow controllers (MC-500SCCM-D/5M, Alicat Scientific, USA). After 2 h of anaerobic adaptation in the dark, the culture was illuminated continuously with white light at 600 μmol photons $m^{-2}$ $s^{-1}$ PAR. Sterile argon was hydrated by bubbling through water and then through sterile TAP media, before it entered the PBR vessel. The PBR was operated in turbidostat mode with $OD_{735}$ set to remain between 0.60 and 0.65; Ar-sparged sterile TAP was used to dilute the culture, which was constantly stirred. The PBR gas efflux was passed through a 500-mL trap flask (to retain excess culture) before passing out and through monitoring mass flow controller. A rubber septum mounted atop the trap flask allowed probing of the efflux gas with an airtight syringe (100 μL, Hamilton), followed by injection of the sample into the GC-TCD, as in the experimental section.

Results and Discussion

Chimeric protein design and creation: Based on the crystal structure of cyanobacterial PSI (1JBO)[35] and a homology model of HydA2,[36] the turn of a β-hairpin over the terminal $F_B$ cluster in PsaC was selected as the optimal insertion point for the hydrogenase domain. The entire sequence of the mature HydA2 hydrogenase from C. reinhardtii was inserted into this site as an in-frame fusion that would effectively split PsaC into two polypeptide segments. (See Experimental Design section for details and FIG. 6 for exact sequence of the chimeric polypeptide). The N- and C-termini of HydA2 are in close proximity,[36] in principle allowing this type of chimeric polypeptide to fold as two domains, with the HydA domain presumably folding first, allowing the two PsaC fragments to fold together. According to the modeling studies, this design would place the [4Fe-4S] cluster of HydA2 relatively close to the $F_B$ cluster of PSI (14.8 Å edge-to-edge distance, see Experimental Design section for details). The fusion gene and protein are henceforth referred to as psaC-hydA2 and PsaC-HydA2, respectively. When co-assembled with PSI, the chimeric protein is called "PSI-HydA" (see FIG. 1C for a model).

The psaC-hydA2 gene was introduced into the chloroplast genome by particle-mediated gene transfer using flanking sequences to direct homologous recombination such that it would replace the endogenous psaC gene.[25] Serial cloning under selective conditions was maintained until a homoplasmic state was achieved (i.e., all copies of psaC replaced by psaC-hydA2), as verified by PCR (FIG. 7). The amplified PCR products were sequenced to ensure that no mutations in the chimeric gene had arisen during the process. The psaC-hydA2 gene was introduced into two strains: a hydA1-1 hydA2-1 mutant lacking endogenous hydrogenases[26] as well a strain expressing a hexahistidine-tagged ($H_6$) version of PsaA, a core subunit of PSI.[28] Note that in the former, PSI-HydA is the only significant contributor to hydrogen production; in both strains, WT PSI would be replaced by PSI-HydA. For brevity, the congenic D66 control strain is referred to as wild-type (WT), the hydA1-1 hydA2-1 strain is called hydA, and the hydA1-1 hydA2-1 [psaC-hydA2] transformant is referred to as ΨH1. The strains expressing $H_6$-tagged PSI are called $WT^{H6}$ (with normal PsaC) or $ΨH1^{H6}$ (with PsaC-HydA2).

Subunit composition of PSI-HydA chimera: PSI and PSI-HydA were purified from $WT^{H6}$ and $ΨH1^{H6}$, respectively, via immobilized metal affinity chromatography.[28] Purified complexes were denatured with SDS and equivalent amounts of PSI were analyzed by immunoblotting with antibodies against PSI subunits and hydrogenase, to assess the subunit composition of the complexes. The anti-PsaC antibody recognized a ~9 kDa polypeptide in WT PSI (FIG. 2A, left), consistent with its predicted size (8.8 kDa). This polypeptide was not observed in the PSI-HydA complex; instead, a new ~52 kDa polypeptide was seen, similar to the predicted size of the PsaC-HydA2 polypeptide (56 kDa). Probing with anti-HydA antibodies revealed a polypeptide of the same size in PSI-HydA complexes, but not in WT PSI (FIG. 2A, right). Thus, PSI complexes in this strain incorporate PsaC-HydA2 rather than PsaC.

Roughly equal amounts of PsaA were detected in PSI and PSI-HydA (1.0:1.1; FIG. 2B) when the lanes were loaded on the basis of equal photochemical activity (see FIG. 3A), implying that >90% of the PSI-HydA in the ΨH1 cells is photochemically active. It was not expected that any unassembled PsaA polypeptide would be present, as it has been shown that the quality control system of the chloroplast keeps the level of unassembled subunits of PSI or other multi-subunit complexes very low.[37]

Based on the structure of cyanobacterial PSI,[35] as well as mutagenesis[38] and modeling[39] studies, it is thought that the Fd-docking site of PSI is formed by PsaC in concert with PsaD. The structure of PSI reveals an intimate interaction between PsaC and a long C-terminal extension of PsaD, and the addition of the HydA domain in the fusion had the potential to interrupt this interaction and prohibit assembly of PsaD into the complex. However, it was observed that the level of PsaD in the purified PSI complexes was similar in both preparations (FIG. 8), consistent with our model of PSI-HydA (FIG. 1C).

Activities of the PSI-HydA chimera in vitro: Laser-flash spectroscopy experiments were performed to assess the photochemical activity of the PSI portion of the PSI-HydA chimera. $P_{700}$ is a pair of Chl a molecules serving as the primary electron donor in PSI. Excitation of PSI produces a charge separated state in which $P_{700}$ is oxidized ($P_{700}^+$) and the terminal acceptor is reduced. In the absence of an electron acceptor, the rate of charge recombination is characteristic of the charge separated state; for example, charge recombination of $P_{700}^+(F_A/F_B)^-$ occurs in 40-200 ms, but is >50 times faster from the prior charge separated state ($P_{700}^+FX^-$). In the absence of the PsaC subunit, the PsaA/PsaB heterodimer is degraded and does not accumulate in C. reinhardtii.[40] Therefore, the level of photoactive PSI can be used to assess the ability of PsaC-HydA2 to assemble with and stabilize the PSI core. The amount of photo-bleachable $P_{700}$ in thylakoid membranes isolated from ΨH1 was ~15% that of WT (FIG. 3A). The lowered accumulation of PSI-HydA was not unexpected, given that point mutations of single residues in PSI can result in more drastic effects. The kinetics of fast $P_{700}^+$ decay (FIG. 3A inset) are very similar in PSI and PSI-HydA, indicating that the $F_A$ and $F_B$ clusters must be properly assembled within the PsaC domain of the chimeric protein (Table 2). Oxygen can readily accept electrons from PSI, effectively quenching back reactions and contributing to overall "electron escape" that must be replenished by an exogenous electron donor (i.e., ascorbate). In order to get a better understanding of charge recombination kinetics in the PSI-HydA2 chimera, PSI complexes were prepared anoxically from anaerobically adapted $WT^{H6}$ and $ΨH1^{H6}$ cultures. As seen in FIG. 9 electron escape is reduced in both preparations to ~24% (phase assigned to "ascorbate" in FIG. 9B), and there is the typical biphasic kinetics of charge recombination from the $P_{700}^+(F_A/F_B)^-$ state in the 40-200 ms time range. In the PSI-HydA2 chimera, there are 3 new kinetic phases. The fastest two (decay times of 0.56 and 3.0 ms) represent charge recombination of the $P_{700}^+FX^-$ state, and together represent ~12% of the total decay, indicating that the association of PsaC-HydA2 with PSI may be weaker than PsaC and some of it dissociates during purification. There is also a new component with a lifetime of 550-600 ms, representing ~9% of the total decay. We tentatively assign this to charge recombination from the [4Fe-4S] cluster of the HydA2 domain.

TABLE 2

| Fitting parameters of $P_{700}^+$ decay in thylakoid membranes | | | |
| --- | --- | --- | --- |
| parameter | PSI | PSI-hydrogenase | Comments |
| $τ_1$ | 91 ± 5.6 ms | 79 ± 12 | Decay constant of fast phase (ms) |
| $A_1$ | 33 ± 0.7% | 30 ± 1.5% | Amplitude of fast phase (% of total) |
| $τ_2$ | 5500 ± 150 ms | 4500 ± 290 | Decay constant of slow phase (ms) |
| $A_2$ | 60 ± 0.6% | 51 ± 1.3% | Amplitude of slow phase (% of total) |
| $A_0$ | 6 ± 0.4% | 15 ± 0.8% | Non-decaying fraction (% of total) |
| $R^2$ | 0.9993 | 0.9961 | Coefficient of determination |

Table 2. Bi-exponential fitting parameters of $P_{700}^+$ decay curves in vitro shown in FIG. 3A. Function: $A(t)=A_0+A_1 exp(-x/t_1)+A_2 exp(-x/t_2)$. Fast recovery phase parameters $\tau_1$ and $A_1$ are likely due to charge recombination from $P_{700}^+$ $(F_A/F_B^-)$ while $\tau_2$ and $A_2$ result from a slow reduction of $P_{700}^+$ by ascorbate.

P700 photobleaching and recovery in thylakoid membranes: A saturating laser flash was used to trigger charge separation and creation of the $P_{700}^+(F_A/F_B)^-$ charge-separated state in <10 ns; (see Fischer 1999 and Brettel and Leibl 2001) photo-induced bleaching of $P_{700}$ and its recovery were monitored with 10-μs LED flashes. The fast component is attributed to charge recombination of the $P_{700}^+(F_A/F_B)^-$ state, which has a decay time of 40-200 ms, whereas the preceding $P_{700}^+F_X^-$-state recombines in 0.5-1 ms (see Brettel 1997). The slower decay is attributed to reduction of $P_{700}^+$ by ascorbate in the fraction of photosystems in which the electron on $F_A/F_B$ escaped to an exogenous acceptor (e.g. $O_2$) and is commonly seen (see Jordan 1998). Charge recombination from the iron sulfur cluster of hydrogenase domain of the chimera doesn't occur when oxygen is present as over 50% of electrons escape ETC and must be replenished by ascorbate. The fitting parameters are reported in Table 2.

For the experiment shown in FIG. 9, essentially the same analysis was done, but it was performed on purified $PSI^{H6}$ and $PSI^{H6}$-HydA2 that had been prepared and loaded into the cuvette anoxically.

The HydEF/G maturases are required for insertion of the di-iron site into the HydA domain after assembly of the [4Fe-4S] cluster by the chloroplast SUF machinery,[41] and it was unclear if the maturases would be able to access the HydA domain in the new chimeric context. The hydrogenase activity of cells expressing PSI-HydA was assessed in detergent-permeabilized cells with reduced methyl viologen (MV) as electron donor. It was determined that maximal hydrogenase activity was attained within 1.5 hours after a shift to anaerobiosis, similar to what was shown for WT hydrogenases in *C. reinhardtii*.[15] (FIG. 3B). The parental hydA strain exhibited a very slow rate of $H_2$ production (~4.1±0.2 μmol h$^{-1}$ (mg Chl)$^{-1}$), as expected, while the WT rate was 770±50 μmol h$^{-1}$ (mg Chl)$^{-1}$. The $H_2$ production rate in permeabilized ΨH1 cells was linear with time over the 20-min time course, similar to the permeabilized WT cells, indicating that the hydrogenase domain in PSI-HydA was not unstable (FIG. 3B insect). They produced $H_2$ at a rate of ~380±80 μmol h$^{-1}$ (mg Chl)$^{-1}$. Since the hydrogenase activity in the parental strain is ~1% of this, nearly all of the $H_2$ produced by the ΨH1 cells can be attributed to the PSI-HydA chimera. Using the extinction coefficient of $P_{700}$,[42] we estimate the amount of PSI-HydA in the ΨH1 strain as 1 per 5650 Chl. If each PSI-HydA had an active hydrogenase, the turnover frequency for PSI-HydA would be ~530±110 $H_2$ s$^{-1}$. This number is comparable with the reported specific activity of HydA1 using a similar assay (380±97 μmol $H_2$ min$^{-1}$ mg$^{-1}$), which is equivalent to a turnover frequency of ~300 $H_2$ s$^{-1}$. Thus, it seems likely that all of the HydA domains in the PSI-HydA chimeric complexes are fully active after the anaerobic induction period.

Addition of the large HydA domain to PsaC was expected to block its access to electron acceptors such as Fd. This was tested in vitro by assaying the purified protein for light-dependent reduction of low-potential electron acceptors in the presence of ascorbate, a high-potential electron donor. The PSI-HydA chimera exhibited a ~9-fold drop in light-driven reduction of cyanobacterial flavodoxin (FIG. 10A). This protein replaces Fd in cyanobacteria grown in low iron and has been shown to bind to both cyanobacterial and algal PSI in the same mode as Fd.[43] In contrast, the ability of PSI-HydA to reduce algal Fd (in a coupled assay) was reduced by only 50% (FIG. 10B). Photoreduction of $O_2$ to superoxide (i.e., Mehler reaction) was ~2-fold higher in PSI-HydA (FIG. 10C), proving that overall electron flow was not compromised by addition of the HydA domain. These assays were performed in air, where the di-iron site would be inactivated (i.e., no competition with proton reduction), but the [4Fe-4S] cluster should still be present in the HydA domain.[4] Both algal Fd and cyanobacterial flavodoxin bind the same site on PsaC involving Lys35,[44, 45] which is absent in PSI-HydA; thus, one would expect both proteins to have lost their high-affinity binding site on PSI. An explanation for the difference between their behavior with PSI-HydA is that it is the HydA domain that reduces them, rather than PsaC. The algal hydrogenase is reversible; the HydA domain binds Fd, oxidizing it when producing $H_2$, and reducing it when oxidizing $H_2$.[16] Access to the Fd-binding site of HydA2 is not expected to be blocked in the PSI-HydA chimera. Thus, Fd reduction by PSI-HydA likely proceeds via the HydA [4Fe-4S] cluster to Fd bound to its interaction site on HydA. The algal HydA domain would not be expected to bind the cyanobacterial flavodoxin very well, explaining the much lower photo reduction rate with this electron acceptor. The higher $O_2$ photo reduction rate of PSI-HydA may reflect a higher rate of $O_2$ reduction from the HydA [4Fe-4S] cluster than from the $F_A/F_B$ clusters of PsaC.

Production of $H_2$ and $O_2$ In Vivo

The ability of the hydrogenase domain in PSI-HydA to carry out $H_2$ production during dark fermentative conditions, in which Fd is largely reduced by pyruvate:Fd oxidoreductase,[46] was assessed by gas chromatography using a thermal conductivity detector (GC-TCD). Slow accumulation of $H_2$ in the headspace was observed in the cultures incubated in the dark (FIG. 4A). Hydrogen did not accumulate to detectable levels in the hydA culture until after 6 h and the rate was extremely low thereafter (8±5 nmol $H_2$ h$^{-1}$ (mg Chl)$^{-1}$). The rate of $H_2$ production by ΨH1 was roughly 60% of the WT rate [330±10 nmol $H_2$ h$^{-1}$ (mg Chl)$^{-1}$ vs. 507±30 nmol $H_2$ h$^{-1}$ (mg Chl)$^{-1}$] and remained fairly constant throughout the 6-hour experiment (see FIG. 4A). This ratio of activities is similar to the ratio of maximal $H_2$ production rate measured in these cells (FIG. 3B), indicating that the HydA2 domain in the PSI-HydA chimera is fully able to accept electrons via its normal physiological donor (Fd), consistent with the conclusion above that the HydA2 domain of the PSI-HydA chimera can bind and reduce Fd.

Illumination of the anoxic WT culture resulted in transient $H_2$ production, as observed previously.[16,47] The average rate was 28±8 μmol $H_2$ h$^{-1}$ (mg Chl)$^{-1}$ during the first hour, but rapidly dropped to negligible levels thereafter (FIG. 4B). The hydA strain did not make any detectable $H_2$. In contrast, ΨH1 produced $H_2$ continuously for 6 h, with an initial rate of ~25±6 μmol $H_2$ h$^{-1}$ (mg Chl)$^{-1}$ in the first hour and an average rate of 21±6 μmol $H_2$ h$^{-1}$ (mg Chl)$^{-1}$ over the entire time course.

Like many redox enzymes catalyzing low-potential redox reactions, the algal hydrogenase is inactivated by $O_2$. One of the reasons for sustained $H_2$ production by ΨH1 is that $O_2$ does not accumulate in the sealed culture, unlike WT or hydA (FIG. 11). To test the hypothesis that the ΨH1 strain consumes $O_2$ faster than it is produced, we measured net $O_2$ rise/fall in aerobic cultures. The compensation point is the light intensity at which $O_2$ production by PSII is matched by $O_2$ consumption. Even up to the brightest light used, the $\Psi$H1 culture with acetate never reached this point, while the culture lacking acetate required a light intensity ~5 times that of the parental strain to reach compensation. Acetate decreases net $O_2$ evolution via its effects on photosynthesis and mitochondrial respiration.[48] Light-dependent net $O_2$ evolution rates were ~35% lower in $\Psi$H1 compared to the parental strain (FIG. 12A). This could stem from either higher respiration rates or lower photosynthesis rates. In fact, we did not observe higher dark respiration rates in $\Psi$H1 (FIG. 12A). Lower rates of water oxidation could be due to either lower PSII activity or to limitations in electron flow downstream of PSII. We found that addition of phenyl-1,4-benzoquinone (PPBQ) as an artificial PSII electron acceptor resulted in similar light-dependent $O_2$ evolution rates in the two strains (FIG. 12B), consistent with the latter hypothesis. Additionally, the quantum yield of PSII drops to low values at fairly low light intensities in the light saturation curve (FIG. 12C), consistent with a highly reduced plastoquinone pool and a limitation in downstream electron flow. This is almost certainly due to the PSI-HydA chimera, whose abundance is ~7-fold lower than WT PSI. Thus, it appears that the bottleneck induced by lowered accumulation of the chimeric protein had the effect of constraining PSII $O_2$ evolution activity such that respiration and other $O_2$-consuming processes could keep up with it. While this was an unintended consequence of the PSI-HydA design, it resulted in preserving hydrogenase activity for sustained $H_2$ production. However, as many other redox enzymes are sensitive to $O_2$ and lowered abundance of chimeric proteins is a likely occurrence, this actually bodes well for the approach of fusing such enzymes to PSI.

Figures 5A, 5B, 5C, 5D:
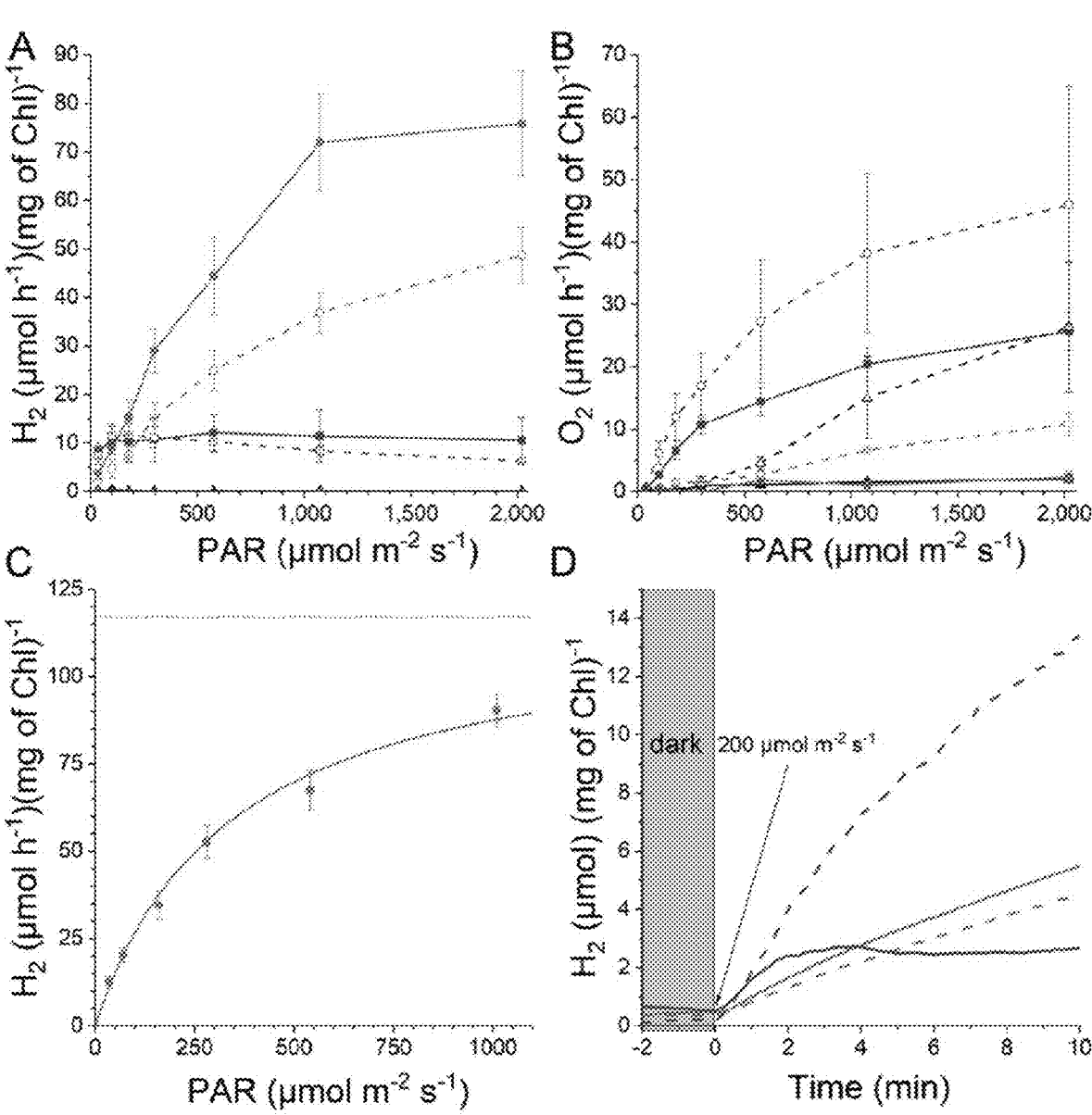

To quantify the instantaneous rates of $H_2$ and $O_2$ production by the algal cells, an online membrane inlet mass spectrometry (MIMS) technique was used to measure dissolved gasses during short illumination times (<2 min). The $\Psi$H1 cells exhibited a significantly higher $H_2$ evolution rate than WT at photon fluxes above ~300 $\mu$mol m$^{-2}$ s$^{-1}$ and did not saturate until over ~1000 $\mu$mol photons m$^{-2}$ s$^{-1}$ (FIG. 5A). In stark contrast, $H_2$ production by WT cells saturated at lower light intensities (~100 $\mu$mol photons m$^{-2}$ s$^{-1}$) with a maximum rate of 11±4 $\mu$mol $H_2$ h$^{-1}$ (mg Chl)$^{-1}$, regardless of the presence of acetate. There was no detectable $H_2$ production by hydA cells. For $\Psi$H1 cells, the highest observed rates were 76±11 or 49±6 $\mu$mol $H_2$ h$^{-1}$ (mg Chl)$^{-1}$ in media with or without acetate, respectively. To eliminate the effect of $O_2$ inhibition on hydrogenase activity, we added glucose, glucose oxidase, and catalase to the medium to scavenge $O_2$.[16] With saturating light, the highest observed rate was 90±5 $\mu$mol $H_2$ h$^{-1}$ (mg Chl)$^{-1}$, representing a ~20% improvement (FIG. 5C). Fitting of the data to a hyperbolic curve allowed us to estimate $V_{max}$ to be 120 $\mu$mol $H_2$ h$^{-1}$ (mg Chl)$^{-1}$ with half-saturation at 340 $\mu$mol photons m$^{-2}$ s$^{-1}$. (In order to compare this maximal rate to those of chemotrophs or abiotic materials, it is equivalent to 2.7 mmol $H_2$ h$^{-1}$ per g dry weight of cells.) To put this in context, such a strain could perform well even on a cloudy day (~600 $\mu$mol m$^{-2}$ s$^{-1}$) and still reach saturation on a sunny day (≥2000 $\mu$mol m$^{-2}$ s$^{-1}$).[49] Although the algal [FeFe] hydrogenase is known to be irreversibly inhibited by $O_2$ in a matter of seconds[50] and PSII is producing $O_2$ in the same membrane, $O_2$ scavenging only improved $H_2$ production in the $\Psi$H1 culture by 20%. This demonstrates that keeping the enzyme in its cellular context allows maintenance of its activity for much longer periods than might be expected.

We now turn to the possible sinks in $\Psi$H1 cells for electrons from PSII. A major motivation for our design was to intercept electrons from the PETC before they reached the Fd pool. Examination of FIG. 5 allows one to conclude that the majority of these electrons are used to make $H_2$ in the $\Psi$H1 strain. In the absence of acetate, maximal net $O_2$ production in the WT culture is ~45 $\mu$mol $O_2$ h$^{-1}$ (mg Chl)$^{-1}$. Although we do not know the respiration rate in these short-term experiments, it cannot be high, as the cultures start out anoxic before illumination. Moreover, we know that PSII is much more constrained in $\Psi$H1 cells than in WT cells. Therefore, we would not expect the rate of gross $O_2$ production by PSII in the $\Psi$H1 culture to be higher than ~50 $\mu$mol $O_2$ h$^{-1}$ (mg Chl)$^{-1}$, leading to an estimated maximal $H_2$ production rate ~100 $\mu$mol $H_2$ h$^{-1}$ (mg Chl)$^{-1}$, if all electrons from water oxidation were used to produce $H_2$. In the presence of acetate, maximal net $H_2$ production in the $\Psi$H1 culture was ~75 $\mu$mol $H_2$ h$^{-1}$ (mg Chl)$^{-1}$. To test this hypothesis further, we assessed the impact of competition with $CO_2$ fixation by using a phosphoribulokinase inhibitor (glycolaldehyde) to block the CBB cycle.[51] In the WT culture, the $H_2$ evolution rate quickly dropped after ~1 minute, decreasing over 10-fold from the peak rate within 5 minutes (FIG. 5D). This drop was largely due to the activation of the CBB cycle, as addition of glycolaldehyde resulted in a much lower drop (~50%) in H2 evolution, which persisted during the experiment (10 min), as previously reported.[16] In contrast, the $\Psi$H1 culture exhibited very stable $H_2$ production rates over the time course, and a ~20% decrease in $H_2$ evolution rate was seen after addition of glycolaldehyde. Nevertheless, we found that the $\Psi$H1 strain was able to grow photoautotrophically, albeit much more slowly than strains containing WT PSI, and only if the culture was first rendered anoxic (FIG. 14). These results are consistent with the hypothesis that PSI-HydA reduces Fd in vivo poorly, and directs most, but not all, of the electrons from the PETC to proton reduction, at least under high light (discussed further below). We also found that cyclic electron flow around PSI was negligible in $\Psi$H1 cells (FIG. 15), consistent with this idea. Thus, both linear and cyclic electron transport pathways are strongly affected in $\Psi$H1 cells, demonstrating that photosynthetic electron flow has effectively been redirected in these cells by replacement of PSI with PSI-HydA. When one considers that the amount of PSI is ~7-fold lower (FIG. 3A) and the total amount of hydrogenase activity is ~2-fold lower (FIG. 3B) in the $\Psi$H1 strain compared to WT, and yet the instantaneous light-saturated $H_2$ production rate is almost 7-fold higher than WT in this strain, it is difficult to imagine how this could be, unless electrons from PSI were being directly delivered to the hydrogenase active site, as intended by the chimeric protein design.

We tested the utility of this system for long-term $H_2$ production. After anoxia was imposed in a sealed bottle, the culture produced $H_2$ continuously for 5 days at an average rate of 14.0±1.7 $\mu$mol $H_2$ h$^{-1}$ (mg Chl)$^{-1}$ (FIG. 13A). A similar experiment was run without imposing anoxia, and within 2 days the $\Psi$H1 culture had become hypoxic (~4% $O_2$ in the headspace) and started producing $H_2$ (FIG. 13B). We also set up long-term experiments using a PBR in turbidostat mode, which was flushed continuously with argon. Hydrogen was monitored in the efflux gas, allowing calculation of the rate of $H_2$ production by the culture. Cultures were maintained at high density (~30 mg Chl L$^{-1}$) under continuous illumination (600 $\mu$mol photons m$^{-2}$ s$^{-1}$). The production rate was 86.6±2.4 mL $H_2$ d$^{-1}$ per L culture (n=3). These rates, whether in sealed bottles or in a PBR, are at least comparable to rates reported in this species using the endogenous hydrogenases in concert with other methods to lower steady-state $O_2$ levels and/or direct electrons to $H_2$ production.[8] In order to compare this rate to $H_2$ production rates using chemotrophs or abiotic materials, we normalized to dry weight of cells rather than Chl to obtain a rate of $164\pm5$ mL $H_2$ $d^{-1}$ $g^{-1}$. The light-to-hydrogen conversion efficiency of $\Psi$HI cultures reached 1.75% under the best conditions (i.e., short term with acetate and enforced anoxia, using 6.65 W $m^{-2}$ of 630 nm photons), which is over 10% of the theoretical maximum. While this is encouraging, we are still far from realizing the full potential of the system on a long-term basis, as light-to-hydrogen conversion efficiency was only about 0.12% in the aforementioned PBR experiment.

It is somewhat surprising that marrying two very different proteins resulted in such an active chimeric protein. Using the maximal rate estimated from the MIMS experiment, and taking into account the PSI-HydA cellular abundance, one arrives at a H2 production rate of ~170 $H_2$ s–1 for each PSI-HydA (i.e., ~340 electrons s–1). This is in line with previously reported electron throughput rates for PSI.[52] It also compares favorably with the PSI-hydrogenase assembly created in vitro that is currently the best in vitro $H_2$ photoproduction device (~50 $H_2$ $s^{-1}$).[53] In both cases, the overall throughput is likely limited by electron donation to $P_{700}$. The PSI-HydA chimera may have an advantage there, as algal Pc can reduce $P_{700}$ in <50 $\mu$s.[54] Based on these calculations, we conclude that the PSI-HydA chimera reported here is actually a very efficient light driven proton photoreduction machine, capable of producing a dihydrogen every ~6 ms in vivo.

It is important to realize that the addition of the hydrogenase domain to PSI has created a photosystem that is fundamentally different from PSI, which is a type I reaction center that oxidizes and reduces 1-electron carriers. The PSI-HydA chimera requires 2 electrons to produce 1 $H_2$. Thus, it first needs to accumulate one electron on the HydA domain; after re-reduction of $P_{700}^+$ by plastocyanin and excitation of the reaction center, a second electron can be sent to the hydrogenase active site, resulting in reduction of 2 protons to a dihydrogen molecule. This is more akin to the action of a type II photochemical reaction center, which accumulates 2 electrons to reduce a quinone to quinol (also consuming 2 protons), although in this case the product is a gaseous molecule. Thus, it is not an overstatement to say that we have created a novel photochemical reaction center by fusing hydrogenase to PSI. It is also important to consider the competition between reduction of Fd (requiring 1 electron) and protons (requiring 2 electrons). The longer the delay between the first and second electron arriving at the H-cluster, the more time that Fd has to bind to the HydA domain and "steal" the electron. This almost certainly explains the very high light flux required to saturate $H_2$ production in the $\Psi$H1 cultures (FIG. 5A), as higher light intensities will result in shorter average delays between consecutive excitations of PSI-HydA. Thus, as such a culture went through a day-night cycle, it would be biased towards Fd reduction at the beginning and end of the day, allowing it to fulfill basic physiological needs, but be biased towards $H_2$ production in the middle of the day, storing some of the energy of the extra photons as molecular hydrogen.

Future efforts to increase $H_2$ production with this system will focus on use of more $O_2$-tolerant hydrogenases. This would in turn allow use of PSI-HydA chimeras that accumulated to higher levels. While that would increase $H_2$ production, it would allow more $O_2$ production. However, as long as the steady-state level of $O_2$ present in the flow PBR system were not higher than the tolerance of the hydrogenase domain, the system should be able to produce $H_2$ continuously at a rate significantly higher than reported here. It should also be possible to modulate the partitioning of electrons between reduction of Fd and protons by modifying the Fd binding site of the HydA domain.

Use of the PSI-HydA chimera offers at least 4 advantages: (1) it constitutively expresses the chimeric protein; (2) it directs the majority of electrons from water oxidation to $H_2$ production; (3) it constrains $O_2$ evolution from PSII, preserving hydrogenase activity for sustained $H_2$ production over many days, obviating the need to use nutrient deprivation, PSII inhibitors or mutations; and (4) it preserves the proton pumping and ATP production carried out by the PETC, thus maintaining cell viability. By rewiring photosynthesis to deliver electrons from PSI directly to hydrogenase—thus cutting out the Fd 'middleman'—one is no longer at the mercy of cellular metabolic networks. With the system entirely encoded by the algal chloroplast genome, the use of directed evolution techniques to improve the system also becomes possible. Perhaps more important than this particular example, however, is the discovery of a site in PSI that allows in-frame fusion of a protein to intercept electors from PSI. The $F_A/F_B$clusters of PSI are at a lower reduction potential than any soluble electron carrier in the cell (e.g. Fd, NADPH, thioredoxin). This opens the ability to drive novel redox chemistries not native to plants and algae at high flux by using a large fraction of the electrons from water-splitting and the PETC.

References

1 S. S. Veeravalli, S. R. Shanmugam, S. Ray, J. A. Lalman and N. Biswas, in Advanced Bioprocessing for Alternative Fuels, Biobased Chemicals, and Bioproducts, ed. M. Hosseini, Woodhead Publishing, Cambridge, UK, 2019, vol. 15, pp. 289-312.

2 K. D. Swanson, M. W. Ratzloff, D. W. Mulder, J. H. Artz, S. Ghose, A. Hoffman, S. White, O. A. Zadvornyy, J. B. Broderick, B. Bothner, P. W. King and J. W. Peters, J. Am. Chem. Soc., 2015, 137, 1809-1816.

3 N. Nelson and A. Ben-Shem, Nat. Rev. Mol. Cell Biol., 2004, 5, 971.

4 D. W. Mulder, E. S. Boyd, R. Sarma, R. K. Lange, J. A. Endrizzi, J. B. Broderick and J. W. Peters, Nature, 2010, 465, 248-251.

5 M. C. Posewitz, P. W. King, S. L. Smolinski, L. Zhang, M. Seibert and M. L. Ghirardi, J. Biol. Chem., 2004, 279, 25711-25720.

6 B. Ghysels, D. Godaux, R. F. Matagne, P. Cardol and F. Franck, PLoS One, 2013, 8, e64161.

7 G. Torzillo, A. Scoma, C. Faraloni and L. Giannelli, Crit. Rev. Biotechnol., 2015, 35, 485-496.

8 S. Z. To'th and I. Yacoby, Trends Biotechnol., 2019, 37, 1159-1163.

9 I. Yacoby, S. Pochekailov, H. Toporik, M. L. Ghirardi, P. W. King and S. Zhang, Proc. Natl. Acad. Sci. U.S.A., 2011, 108, 9396-9401.

10 D. Nikolova, C. Heilmann, S. Hawat, P. Ga"belein and M. Hippler, Photosynth. Res., 2018, 137, 281-293.

11 P. Decottignies, P. Lemarechal, J. P. Jacquot, J. M. Schmitter and P. Gadal, Arch. Biochem. Biophys., 1995, 316, 249-259.

12 P. Decottignies, V. Flesch, C. Ge'rard-Hirne and P. LeMare'chal, Plant Physiol. Biochem., 2003, 41, 637-642.

13 M. Winkler, S. Kuhlgert, M. Hippler and T. Happe, J. Biol. Chem., 2009, 284, 36620-36627.

14 G. Vonabendroth, S. Stripp, A. Silakov, C. Croux, P. Soucaille, L. Girbal and T. Happe, Int. J. Hydrogen Energy, 2008, 33, 6076-6081.

15 T. Happe and J. D. Naber, Eur. J. Biochem., 1993, 214, 475-481.

16 Y. Milrad, S. Schweitzer, Y. Feldman and I. Yacoby, Plant Physiol., 2018, 177, 918-926.

17 S. Kosourov, M. Jokel, E. M. Aro and Y. Allahverdiyeva, Energy Environ. Sci., 2018, 1-2.

18 K. Brettel, Biochim. Biophys. Acta, Bioenerg., 1997, 1318, 322-373.

19 M. Forestier, P. King, L. Zhang, M. Posewitz, S. Schwarzer, T. Happe, M. L. Ghirardi and M. Seibert, Eur. J. Biochem., 2003, 270, 2750-2758.

20 K. Reifschneider-Wegner, A. Kanygin and K. E. Redding, Int. J. Hydrogen Energy, 2014, 39, 3657-3665.

21 A. Sawyer, Y. Bai, Y. Lu, A. Hemschemeier and T. Happe, Plant J., 2017, 90, 1134-1143.

22 L. A. Kelley, S. Mezulis, C. M. Yates, M. N. Wass and M. J. E. Sternberg, Nat. Protoc., 2015, 10, 845-858.

23 D. Kozakov, D. R. Hall, B. Xia, K. A. Porter, D. Padhorny, C. Yueh, D. Beglov and S. Vajda, Nat. Protoc., 2017, 12, 255.

24 A. Fiser, R. K. G. Do and A. S̆ali, Protein Sci., 2000, 9, 1753-1773.

25 N. Fischer, P. Se´tif and J. D. Rochaix, Biochemistry, 1997, 36, 93-102.

26 J. E. Meuser, S. D'Adamo, R. E. Jinkerson, F. Mus, W. Yang, M. L. Ghirardi, M. Seibert, A. R. Grossman and M. C. Posewitz, Biochem. Biophys. Res. Commun., 2012, 417, 704-709.

27 N. Fischer, O. Stampacchia, K. Redding and J.-D. Rochaix, Mol. Gen. Genet., 1996, 251, 373-380.

28 G. Gulis, K. V. Narasimhulu, L. N. Fox and K. E. Redding, Photosynth. Res., 2008, 96, 51-60.

29 Y. Li, M.-G. Lucas, T. Konovalova, B. Abbott, F. Mac-Millan, A. Petrenko, V. Sivakumar, R. Wang, G. Hastings, F. Gu J. van Tol, L.-C. Brunel, R. Timkovich, F. Rappaport and K. Redding, Biochemistry, 2004, 43, 12634-12647.

30 J. Kropat, A. Hong-Hermesdorf, D. Casero, P. Ent, M. Castruita, M. Pellegrini, S. S. Merchant and D. Malasarn, Plant J., 2011, 66, 770-780.

31 R. J. Porra, W. A. Thompson and P. E. Kriedemann, Biochim. Biophys. Acta, Bioenerg., 1989, 975, 384-394.

32 M. Byrdin, S. Santabarbara, F. Gu, W. V. Fairclough, P. Heathcote, K. Redding and F. Rappaport, Biochim. Biophys. Acta, Bioenerg., 2006, 1757, 1529-1538.

33 O. Liran, R. Semyatich, Y. Milrad, H. Eilenberg, I. Weiner and I. Yacoby, Plant Physiol., 2016, 172, 264-271.

34 S. Kosourov, M. Jokel, E. M. Aro and Y. Allahverdiyeva, Energy Environ. Sci., 2018, 11, 1431-1436.

35 P. Jordan, P. Fromme, H. T. Witt and O. Klukas, et al., Nature, 2001, 411, 909.

36 C. H. Chang, P. W. King, M. L. Ghirardi and K. Kim, Biophys. J., 2007, 93, 3034-3045.

37 O. Ostersetzer and Z. Adam, Plant Cell, 1997, 9, 957-965.

38 P. Se´tif, N. Fischer, B. Lagoutte, H. Bottin and J. D. Rochaix, Biochim. Biophys. Acta, Bioenerg., 2002, 1555, 204-209.

39 D. J. Cashman, T. Zhu, R. F. Simmerman, C. Scott, B. D. Bruce and J. Baudry, J. Mol. Recognit., 2014, 27, 597-608.

40 Y. Takahashi, M. Goldschmidt-Clermont, S. Y. Soen, L. G. Franze´n, J. D. Rochaix, L. G. Franzen and J. D. Rochaix, EMBO J., 1991, 10, 2033.

41 E. M. Shepard, F. Mus, J. N. Betz, A. S. Byer, B. R. Duffus, J. W. Peters and J. B. Broderick, Biochemistry, 2014, 53, 4090-4104.

42 H. Witt, E. Bordignon, D. Carbonera, J. P. Dekker, N. Karapetyan C. Teutloff, A. Webber, W. Lubitz and E. Schlodder, J. Biol. Chem., 2003, 278, 46760-46771.

43 P. Se´tif, Biochim. Biophys. Acta, Bioenerg., 2001, 1507, 161-179.

44 N. Fischer, EMBO J., 1998, 17, 849-858.

45 K. Meimberg, N. Fischer, J.-D. Rochaix and U. Mu¨hlenhoff, Eur. J. Biochem., 1999, 263, 137-144.

46 J. Noth, D. Krawietz, A. Hemschemeier and T. Happe, J. Biol. Chem., 2013, 288, 4368-4377.

47 O. Ben-Zvi, E. Dafni, Y. Feldman and I. Yacoby, Biotechnol. Biofuels, 2019, 12, 266.

48 S. P. Chapman, C. M. Paget, G. N. Johnson and J.-M. Schwartz, Front. Plant Sci., 2015, 6, 474.

49 L. Wang, W. Gong, A. Lin and B. Hu, Int. J. Biometeorol., 2014, 58, 1711-1720.

50 D. L. Erbes, D. King and M. Gibbs, Plant Physiol., 1979, 63, 1138-1142.

51 R. C. Sicher, in Advances in Photosynthesis Research: Proceedings of the VIth International Congress on Photosynthesis, Brussels, Belgium, Aug. 1-6, 1983, ed. C. Sybesma, Springer, Netherlands, Dordrecht, 1984, pp. 413-416.

52 H. Takahashi, S. Clowez, F.-A. Wollman, O. Vallon and F. Rappaport, Nat. Commun., 2013, 4, 1954.

53 C. E. Lubner, A. M. Applegate, P. Knorzer, A. Ganago, D. A. Bryant, T. Happe and J. H. Golbeck, Proc. Natl. Acad. Sci. U.S.A., 2011, 108, 20988-20991.

54 S. Santabarbara, K. E. Redding and F. Rappaport, Biochemistry, 2009, 48, 10457-10466.

55 H. Bohme, Eur. J. Biochem., 1978, 83, 137-141.

56 D. Weis, G. Schneider, B. Niemann, P. Guttmann, D. Rudolph and G. Schmahl, Ultramicroscopy, 2000, 84, 185-197.

57 J. E. W. Polle, J. R. Benemann, A. Tanaka and A. Melis, Planta, 2000, 211, 335-344.

S. Kuhlgert, F. Drepper, C. Fufezan, F. Sommer and M. Hippler, Biochemistry, 2012, 51, 7297-7303.

P. Marco, M. Kozuleva, H. Eilenberg, Y. Mazor, P. Gimeson, A. Kanygin, K. Redding, I. Weiner and I. Yacoby, Biochim. Biophys. Acta—Bioenerg., 2018, 1859, 234-243.

J. Zhao, R. Li and D. A. Bryant, Anal. Biochem., 1998, 264, 263-270.

K. Meimberg and U. Muhlenhoff, Photosynth. Res., 1999, 61, 253-267.

J. Alric, J. Lavergne and F. Rappaport, Biochim. Biophys. Acta—Bioenerg., 2010, 1797, 44-51.

B. Genty, J.-M. Briantais and N. R. Baker, Biochim. Biophys. Acta—Gen. Subj., 1989, 990, 87-92.

N. Fischer, P. Setif and J. D. Rochaix, J. Biol. Chem., 1999, 274, 23333-23340.

K. Brettel and W. Leibl, Biochim. Biophys. Acta—Bioenerg., 2001, 1507, 100-114.

K. Brettel, Biochim. Biophys. Acta—Bioenerg., 1997, 1318, 322-373.

R. Jordan, U. Nessau and E. Schlodder, in Photosynthesis: Mechanisms and Effects, ed. G. Garab, Springer Netherlands, Dordrecht, 1998, pp. 663-666.

Example 2—In Vivo Fusion of Photosystem I (PS1) and Algal Hydrogenase 1

We have previously demonstrated that a photosystem I-hydrogenase chimera, in which light-driven charge separation in photosystem I feeds electrons directly into the hydrogenase domain, allowing for prolonged photobiological hydrogen production. Here we describe a new PSI-hydrogenase chimera using HydA1, the more abundant and physiologically active endogenous hydrogenase of *Chlamydomonas reinhardtii*. The resulting transformants in a *C. reinhardtii* strain lacking endogenous hydrogenases showed that PSI-HydA1 is active and accumulates ~5 times more chimeric protein than the previous PSI-HydA2 chimera. The majority of chimeric hydrogen production activity can be restored after complete inactivation by oxygen without requiring new synthesis of PSI or the PsaC-HydA1 polypeptide. The PSI-HydA1 chimera reduces ferredoxin in vivo to such an extent that it can drive the Calvin-Benson-Bassham cycle, leading to sufficiently high $O_2$ levels that eventually inactivate the hydrogenase, as hypothesized earlier.

Experimental Design

Design of PsaC-HydA1 chimera: A complete annotated protein sequence of PsaC-HydA1 is shown in FIG. 24 (SEQ ID NO: 2). The insertion site of the hydrogenase domain and modifications to PsaC protein sequence were the same as previously described[27]. Outer loop of PsaC (residues 32-36) was split open and DGCKA (SEQ ID NO: 14) residues removed. A N-terminal of modified version of HydA1 sequence was linked to PsaC-Trp31 via double glycine residue. A C-terminal of modified HydA1 sequence (Gly489) was linked to PsaC-Ala36. Modifications to HydA1 sequence are outlined below.

The transit peptide sequence of HydA1 (first 56 amino acids[28]) was removed and the remaining unstructured region (AAPAAEAPLS; SEQ ID NO: 15) leading up to the first α-helix H67-L75 was replaced with the sequence used in the psaC-hydA2 construct (FIG. 24, highlighted in magenta). The last 8 (non-conserved) amino acids of HydA1 were also removed (FIG. 25). Sequence alignments of HydA1 and HydA2 (SEQ ID NO: 3 and 4, respectively; FIG. 25) verified a close match to the design of the PsaC-HydA2 construct (SEQ ID NO: 1).

For modeling the PsaC-HydA1 chimera, the crystal structure of HydA1 (3LX4) was used as the ligand and PsaA, PsaB, PsaC (D32-K35 residues removed) and PsaF subunits of *C. reinhardtii* PSI (6IJJ[29]) were used as a receptor in docking with ClusPro2. Unstructured terminal residues (6 N-terminal residues only) were removed from the ligand by the ClusPro2 algorithm prior to docking. Also, distance restraints of 1-25 Å were placed between the outermost cysteine of the $F_B$ iron-sulfur cluster (Cys14) and the outermost cysteines of the H-cluster: cysteines 185 or 377 in 3LX4 (corresponding to cysteines 199 or 391 in PsaC-HydA1, respectively). The most plausible model was chosen based on the ClusPro2 energy minimization algorithm. Linking regions between PsaC and HydA1 domains were modeled with the help of the Robetta web server by uploading docked coordinates into their comparative modeling option[30]. The PsaD subunit (6IJJ, chain D) was aligned as in native PSI. PyMOL[31] was used for generation of final images as well as structure alignments.

For modeling ferredoxin docking to the PSI-HydA1 chimera, ferredoxin 1 of the 2N0S model[32] was used as a ligand and PsaA, PsaB, PsaC-HydA1, PsaD, and PsaF of our model as receptor in ClusPro2 server. A single distance restraint of 1-25 Å between Cys42 of ferredoxin and Cys391 of PsaC-HydA1 were used.

Generation of algal mutants bearing chimeric photosystem I-hydrogenase: All transformations were carried out in hydA strain (mt⁻hydA1-1, hydA2-1)[33] that lacks both endogenous hydrogenases via DNA-coated particle bombardment[27].

PCR for homoplasmy confirmation: PsaC-HydA1 homoplasmy confirmation was performed with flanking primers (PsaC5': TAATATGGAGATGACATATTTAG (SEQ ID NO: 10) and PsaC3': GATCTCACCAAGATACTCCC (SEQ ID NO: 11)) on 100 ng of genomic DNA as previously described[27], with minor modifications. Detection limit of psaC was tested by making a series of dilutions of genomic DNA of parental strain (containing psaC gene) into ΨH2 genomic DNA (containing psaC-HydA2 gene known to be homoplasmic).

Growth conditions: Alga was routinely grown on Tris-acetate-phosphate (TAP) medium with revised mineral nutrient supplement[34] as previously described[27].

For growth assay on plates, 10 μL (~$10^4$ cells) cells resuspended in the same buffer as the corresponding agar plate were spotted and let dry for 10 min. Then, plates were either scaled with parafilm to prevent further drying or placed in the anaerobe pouch (for high $CO_2$/anoxia conditions). 1.4% agar TAP or TBP (Tris-bicarbonate phosphate) plates were used. TBP containing plates were prepared by replacing acetate (16.6 mM) with sodium bicarbonate (25 mM, pH 7.0). Growth assay was performed under continuous white fluorescent light (70 μmol m⁻² s⁻¹). Plates were photographed on the second and $7^{th}$ day of growth.

Chlorophyll (Chl) measurement: Chl a+b concentrations were determined by method of Porra in 80% acetone[35].

Thylakoids and PSI preparation; Cells were grown in TAP to mid-to-late log phase in 4 L flasks with aeration and stirring under ambient room light (<5 μmol m² s⁻¹ white fluorescent). Thylakoids were prepared as previously described[36] with minor modifications. Cells harvested at 3500×g at 4° C. for 10 min. The pellet was washed with buffer H1 (25 mM HEPES-KOH, 5 mM $MgCl_2$, 0.3 M sucrose, pH 7.5), flash-frozen in liquid nitrogen and stored at −80° C. Further steps were done in the dark. Cells resuspended in H1+1 mM phenylmethane sulfonyl fluoride to ~$4×10^8$ cells ml⁻¹ were broken by French press applying ~1.7 tons of pressure or Branson Sonifier S-450 using amplitude 3 (50% duty cycle) for 2 min ON followed by 2 min OFF and repeated 3 times under temperature control (4° C.). The membranes were pelleted at 20000×g for 10 min and washed with buffer H2 (5 mM HEPES-KOH, 10 mM EDTA, 1.8 M sucrose, pH 7.5). The washed pellet was resuspended in buffer H3 (5 mM HEPES-KOH, 10 mM EDTA, 1.8 M sucrose, pH 7.5) and overlaid with buffer H4 (1.3 M sucrose) and H5 (0.5 M sucrose) in a gradient tube. After 1 h of centrifugation (SW-28 rotor at 112400×g) the upper green band formed between 0.5 M and 1.3 M sucrose layers was pooled with the lower band (1.3 M/1.8M sucrose). Purified membranes were centrifuged (90000×g for 30 min) and resuspended in H6+20% glycerol for storage at −80° C.

Anoxic PSI-HydA1 isolation: As previously described for PSI-HydA2[27]. Since PSI was not tagged, we used our sucrose gradient protocol for anoxic PSI isolation (adding ~2 mM sodium dithionite at every step).

Laser-flash spectroscopy: Our experimental setup was very similar to what is described in[27]. Thylakoids (~60 μg Chl mL⁻¹ in 25 mM HEPES-KOH, pH 7.5, 5 mM sodium ascorbate) or PSI particles (~6 μg Chl mL⁻¹ in 25 mM tricine-KOH, 300 mM KCl pH 8.0, 10% glycerol, 0.03% β-DDM, 5 mM sodium ascorbate) were kept on ice in the dark before measurements. Absorbance changes at 696 nm were triggered by ~20-25 mJ excitation flash (6 ns) generated by a frequency-doubled Nd/YAG laser (532 nm) and probed with weak LED pulses (10 μs) using JTS-10 (Bio-Logic) spectrophotometer. Once saturation of $P_{700}^+$ signal was established, its decay was recorded, and background transient subtracted. Background transient was collected by running the same sequence with laser shutter closed. It consists of actinic effects of probing light and electronic artifact (due to changing collecting rates).

In vitro hydrogenase activity: This assay is similar to what we used before[27]. Cells were resuspended in TAP at ~30 μg Chl mL$^{-1}$. 0.2 mL of cell suspension was taken at various times during anaerobic adaptation and mixed with pre-sparged (Ar), pre-warmed (37° C.) reaction buffer (100 mM Tris-HCl, pH 7.3, 1 M NaCl, 8 mM methyl viologen, 0.2% Triton X-100, 16 mM sodium dithionite). After 10-30 min of incubation at 37° C. with agitation, headspace of the vial was probed with gas chromatography. For inhibition with chloramphenicol (CAM), a 50 mg/mL CAM stock solution in ethanol was freshly prepared.

Gas chromatography (GC) measurements: A model SRI 310 gas chromatograph with thermal conductivity detector and 5 Å molecular sieve prepacked column (3 ft long) was used in all measurements. Gas tight syringes (1700 series) with non-coring needles were used for probing headspace.

Western blotting: Immunoblots were performed as described in[27]. Solubilized thylakoids were loaded on the basis of the same $P_{700}^+$ photobleaching (1.41 pmol) or the same Chl (2 μg) amounts.

Membrane inlet mass spectrometry (MIMS) measurements of $H_2$, $O_2$ and $CO_2$ in vivo: Cells were washed once with TP media, then resuspended in either TP or TAP media to 15 μg/mL of total Chl. Anaerobic adaption was done in 25-mL Wheaton glass bottles covered with aluminum foil. Cell suspensions were sparged with either argon or nitrogen at 100 mL min$^{-1}$ for 10 min, followed up by at least 3 hours of agitation in the dark. Five mL of suspended cells were injected into a continuously purged (500 mL min$^{-1}$ $N_2$) custom-built glass cuvette (5 mL) with 4 ports on top. 2 mM sodium bicarbonate in 50 mM HEPES-KOH (pH 7.2), 10 μM DCMU in DMSO and 40 mM glycolaldehyde (GA) final concentrations were added where indicated followed up by removing purging line and incubating with continuous stirring in the dark for ~5 minutes. Cuvette was kept at 24° C. and stirring via Peltier temperature programmer (PTP-1 by Perkin Elmer). Red LED lights (Hansatech instruments) of various intensity were used to illuminate the cuvette.

QMG 220 M1 Prisma Plus compact mass spectrometer (Pfeiffer vacuum) equipped with gas-tight ion source was connected to a home-built membrane inlet system. The system was made of ¼" OD stainless steel tubing (0.035" wall thickness) that included a loop for cold trap, a port for a pressure gauge, an external vacuum line port and a narrowing to 1/16" OD stainless steel probe at the end where silicone-based polymer tube was attached. Membrane inlet consisted of 7 mm long tube supported by rings on the inside and ended with 5 mm long silicone rubber tapered plug. A mixture of dry ice and ethanol was used for the cold trap in all experiments.

Ion currents (m/z 2, m/z 32, m/z 44) were collected with a 0.5 s dwelling time and used for $H_2$, $O_2$ and $CO_2$ determination, respectively. Standards were made by sparging cell-free buffers either with a 1% $H_2$ (balance $N_2$) standard (Matheson) or air at the known pressure until equilibrium was reached. Rates of gas consumption by the mass spectrometer were calculated after removing sparging from cell free buffers as described elsewhere[38].

In vivo dissolved $O_2$ measurements with FireSting-$O_2$: Cells were grown on TAP to mid-to-late log phase. Then, they were resuspended in TAP+25 mM sodium bicarbonate (freshly made) to ~20 (μg of Chl) mL$^{-1}$ and briefly sparged with air to saturate with oxygen. Once placed in the cuvette with continuous stirring, $O_2$ concentration was measured with FireSting-$O_2$ (Pyroscience) probe for dark respiration (5 min) followed by 5 min of continuous red light (~1435 μmol PAR m$^{-2}$ s$^{-1}$). Gross oxygen rate was calculated as Light (net) minus dark rates.

In vivo $P_{700}^+$ recovery measurements, chlorophyll fluorescence measurements and quantum yield of PSII: Cells were collected during early log phase, centrifuged (3500×g for 5 min) and resuspended in 10 mM sodium phosphate (pH 7.0), 2 mM sodium bicarbonate and 20% Ficoll™ PM400 (GE Healthcare) to ~30 μg/mL Chl ($P_{700}^+$) or ~9 μg Chl mL$^{-1}$ (fluorescence). Cells were dark adapted for 5 min before taking each measurement. (During dark periods, samples were briefly sparged with air to prevent development of anoxia.) $P_{700}^+$ signal was measured with JTS-10 as previously described[27]. Fluorescence emission from Chl was measured with the JTS-10 Fluo59 accessory. A saturating pulse (80 ms, 8 mmol photons m$^{-2}$ s$^{-1}$, 520 nm) was used to obtain $F_{max}$, measured 170 μs after the pulse. The steady-state fluorescence parameter ($F_s$) was measured after 2 minutes of illumination (520 nm) with actinic light of variable intensities. Quantum yields of PS II ($\Phi_{(II)}$) were calculated as described[39].

Results and Discussion

Chimeric protein making: Based on our previous work with the PsaC-HydA2 chimera and the close similarity of the two endogenous hydrogenases of *C. reinhardtii*, we designed a PsaC-HydA1 construct that has 78% identity and 88% similarity to the PsaC-HydA2 chimera (FIG. 25). We used the same principles as we had used before (e.g., PsaC and HydA domains must fold, distance between $F_B$ and H-cluster should be close enough for electron transfer) to come up with a plausible model of the chimeric photosystem I-hydrogenase (FIG. 16).

The psaC-hydA1 gene was introduced into the chloroplast genome of the hydA1-1 hydA2-1 strain via biolistic transformation followed up by homologous recombination as previously described for the psaC-hydA2 gene[27]. After several passages on selective plates, transformants were screened for homoplasmy (i.e., all copies of the chloroplast genome contained the same psaC-hydA1 in place of psaC; see FIG. 27). Sequencing of PCR products was performed to verify proper gene insertion. For brevity, the hydA1-1 hydA2-1 strain will be referred to as hydA, and the psaC-hydA1 transformant will be called ΨH2.

Expression of PsaC-HydA1 was verified by immunoblots using solubilized thylakoid membranes prepared from aerobically grown cells. We measured the amount of photoactive PSI in WT and ΨH2 thylakoids (as described below) and loaded equal amounts of PSI reaction centers. When probed with anti-PsaC antibodies (FIG. 17A), a band of ~10 kDa was visualized in the parental hydA strain ("WT" in FIG. 17), as expected for PsaC. In the ΨH2 sample, a band of ~50 kDa was seen, which is comparable in size to the predicted PsaC-HydA1 chimeric polypeptide (54.8 kDa). No wild-type PsaC was detected in ΨH2. When probed with anti-HydA antibodies (FIG. 17A), there were no bands detected in the WT sample, as expected. A ~50-kDa band was detected in the ΨH2 sample, suggesting that PsaC-HydA1 was expressed in the mutant and assembled into PSI complexes. When solubilized thylakoids were loaded on the basis of equal Chl and probed them with anti-PsaA antibodies, we found that the amount of PsaA in membrane from the ΨH2 strain was ~64% that of the WT strain (FIG. 17B).

Spectroscopic characterization of the PSI-HydA1 chimera: The light-driven generation of a stable charge-separated state in PSI can only be achieved if all core subunits carrying electron transfer cofactors are functional and properly assembled into the PSI complex. Since we replaced the PsaC subunit, which coordinates the terminal iron sulfur clusters of PSI, with the PsaC-HydA1 chimera, we wanted to see if it is still capable of assembling into PSI and whether we could detect the additional iron sulfur cluster within the H-cluster of hydrogenase.

Thylakoid membranes prepared from aerobically grown cultures were used as samples in a $P_{700}$ photobleaching experiment. The amplitude of the $P_{700}^+$ signal from ΨH2 thylakoids after a saturating laser flash was ~76% of the parental strain (FIG. 18A). The dark recovery kinetics (FIG. 18A inset) could be modeled with a biphasic exponential decay function. The faster component exhibited the characteristic time due to charge recombination from $(F_AF_B)^-/P_{700}^+$ (123±9 ms, see Table 4). This demonstrates that the PsaC-HydA1 chimeric polypeptide must be co-assembled with PSI. The larger amplitude (71%) of the slow phase (>3 s) is assigned to slow re-reduction of $P_{700}^+$ by ascorbate in those PSI complexes from which the electron on the Fe—S clusters has escaped to $O_2$ (or other oxidants).

TABLE 5

Fitting coefficients of $P_{700}^+$ decay in isolated PSI-HydA1 particles

| | Time constant ± SE, ms (relative amplitude, %) | |
|---|---|---|
| Phase assignment | PSI-HydA1 (oxic) | PSI-HydA1 (anoxic) |
| CR of $P_{700}^+(F_AF_B)^-$ | 42 ± 6 (19 ± 3) | 29 ± 2 (28 ± 4) |
| | 183 ± 21 (20 ± 3) | 86 ± 11 (40.5 ± 2.5) |
| CR of $P_{700}^+F_H^-$ | N/A | 269 ± 34 (13.5 ± 3.5) |
| ascorbate | 40,000 ± 4100 (65 ± 5) | 14500 ± 400 (17.8 ± 0.2) |
| Non-decaying | –(5 ± 5) | –(–1.3 ± 0.2) |
| $R^2$ | 0.99968 | 0.99999 |

PSI-HydA1 activity in vitro: The HydEF and HydG maturases are necessary for insertion of the unique diiron site, completing H-cluster assembly of the [FeFe]-hydrogenase. The ΨH2 strain accumulates about 5 times as much photoactive PSI-HydA as the PSI-HydA2 chimera in the ΨH1 mutant. It was thus important to determine the time necessary for maturation of all the PSI-HydA1 chimera, as it might be longer in the ΨH2 strain. The activity of hydrogenase can be assayed in detergent-permeabilized cells using reduced methyl viologen as electron donor. We performed this assay to determine maximal hydrogenase activity in cells after anaerobic adaptation for various amounts of time (FIG. 19). We found that 3 hours of anaerobic adaptation is sufficient to reach a state in which most chimeras contain H-cluster. There was only ~11% increase in the rate

TABLE 4

Fitting coefficients of $P_{700}^+$ decay in thylakoids

| parameter | PSI | PSI-hydrogenase | Comments |
|---|---|---|---|
| $\tau_1$ | 77 ± 4.5 ms | 123 ± 9 ms | Decay constant of fast phase (ms) |
| $A_1$ | 31 ± 0.6% | 23.2 ± 0.6% | Amplitude of fast phase (% of total) |
| $\tau_2$ | 4.3 ± 0.1 s | 10 ± 0.3 s | Decay constant of slow phase (s) |
| $A_2$ | 66 ± 0.5% | 71.1 ± 0.7% | Amplitude of slow phase (% of total) |
| $A_0$ | 1.6 ± 0.3% | 3.7 ± 0.8% | Non-decaying fraction (% of total) |
| $R^2$ | 0.99951 | 0.99931 | Coefficient of determination |

As noted previously, the absence of exogenous electron acceptors is crucial for longevity of charge separated state and measuring charge recombination kinetics. To remove oxygen as a potential electron acceptor, we anaerobically adapted ΨH2 cells and isolated the PSI-HydA1 complex anoxically. Another PSI-HydA1 preparation was accomplished without anaerobic adaptation and in the presence of air as a control. $P_{700}$ recovery kinetics of anoxic and oxic PSI-HydA1 after a single saturating laser flash are presented in FIG. 18B. Decay of $P_{700}^+$ in the oxic preparation could be best described by 3 exponential decay components, with a dominant slow phase (~65% amplitude) and 2 fast components (42 and 183 ms) having similar amplitudes (19-20%) (Table 5). Fitting of the decay of $P_{700}^+$ in the anoxic preparation, however, required a fourth component. The amplitude of the slow phase was significantly reduced, consistent with the absence of $O_2$. Two fast decay components with time constants of 29 ms and 86 ms (and amplitudes of 28% and 40%, respectively) were assigned to charge recombination from $P_{700}^+(F_AF_B)^-$. A novel decay component with a time constant of 270±34 ms and amplitude of 14% was also seen. This is provisionally assigned to charge recombination from the $P_{700}^+F_H^-$ state, indicating that electron transfer from the PsaC domain to the hydrogenase domain occurs upon excitation in at least some of the chimeric PSI-HydA1 complexes. It is noteworthy that WT PSI prepared anoxically lacks 270 ms component.[27]

of $H_2$ production between 3 and 4 hours of anaerobic induction. Longer anaerobic adaptations resulted in decreased activities. Using a ratio of 1100 Chl to $P_{700}$ obtained spectroscopically with thylakoids, we estimated the turnover rate of the PSI-HydA1 chimera as 219±15 $H_2$ $s^{-1}$ in this assay.

Like the PsaC polypeptide, the PsaC-HydA1 chimeric polypeptide is constitutively expressed in the chloroplast, as opposed to anaerobically induced. In contrast, the HydA1 product is increased by at least 6-fold in anoxia[40]. This provided an opportunity to use the methyl viologen assay to monitor the maturation and re-activation of PSI-HydA1 in vivo. Chloramphenicol (CAM) - an inhibitor of translation in the chloroplast[41]—was added to cells immediately before anaerobic adaptation to block further synthesis of PSI-HydA1. (The PsaA, PsaB, PsaC-HydA1 core subunits are all made by chloroplast ribosomes.) After 4 h of anaerobic adaptation, the amount of hydrogenase activity was >90% of the control activity observed without chloramphenicol treatment (FIG. 19, compare red to black). Thus, we conclude that (1) degradation of the PsaC-HydA1 chimera is relatively slow, and (2) the maturases are able to activate apo-PsaC-HydA1 that was synthesized before the shift to anoxia.

To test the ability of the maturase system to re-activate hydrogenase that had been inactivated by exposure to O2, we took control cells that had undergone 4 hours of anaerobic adaptation (in the absence of chloramphenicol) and bubbled them with air for 5 minutes. This was sufficient to kill all the hydrogenase activity, as verified by the assay. Chloramphenicol was added to the receiving vessel during cell transfer to aerobic conditions to prevent synthesis of new PsaC-HydA1 (prior to sparging with air). Another 4 h anaerobic adaptation was performed before measurement of hydrogenase activity. More than 60% of the activity was recovered, indicating that the algal maturases are capable of re-activating hydrogenase in at least half of the active sites previously inactivated by $O_2$ (FIG. 19, compare blue to black).

Hydrogen evolution in vivo: We first examined the chimera's ability to carry out $H_2$ production in vivo in the dark. For $H_2$ production to take place, the electron donor (reduced ferredoxin) must transiently bind to PsaC-HydA1 and transfer an electron to one of the iron-sulfur clusters, ultimately arriving at the H-cluster; this must happen twice for each $H_2$ produced. Since the native binding mode of ferredoxin 1 (the major form) to either HydA1 or PsaC is highly unlikely, according to our modeling (see FIG. 35, 36), it was of great importance to test the ability of ferredoxin to bind the chimera in vivo. With GC-TCD we probed the headspace of cultures in sealed glass bottles to measure hydrogen accumulation by ΨH2 (FIG. 20A, blue symbols). The average rate was $1.13 \pm 0.05$ μmol $H_2$ (mg Chl)$^{-1}$ h$^{-1}$ and remained linear over a 3-hour period (for maximal dark rate see Table 3).

also did not consume $H_2$; in fact, a ~50% increase in headspace $H_2$ was seen overnight.

Addition of 3-(3,4-dichlorophenyl)-1,1-dimethylurea (DCMU)—a potent PSII inhibitor—to cultures without acetate resulted in a ~6-fold decrease in $H_2$ production (FIG. 20A, green symbols). No $O_2$ in the headspace was detected in experiments with DCMU or dark, as expected.

Membrane inlet mass spectrometry (MIMS) was employed to monitor instantaneous rates of gas evolution/consumption. Cells were grown on TAP under low ($\leq 5$ μmol m$^{-2}$ s$^{-1}$ white fluorescent) light, anaerobically adapted (3 h) before being injected into the MIMS cuvette, which was continuously flushed with $N_2$. Once sealed inside the cuvette, the $N_2$ line was removed and ion currents were measured for $H_2$, $O_2$, and $CO_2$ under increasing intermittent illumination followed by continuous illumination. (see FIG. 28 as an example). Maximal rates were determined for 2-min intervals under each illumination intensity followed by 3 min of darkness (plotted vs. light intensity in FIG. 21). Under low $CO_2$ conditions, the $H_2$ production rate saturated at about 600 μmol photons m$^{-2}$ s$^{-1}$ and only slightly increased at double the intensity, with very similar rates in the presence or absence of acetate (see Table 3, FIG. 21A, compare black and red symbols). With addition of 2 mM bicarbonate to acetate-free medium, the saturated $H_2$ evolution rate dropped by ~33% (FIG. 21A, blue symbols). Addition of 10 μM DCMU resulted in a ~10-fold drop in the $H_2$ evolution rate (green symbols), consistent with what was observed in the long-term experiments.

TABLE 3

| Maximal rate μmol $H_2$ (mg Chl)$^{-1}$ h$^{-1}$ | Conditions |
| --- | --- |
| 797 ± 53 | Reduced methyl viologen in permeabilized cells after 4 h of anaerobic induction (GC) (n = 9) |
| 723 ± 140 | Reduced methyl viologen in permeabilized cells (GC) (n = 3) with 200 μg/mL CAM added at the beginning of anaerobic adaptation (4 hours of anaerobic induction) |
| 18 ± 2 | TP under ~200 ± mol m$^{-2}$ s$^{-1}$ (white fluorescent) light (GC) (n = 3) |
| 21 ± 1 | TAP under ~200 ± mol m$^{-2}$ s$^{-1}$ (white fluorescent) light (GC) (n = 3) |
| 1.5 ± 0.3 | TAP in the dark (GC) (n = 6) |
| 3.1 ± 0.3 | TP (+10 μM DCMU) under ~200 ± μmol m$^{-2}$ s$^{-1}$ (white fluorescent) light (GC) (n = 3) |
| 58 ± 14 | TP, under 1170 μmol m$^{-2}$ s$^{-1}$ (red LED) light (MIMS) (n = 5) |
| 59 ± 11 | TAP, under 1170 μmol m$^{-2}$ s$^{-1}$ (red LED) light (MIMS) (n = 3) |
| 39 ± 5 | TP (+2 mM bicarbonate), under 1170 μmol m$^{-2}$ s$^{-1}$ (red LED) light (MIMS) (n = 3) |
| 6 ± 1 | TP (+10 μM DCMU) under 1170 μmol m$^{-2}$ s$^{-1}$ (red LED) light (MIMS) (n = 3) |
| 52 ± 18 | TP (+2 mM bicarbonate + 40 mM GA), under 1170 μmol m$^{-2}$ s$^{-1}$ (red LED) light (MIMS) (n = 3) |

We next measured photobiohydrogen production in closed glass bottles (FIG. 20A). In 1 hour, ΨH2 cells produced $18.4 \pm 2.7$ μmol $H_2$ (mg Chl)$^{-1}$ when supplied with acetate (black), which is not significantly better than without acetate ($17 \pm 2$ μmol of $H_2$ (mg Chl)$^{-1}$; red). In neither case did the ΨH2 cultures produce significant amounts of $H_2$ after 1 hour. Net oxygen evolution (FIG. 20B) was not significantly different in the presence or absence of acetate for the first 2 h ($2 \pm 2$ vs. $2.6 \pm 1$ μmol of $O_2$ (mg Chl)$^{-1}$ h$^{-1}$, respectively; compare red to black).

It is worth mentioning that after 18 hours of illumination, ΨH2 cells in the presence of acetate grew significantly better, consumed some hydrogen from the headspace, and produced copious amounts of oxygen (~8% $O_2$ in the headspace). In the same time period, ΨH2 cells without acetate hardly grew at all and accumulated ~20 times less $O_2$. They The maximal oxygen evolution rate increased with increasing light flux for cultures without acetate (FIG. 21B; FIG. 21A compare black and red symbols, respectively), reaching 5-8 μmol $O_2$ (mg Chl)$^{-1}$ h$^{-1}$. In the presence of acetate, it saturated at 170 μmol photons m$^{-2}$ s$^{-1}$, then dropped by ~60% with increasing light. As expected, addition of DCMU (green) completely inhibited $O_2$ evolution. Under these conditions, the ΨH2 strain did not perform net $CO_2$ uptake but instead evolved $CO_2$ under all light intensities (FIG. 21C). In fact, $CO_2$ evolution increased with increasing light intensity, to a maximal observed rate of 8-11 μmol $CO_2$ (mg Chl)$^{-1}$ h$^{-1}$; it was somewhat higher in the presence of acetate, consistent with higher respiration rates. (The addition of 2 mM bicarbonate rendered the $CO_2$ traces too noisy for reliable analysis.)

The decrease in oxygen evolution rate coincided with an increased $CO_2$ evolution rate (FIG. 21B, C) observed in the presence of acetate at higher light intensities suggesting that two events might be related as a result of increased respiration.

Instantaneous rates of $H_2$ evolution measured during the first 2 min of illumination did not match well the rates observed during longer irradiances (compare FIGS. 20 and 21; except for the DCMU results). The $H_2$ rate starting high quickly dropped to negligible and even under some conditions became negative as can be interpreted from the slope of the $H_2$ trace in FIG. 20A. This was reminiscent of the pattern often reported for the wild-type algal species. Moreover, the fact that there was always net $CO_2$ production rather than consumption indicate that the CBB cycle was largely inactive under these conditions. Lower than expected net $O_2$ production rates were also seen, likely due to either high initial respiration rates or a bottleneck effect created by the PSI-HydA1 chimera similar to what was seen with the PSI-HydA2 construct. The latter effect was corroborated by Chl fluorescence induction measurements (FIG. 33).

Figures 22A, 22B, 22C, 22D:
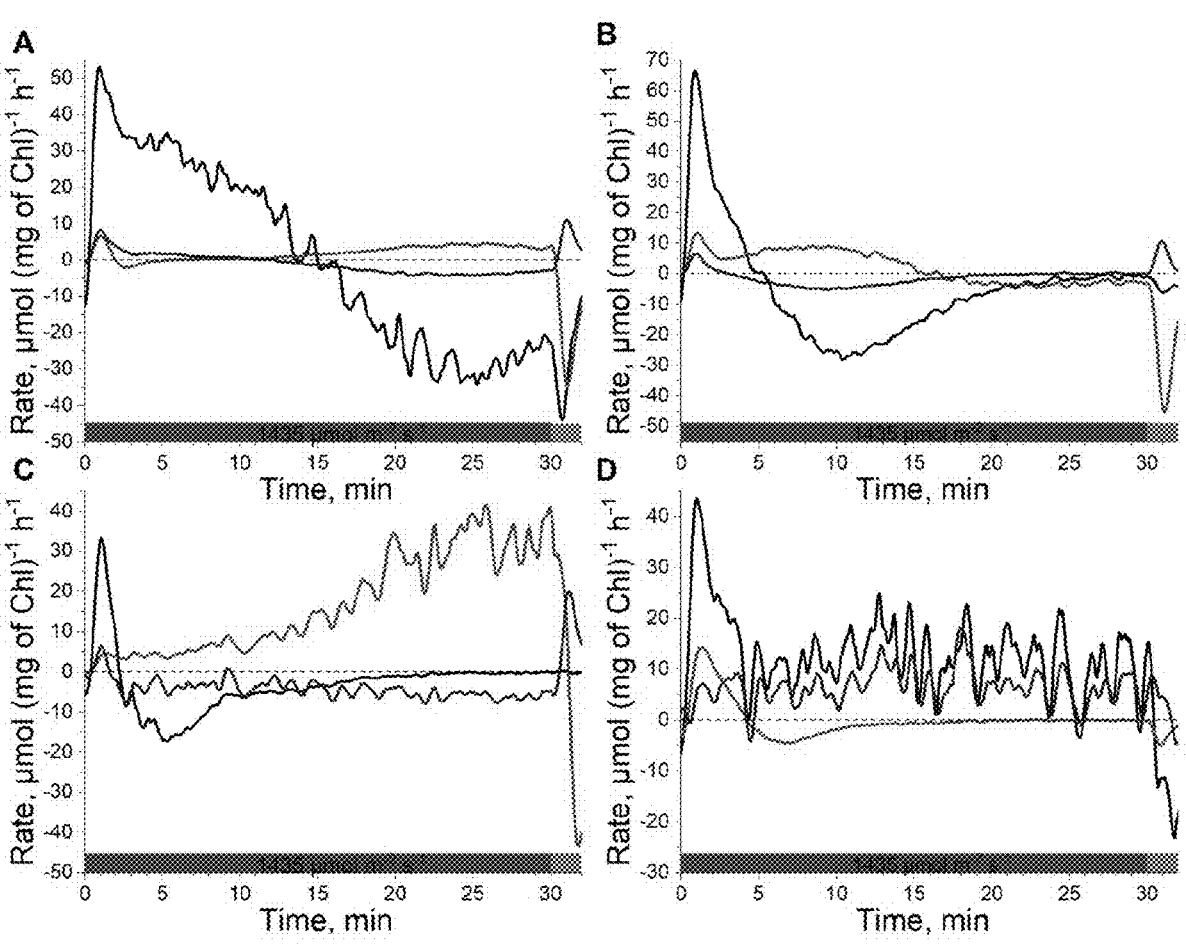

To bridge the gaps in our understanding of physiology of $\Psi$H2 mutant, we monitored $H_2$, $O_2$, and $CO_2$ rates with MIMS during a 30-min period of continuous high illumination (1435 $\mu$mol red photons $m^{-2}$ $s^{-1}$) using cells that had undergone the cycles of increasing light (2 min ON, 3 min OFF) shown in FIG. 22. In $\Psi$H2 cell cultures lacking externally added acetate or bicarbonate, $H_2$ rates exhibited high variability (FIG. 22A). They reached near maximal levels ($53\pm15$ $\mu$mol $H_2$ (mg Chl)$^{-1}$ h$^{-1}$) in 1 minute, followed by a decline that resulted in net $H_2$ uptake after ~14 minutes of illumination. Oxygen rates had a small initial spike (~$7\pm3$ $\mu$mol (mg Chl)$^{-1}$ h$^{-1}$) at the same time that the $H_2$ rate reached maximum, followed up by a dip (net $O_2$ uptake) that mirrored the simultaneous decline in $H_2$ and $CO_2$ production rates. Shortly before the switch of net $H_2$ production to uptake, $O_2$ production rates started to rise again while $CO_2$ rates were net negative, implying increasing activity of the CBB cycle. For reference, dissolved $CO_2$ concentration in water equilibrated with air at 24° C. and atmospheric pressure is ~15 $\mu$M, which is less than what we observed under current conditions. As the lights went out, $H_2$ uptake rates increased, reaching a maximum of $44\pm16$ $\mu$mol $H_2$ (mg Chl)$^{-1}$ h$^{-1}$; this indicates that hydrogenase activity was mostly preserved, since the rate of $H_2$ uptake (presumably catalyzed by the hydrogenase domain fused to PSI) was ~80% of the maximal $H_2$ production rate in the light. The respiration rate in the dark reached ~$35\pm12$ $\mu$mol of $O_2$ (mg Chl)$^{-1}$ h$^{-1}$ as $CO_2$ fixation switched to $CO_2$ evolution (~$11\pm3$ $\mu$mol of $CO_2$ (mg Chl)$^{-1}$ h$^{-1}$). Dissolved $O_2$ rose to its highest level (~$20\pm6$ $\mu$M) only towards the end of the illumination and is likely responsible for the partial inactivation of the chimeric protein (FIG. 30A; red).

Under similar conditions, wild type cells (D66) exhibited a sudden surge in $H_2$ evolution that switched to net $H_2$ uptake within 5 min, three times faster than the $\Psi$H2 strain (FIG. 22B). The $O_2$ production rate swelled to $14\pm9$ 82 mol (mg Chl)$^{-1}$ h$^{-1}$ followed up by a dip associated with $H_2$ uptake. Shortly after, $CO_2$ fixation commenced, reaching –5 $\mu$mol $CO_2$ (mg Chl)$^{-1}$ h$^{-1}$. After 15 minutes, the net $CO_2$ rate approached the compensation point due to apparent substrate limitation (no exogenous bicarbonate was added to the media and $CO_2$ concentration decreased considerably—FIG. 30B). Interestingly, after the light went out, there was still some residual hydrogenase activity, judging by a drop in $H_2$ uptake in the dark (–5 $\mu$mol $H_2$ (mg Chl)$^{-1}$ h$^{-1}$, which is ~7% of the maximal production rate in the light). This can be explained by a rise in $O_2$, up to $37\pm26$ $\mu$M, inactivating most of the endogenous hydrogenase activity with relative abundance of $H_2$ excluding substrate limiting nature of the drop. $CO_2$ rate increased to about 10 $\mu$mol (mg Chl)$^{-1}$ h$^{-1}$ and oxygen consumption briefly reached 45 $\mu$mol (mg Chl)$^{-1}$ h$^{-1}$ as expected for respiration in the dark.

Under conditions of excess bicarbonate (without acetate), $\Psi$H2 cells showed a much smaller initial surge in $H_2$ evolution (~35 $\mu$mol $H_2$ (mg Chl)$^{-1}$ h$^{-1}$), which switched to $H_2$ uptake within 2 minutes of the onset of light (FIG. 22C). This led to rapid depletion of the dissolved $H_2$ pool within 15-20 min (FIG. 30C). At the same time, oxygen rates were higher and continued climbing, reaching ~35-40 $\mu$mol $O_2$ (mg Chl)$^{-1}$ h$^{-1}$. Onset of $CO_2$ fixation coincided with inflection point of $H_2$ rate and remained steady for the rest of the experiment. Once the light was off, there was no $H_2$ uptake, as there was essentially no $H_2$ left in the media. The $O_2$ uptake rate was 45 $\mu$mol (mg Chl)$^{-1}$ h$^{-1}$ and $CO_2$ evolution reached ~20 $\mu$mol (mg Chl)$^{-1}$ h$^{-1}$. The lesser than expected rate of $CO_2$ evolution is likely because of its partial conversion to bicarbonate at pH ~7 due to its weak acid properties.

Addition of 40 mM glycol aldehyde (GA)—an inhibitor of the CBB cycle—to $\Psi$H2 cells in the presence of excess bicarbonate resulted in an initial $H_2$ evolution rate of ~45 $\mu$mol (mg Chl)$^{-1}$ h$^{-1}$ (FIG. 22D). This represents an improvement when compared with $\Psi$H2 cells with 2 mM bicarbonate. The H2 production rate remained overall positive for the duration of illumination, although the signal was noisy. Only after the light was off did it become negative (~–25 $\mu$mol $H_2$ (mg Chl)$^{-1}$ h$^{-1}$). The $O_2$ evolution rate spiked immediately to 15 $\mu$mol (mg Chl)$^{-1}$ h$^{-1}$, followed by a negative dip and then approached the compensation point for the remainder of the experiment. Similarly, dissolved $O_2$ increased briefly to ~10 $\mu$M and quickly dropped to near zero for the rest of the illumination period (FIG. 30D). As the light was off, the rate became negative (–5 $\mu$mol (mg Chl)$^{-1}$ h$^{-1}$, which is small due to lack of available $O_2$). The $CO_2$ production rate remained positive during the experiment, indicating that no carbon fixation was taking place, as expected.

Our previous observations of the $\Psi$H1 mutant demonstrated the benefits of adding acetate to the media for photobiohydrogen production, in terms of both maximal rate and longevity. Our long-term experiments with $\Psi$H2 did not show a clear advantage of having acetate in the media for photobiohydrogen production (FIG. 20), likely due to the $H_2$ consumption during cell growth. On the other hand, maximal $H_2$ rates during light saturation indicated that $H_2$ production benefited from addition of acetate especially at lower light intensities (FIG. 21A). To further explore this phenomenon, we extended illumination on the MIMS $\Psi$H2 samples containing acetate and found large variability between runs (FIG. 23). In the lowest performing trial, $H_2$ production rate at the light onset was only 33 $\mu$mol (mg Chl)$^{-1}$ h$^{-1}$ and quickly dwindled followed up by $H_2$ uptake (after 9 min of illumination) (FIG. 23A). $H_2$ consumption coincided with increasing rate of carbon fixation and decreased only when $H_2$ concentration dropped below 10 $\mu$M (FIG. 31A, black). At the time of $H_2$ depletion, $O_2$ concentration started to build up (FIG. 31A, red) that could also have negative effect on hydrogenase activity. Nevertheless, there was at least 30% hydrogenase activity remained intact in the dark as judged by $H_2$ uptake following switching the lights off. $O_2$ rate had a tiny spike and then remained close to zero getting slightly positive in the last 7 min of illumination with $O_2$ reaching 6.4 $\mu$M. In the dark, oxygen rate dropped to –20 $\mu$mol (mg Chl)$^{-1}$ h$^{-1}$ and was limited by $O_2$ concentration. $CO_2$ showed surplus rate for the first 9 min followed up by $CO_2$ consumption. Once the light was off, $CO_2$ rate jumped to ~20 μmol (mg Chl)$^{-1}$ h$^{-1}$.

In the best performing trial (FIG. 23B), ΨH2 cells had high initial hydrogen production rate (60 μmol (mg Chl)$^{-1}$ h$^{-1}$ that fell gradually to ~5 μmol (mg Chl)$^{-1}$ h$^{-1}$ but never switched to net $H_2$ uptake during first 30 min of illumination. Net oxygen rate was close to zero and $CO_2$ rate was slightly positive in the first 30 min indicating minimal CBB cycle activity. During 2 min of darkness, $H_2$ uptake rate was rather small (−5 μmol (mg Chl)$^{-1}$ h$^{-1}$), despite ~180 μM of $H_2$ available (FIG. 31B) and oxygen uptake was non-existent (due to lack of $O_2$). Interestingly, a small $CO_2$ uptake in the dark coincided with $H_2$ uptake in the dark. Since 30 min illumination did not lead to high activity of CBB cycle, we decided to proceed and turn illumination back on. $H_2$ spiked to 15 μmol (mg Chl)$^{-1}$ h$^{-1}$ then decreased but remained positive for the next 90 min of illumination. $O_2$ and $CO_2$ rates remained close to zero. $H_2$ concentration reached 192 μM, $O_2$ stayed less than 2 μM and $CO_2$ less than 41 μM. After about 2 hours since onset of continuous illumination, we decided to add bicarbonate—a substrate for RuBisCO. It triggered profound changes resulting in $H_2$ uptake rate −50 μmol (mg Chl)$^{-1}$ h$^{-1}$ and activation of CBB cycle as judged by $CO_2$ uptake rate. Absence of steep raise in oxygen levels suggest that most electrons came from hydrogen oxidation rather than water oxidation and/or oxygen was partially oxidized by PSI-HydA1 chimera. It is worth noting that initial $CO_2$ concentration at the onset of long illumination between the worst and the best performing trial was not so much different (43 μM vs 33 μM) as well as their maximum levels (52 μM vs 42 μM). Moreover, $CO_2$ concentration in cultures without acetate (FIG. 30A, blue) was much less on average (~20 μM) yet resulted in CBB activation.

Cyclic electron flow (CEF) in ΨH2 in vivo: CEF around PSI is an effective way to deal with ATP shortages in the light. In the typical paradigm of oxygenic photosynthesis, electrons from the acceptor side of PSI can enter the plastoquinone pool, thus forming a cycle. To test ΨH2's ability to perform CEF under fully aerobic conditions (where they cannot make $H_2$), we added 10 μM DCMU to cells and then illuminated them for 10 s, after which the $P_{700}^+$ decay rate was measured as a proxy for CEF (FIG. 34). We found that the rate constant for $P_{700}^+$ decay in ΨH2 was 36.6±4.4 s$^{-1}$, which is almost twice the rate of D66 (WT) strain (15.4±0.4 s$^{-1}$). Addition of 20 μM DBMIB—an inhibitor of the $Q_o$ site of cytochrome $b_6f$—resulted in low rates of decay in both strains (~2-2.5 s$^{-1}$). The higher rate of $P_{700}^+$ recovery in ΨH2 might be due to adaptation to low activity of CBB cycle and overreduction of $NADPH_2$ pool.

REFERENCES

1 Hydrogen Council, Hydrogen Insights 2021, 2021.

2 J. Swartz, Curr. Opin. Biotechnol., 2020, 62, 248-255.

3 A. Stirbet, D. Lazár, Y. Guo and G. Govindjee, Ann. Bot., 2020, 126, 511-537.

4 W. J. Nawrocki, B. Bailleul, D. Picot, P. Cardol, F. Rappaport, F.-A. Wollman and P. Joliot, Biochim. Biophys. Acta—Bioenerg., 2019, 1860, 433-438.

5 L. Cournac, F. Mus, L. Bernard, G. Guedeney, P. M. Vignais and G. Peltier, Int. J. Hydrogen Energy, 2002, 27, 1229-1237.

6 S. Clowez, D. Godaux, P. Cardol, F.-A. Wollman and F. Rappaport, J. Biol. Chem., 2015, 290, 8666-8676.

7 Y. Milrad, S. Schweitzer, Y. Feldman and I. Yacoby, Plant Physiol., 2018, 177, 918-926.

8 D. Godaux, B. Bailleul, N. Berne and P. Cardol, Plant Physiol., 2015, 168, 648-658.

9 A. Burlacot, A. Sawyer, S. Cuiné, P. Auroy-Tarrago, S. Blangy, T. Happe and G. Peltier, Plant Physiol., 2018, 177, 1639 LP-1649.

10 W. Lubitz, H. Ogata, O. Rüdiger and E. Reijerse, Chem. Rev., 2014, 114, 4081-4148.

11 M. Winkler, S. Kuhlgert, M. Hippler and T. Happe, J. Biol. Chem., 2009, 284, 36620-36627.

12 M. Winkler, A. Hemschemeier, J. Jacobs, S. Stripp and T. Happe, Eur. J. Cell Biol., 2010, 89, 998-1004.

13 Y. Milrad, S. Schweitzer, Y. Feldman and I. Yacoby, Plant Physiol., 2021, 186, 168-179.

14 M. C. Posewitz, P. W. King, S. L. Smolinski, L. Zhang, M. Seibert and M. L. Ghirardi, J. Biol. Chem., 2004, 279, 25711-25720.

15 G. Berggren, A. Adamska, C. Lambertz, T. R. Simmons, J. Esselborn, M. Atta, S. Gambarelli, J.-M. Mouesca, E. Reijerse, W. Lubitz, T. Happe, V. Artero and M. Fontecave, Nature, 2013, 499, 66-69.

16 Y. Bai, T. Chen, T. Happe, Y. Lu and A. Sawyer, Metallomics, 2018, 10, 1038-1052.

17 R. D. Britt, L. Tao, G. Rao, N. Chen and L.-P. Wang, ACS Bio Med Chem Au, 2021, acsbiomedchemau.1c00035.

18 A. Kubas, C. Orain, D. De Sancho, L. Saujet, M. Sensi, C. Gauquelin, I. Meynial-Salles, P. Soucaille, H. Bottin, C. Baffert, V. Fourmond, R. B. Best, J. Blumberger and C. Léger, Nat. Chem., DOI:10.1038/nchem.2592.

19 K. D. Swanson, M. W. Ratzloff, D. W. Mulder, J. H. Artz, S. Ghose, A. Hoffman, S. White, O. A. Zadvornyy, J. B. Broderick, B. Bothner, P. W. King and J. W. Peters, J. Am. Chem. Soc., 2015, 137, 1809-1816.

20 S. T. Stripp, G. Goldet, C. Brandmayr, O. Sanganas, K. A. Vincent, M. Haumann, F. A. Armstrong and T. Happe, Proc. Natl. Acad. Sci., 2009, 106, 17331-17336.

21 T. S. Pinto, F. X. Malcata, J. D. Arrabaça, J. M. Silva, R. J. Spreitzer and M. G. Esquível, Appl. Microbiol. Biotechnol., 2013, 97, 5635-5643.

22 A. Melis, L. Zhang, M. Forestier, M. L. Ghirardi and M. Seibert, Plant Physiol., 2000, 122, 127-136.

23 S. Kosourov, M. Jokel, E. M. Aro and Y. Allahverdiyeva, Energy Environ. Sci., 2018, 1-2.

24 O. Ben-Zvi, E. Dafni, Y. Feldman and I. Yacoby, Biotechnol. Biofuels, 2019, 12, 266.

25 H. Eilenberg, I. Weiner, O. Ben-Zvi, C. Pundak, A. Marmari, O. Liran, M. S. Wecker, Y. Milrad and I. Yacoby, Biotechnol. Biofuels, 2016, 9, 182.

26 I. Yacoby, S. Pochekailov, H. Toporik, M. L. Ghirardi, P. W. King and S. Zhang, Proc. Natl. Acad. Sci., 2011, 108, 9396-9401.

27 A. Kanygin, Y. Milrad, C. Thummala, K. Reifschneider, P. Baker, P. Marco, I. Yacoby and K. E. Redding, Energy Environ. Sci., 2020, 13, 2903-2914.

28 T. Happe and A. Kaminski, Eur. J. Biochem., 2002, 269, 1022-1032.

29 X. Su, J. Ma, X. Pan, X. Zhao, W. Chang, Z. Liu, X. Zhang and M. Li, Nat. Plants, 2019, 5, 273-281.

30 Y. Song, F. DiMaio, R. Y.-R. Wang, D. Kim, C. Miles, T. Brunette, J. Thompson and D. Baker, Structure, 2013, 21, 1735-1742.

31 L. Schrödinger, The {PyMOL} Molecular Graphics System, Version 2.4.0, 2015.

32 S. Rumpel, J. F. Siebel, M. Diallo, C. Farès, E. J. Reijerse and W. Lubitz, Chem Bio Chem, 2015, 16, 1663-1669.

33 J. E. Meuser, S. D'Adamo, R. E. Jinkerson, F. Mus, W. Yang, M. L. Ghirardi, M. Seibert, A. R. Grossman and M. C. Posewitz, Biochem. Biophys. Res. Commun., 2012, 417, 704-709.

34 J. Kropat, A. Hong-Hermesdorf, D. Casero, P. Ent, M. Castruita, M. Pellegrini, S. S. Merchant and D. Malasarn, Plant J., 2011, 66, 770-780.

35 R. J. Porra, W. A. Thompson and P. E. Kriedemann, Biochim. Biophys. Acta—Bioenerg., 1989, 975, 384-394.

36 N. Fischer, P. Sétif and J. D. Rochaix, Biochemistry, 1997, 36, 93-102.

37 G. Gulis, K. V Narasimhulu, L. N. Fox and K. E. Redding, Photosynth. Res., 2008, 96, 51-60.

38 A. Burlacot, F. Burlacot, Y. Li-Beisson and G. Peltier, Front. Plant Sci., DOI:10.3389/fpls.2020.01302.

39 B. Genty, J.-M. Briantais and N. R. Baker, Biochim. Biophys. Acta—Gen. Subj., 1989, 990, 87-92.

40 D. Nikolova, C. Heilmann, S. Hawat, P. Gäbelein and M. Hippler, Photosynth. Res., 2018, 137, 281-293.

41 J. K. Hoobert and G. Blobel, J. Mol. Biol., 1969, 41, 121-138.

42 S. Kosourov, V. Nagy, D. Shevela, M. Jokel, J. Messinger and Y. Allahverdiyeva, Proc. Natl. Acad. Sci., 2020, 202009210.

43 S. Tirumani, K. M. Gothandam and B. J Rao, Protoplasma, 2019, 256, 117-130.

44 X. Xie, A. Huang, W. Gu, Z. Zang, G. Pan, S. Gao, L. He, B. Zhang, J. Niu, A. Lin and G. Wang, New Phytol., 2016, 209, 987-998.

45 I. Polukhina, R. Fristedt, E. Dinc, P. Cardol and R. Croce, Plant Physiol., 2016, 172, 1494-1505.

46 X. Johnson and J. Alric, J. Biol. Chem., 2012, 287, 26445-26452.

47 T. Urbig, R. Schulz and H. Senger, Zeitschrift für Naturforsch. C, 1993, 48, 41-45.

48 W. M. Kaiser, Planta, 1979, 145, 377-382.

49 S. Yadav and N. Atri, in Reactive Oxygen Species in Plants, John Wiley & Sons, Ltd, Chichester, UK, 2017, pp. 157-163.

50 D. J. Cashman, T. Zhu, R. F. Simmerman, C. Scott, B. D. Bruce and J. Baudry, J. Mol. Recognit., 2014, 27, 597-608.

1 M. Forestier, P. King, L. Zhang, M. Posewitz, S. Schwarzer, T. Happe, M. L. Ghirardi and M. Seibert, Eur. J. Biochem., 2003, 270, 2750-2758.

SEQUENCE LISTING

```
Sequence total quantity: 15
SEQ ID NO: 1              moltype = AA  length = 517
FEATURE                  Location/Qualifiers
REGION                   1..517
                         note = Synthetic- PsaC-HydA2 fusion polypeptide
source                   1..517
                         mol_type = protein
                         organism = synthetic construct
SEQUENCE: 1
MAHIVKIYDT CIGCTQCVRA CPLDVLEMVP WGGATATDAV PHWKLALEEL DKPKDGGRKV  60
LIAQVAPAVR VAIAESFGLA PGAVSPGKLA TGLRALGFDQ VFDTLFAADL TIMEEGTELL  120
HRLKEHLEAH PHSDEPLPMF TSCCPGWVAM MEKSYPELIP FVSSCKSPQM MMGAMVKTYL  180
SEKQGIPAKD IVMVSVMPCV RKQGEADREW FCVSEPGVRD VDHVITTAEL GNIFKERGIN  240
LPELPDSDWD QPLGLGSGAG VLFGTTGGVM EAALRTAYEI VTKEPLPRLN LSEVRGLDGI  300
KEASVTLVPA PGSKFAELVA ERLAHKVEEA AAAEAAAAVE GAVKPPIAYD GGQGFSTDDG  360
KGGLKLRVAV ANGLGNAKKL IGKMVSGEAK YDFVEIMACP AGCVGGGGQP RSTDKQITQK  420
RQAALYDLDE RNTLRRSHEN EAVNQLYKEF LGEPLSHRAH ELLHTHYVPG GASQMASAPR  480
TEDCVGCKRC ETACPTDFLS VRVYLGSEST RSMGLSY                          517

SEQ ID NO: 2              moltype = AA  length = 510
FEATURE                  Location/Qualifiers
REGION                   1..510
                         note = Synthetic- PsaC-HydA1 fusion polypeptide
source                   1..510
                         mol_type = protein
                         organism = synthetic construct
SEQUENCE: 2
MAHIVKIYDT CIGCTQCVRA CPLDVLEMVP WGGATATDAV PHVQQALAEL AKPKDDPTRK  60
HVCVQVAPAV RVAIAETLGL APGATTPKQL AEGLRRLGFD EVFDTLFGAD LTIMEEGSEL  120
LHRLTEHLEA HPHSDEPLPM FTSCCPGWIA MLEKSYPDLI PYVSSCKSPQ MMLAAMVKSY  180
LAEKKGIAPK DMVMVSIMPC TRKQSEADRD WFCVDADPTL RQLDHVITTV ELGNIFKERG  240
INLAELPEGE WDNPMGVGSG AGVLFGTTGG VMEAALRTAY ELFTGTPLPR LSLSEVRGMD  300
GIKETNITMV PAPGSKFEEL LKHRAAARAE AAAHGTPGPL AWDGGAGFTS EDGRGGITLR  360
VAVANGLGNA KKLITKMQAG EAKYDFVEIM ACPAGCVGGG GQPRSTDKAI TQKRQAALYN  420
LDEKSTLRRS HENPSIRELY DTYLGEPLGH KAHELLHTHY VAGGASQMAS APRTEDCVGC  480
KRCETACPTD FLSVRVYLGS ESTRSMGLSY                                  510

SEQ ID NO: 3              moltype = AA  length = 441
FEATURE                  Location/Qualifiers
REGION                   1..441
                         note = MISC_FEATURE - HydA1
source                   1..441
                         mol_type = protein
                         organism = Chlamydomonas reinhardtii
SEQUENCE: 3
AAPAAEAPLS HVQQALAELA KPKDDPTRKH VCVQVAPAVR VAIAETLGLA PGATTPKQLA  60
EGLRRLGFDE VFDTLFGADL TIMEEGSELL HRLTEHLEAH PHSDEPLPMF TSCCPGWIAM  120
LEKSYPDLIP YVSSCKSPQM MLAAMVKSYL AEKKGIAPKD MVMVSIMPCT RKQSEADRDW  180
```

-continued

```
FCVDADPTLR QLDHVITTVE LGNIFKERGI NLAELPEGEW DNPMGVGSGA GVLFGTTGGV   240
MEAALRTAYE LFTGTPLPRL SLSEVRGMDG IKETNITMVP APGSKFEELL KHRAAARAEA   300
AAHGTPGPLA WDGGAGFTSE DGRGGITLRV AVANGLGNAK KLITKMQAGE AKYDFVEIMA   360
CPAGCVGGGG QPRSTDKAIT QKRQAALYNL DEKSTLRRSH ENPSIRELYD TYLGEPLGHK   420
AHELLHTHYV AGGVEEKDEK K                                            441

SEQ ID NO: 4                moltype = AA   length = 442
FEATURE                     Location/Qualifiers
REGION                      1..442
                            note = MISC_FEATURE - HydA2
source                      1..442
                            mol_type = protein
                            organism = Chlamydomonas reinhardtii
SEQUENCE: 4
TATDAVPHWK LALEELDKPK DGGRKVLIAQ VAPAVRVAIA ESFGLAPGAV SPGKLATGLR   60
ALGFDQVFDT LFAADLTIME EGTELLHRLK EHLEAHPHSD EPLPMFTSCC PGWVAMMEKS   120
YPELIPFVSS CKSPQMMMGA MVKTYLSEKQ GIPAKDIVMV SVMPCVRKQG EADREWFCVS   180
EPGVRDVDHV ITTAELGNIF KERGINLPEL PDSDWDQPLG LGSGAGVLFG TTGGVMEAAL   240
RTAYEIVTKE PLPRLNLSEV RGLDGIKEAS VTLVPAPGSK FAELVAERLA HKVEEAAAEE   300
AAAAVEGAVK PPIAYDGGQG FSTDDGKGGL KLRVAVANGL GNAKKLIGKM VSGEAKYDFV   360
EIMACPAGCV GGGGQPRSTD KQITQKRQAA LYDLDERNTL RRSHENEAVN QLYKEELGEP   420
LSHRAHELLH THYVPGGAEA DA                                           442

SEQ ID NO: 5                moltype = AA   length = 81
FEATURE                     Location/Qualifiers
REGION                      1..81
                            note = MISC_FEATURE - PsaC
source                      1..81
                            mol_type = protein
                            organism = Chlamydomonas reinhardtii
SEQUENCE: 5
MAHIVKIYDT CIGCTQCVRA CPLDVLEMVP WDGCKASQMA SAPRTEDCVG CKRCETACPT   60
DFLSVRVYLG SESTRSMGLS Y                                            81

SEQ ID NO: 6                moltype = AA   length = 81
FEATURE                     Location/Qualifiers
REGION                      1..81
                            note = MISC_FEATURE - PsaC
source                      1..81
                            mol_type = protein
                            organism = Chlorella vulgaris
SEQUENCE: 6
MSHTVKIYDT CIGCTQCVRA CPTDVLEMVP WDGCKASQIA SAPRTEDCVG CKRCESACPT   60
DFLSVRVYLG SETTRSMGLA Y                                            81

SEQ ID NO: 7                moltype = AA   length = 81
FEATURE                     Location/Qualifiers
REGION                      1..81
                            note = MISC_FEATURE - PsaC
source                      1..81
                            mol_type = protein
                            organism = Picocheyletus sp.
SEQUENCE: 7
MSHTVKIYDT CIGCTQCVRA CPTDVLEMVP WNGCKANQIA SAPRTEDCVG CKRCESACPT   60
DFLSVRVYLG AETTRSMGLA Y                                            81

SEQ ID NO: 8                moltype = AA   length = 81
FEATURE                     Location/Qualifiers
REGION                      1..81
                            note = MISC_FEATURE - PsaC
source                      1..81
                            mol_type = protein
                            organism = Cyanidioschyzon merolae
SEQUENCE: 8
MAHTVKIYDN CIGCTQCVRA CPLDVLEMVP WDGCKAGQMA SAPRTEDCVG CKRCETACPT   60
DFLSIRVYLG GETTRSMGLA Y                                            81

SEQ ID NO: 9                moltype = AA   length = 434
FEATURE                     Location/Qualifiers
REGION                      1..434
                            note = MISC_FEATURE - HydA
source                      1..434
                            mol_type = protein
                            organism = Chlorella DT
SEQUENCE: 9
MCCPVVASRH AGRARHVAVR AAGPTSECDC PPTPQAKLPH WQQALDELAK PKESRRLMIA   60
QIAPAVRVAI AETIGLAPGD VTIGQLVTGL RMLGFDYVFD TLFGADLTIM EEGTELLHRL   120
QDHLEQHPNK EEPLPMFTSC CPGWVAMVEK SNPELIPYLS SCKSPQMMLG AVIKNYYAQQ   180
VGVQPSDICN VSVMPCVRKQ GEADREWFNT TGLARDVDHV VTTAEVGKIF LERGIKLNEL   240
```

-continued

```
PESNFDNPIG EGTGGALLFG TTGGVMEAAL RTVYEVVTQK PMGRVDFEEV RGLEGIKEAE   300
ITLKPGDDSP FKAFAGADGQ GITLKIAVAN GLGNAKKLIK SLSEGKAKYD FIEVMACPGG   360
CIGGGGQPRS TDKQILQKRQ QAMYNLDERS AIRRSHENPF IQALYDKFLG APNSHKAHDL   420
LHTHYVAGGI PEEK                                                     434

SEQ ID NO: 10             moltype = DNA   length = 23
FEATURE                   Location/Qualifiers
misc_feature              1..23
                          note = Synthetic-PsaC5' flanking primers
source                    1..23
                          mol_type = other DNA
                          organism = synthetic construct
SEQUENCE: 10
taatatggag atgacatatt tag                                             23

SEQ ID NO: 11             moltype = DNA   length = 20
FEATURE                   Location/Qualifiers
misc_feature              1..20
                          note = Synthetic- PsaC3' primers
source                    1..20
                          mol_type = other DNA
                          organism = synthetic construct
SEQUENCE: 11
gatctcacca agatactccc                                                 20

SEQ ID NO: 12             moltype = DNA   length = 21
FEATURE                   Location/Qualifiers
misc_feature              1..21
                          note = Synthetic- PsaC5'int primers
source                    1..21
                          mol_type = other DNA
                          organism = synthetic construct
SEQUENCE: 12
tcaatgtgta cgtgcttgtc c                                               21

SEQ ID NO: 13             moltype = DNA   length = 21
FEATURE                   Location/Qualifiers
misc_feature              1..21
                          note = Synthetic- PsaC3'int primers
source                    1..21
                          mol_type = other DNA
                          organism = synthetic construct
SEQUENCE: 13
acaacgtttg caacctacac a                                               21

SEQ ID NO: 14             moltype = AA   length = 5
FEATURE                   Location/Qualifiers
REGION                    1..5
                          note = MISC_FEATURE - PsaC outerloop residues
REGION                    1..5
                          note = MISC_FEATURE - PsaC outerloop residues
source                    1..5
                          mol_type = protein
                          organism = Chlamydomonas reinhardtii
SEQUENCE: 14
DGCKA                                                                  5

SEQ ID NO: 15             moltype = AA   length = 10
FEATURE                   Location/Qualifiers
REGION                    1..10
                          note = MISC_FEATURE - HydA1 unstructured region leading to
                           first alpha-helix
REGION                    1..10
                          note = MISC_FEATURE - HydA1 unstructured region leading to
                           first alpha-helix
source                    1..10
                          mol_type = protein
                          organism = Chlamydomonas reinhardtii
SEQUENCE: 15
AAPAAEAPLS                                                            10
```

We claim:

1. A fusion protein comprising a photosystem I subunit (PsaC) protein and an algal hydrogenase, wherein the hydrogenase is inserted into the hinge region of the PsaC.

2. The fusion protein of claim 1, wherein the algal hydrogenase is hydrogenase A.

3. The fusion protein of claim 2, further comprising at least one amino acid at a junction between the PsaC and the N-terminal, the C-terminal, or both ends of the hydrogenase.

4. The fusion protein of claim 1, wherein the fusion protein comprises SEQ ID NO: 1, SEQ ID NO: 2 or a polypeptide having 95% identity to SEQ ID NO: 1 or SEQ ID NO: 2.

* * * * *